US008497073B2

(12) United States Patent
Salafsky

(10) Patent No.: US 8,497,073 B2
(45) Date of Patent: Jul. 30, 2013

(54) METHOD USING A NONLINEAR OPTICAL TECHNIQUE FOR DETECTION OF INTERACTIONS INVOLVING A CONFORMATIONAL CHANGE

(75) Inventor: Joshua S. Salafsky, Burlingame, CA (US)

(73) Assignee: Biodesy, LLC, Burlingame, CA (US)

( * ) Notice: Subject to any disclaimer, the term of this patent is extended or adjusted under 35 U.S.C. 154(b) by 0 days.

(21) Appl. No.: 12/571,342

(22) Filed: Sep. 30, 2009

(65) Prior Publication Data

US 2010/0120164 A1    May 13, 2010

Related U.S. Application Data

(63) Continuation of application No. 11/327,199, filed on Jan. 5, 2006, now abandoned, which is a continuation of application No. 10/164,915, filed on Jun. 6, 2002, now abandoned.

(60) Provisional application No. 60/362,003, filed on Mar. 5, 2002, provisional application No. 60/354,679, filed on Feb. 6, 2002, provisional application No. 60/354,668, filed on Feb. 6, 2002, provisional application No. 60/351,879, filed on Jan. 24, 2002.

(51) Int. Cl.
*G01N 33/53* (2006.01)

(52) U.S. Cl.
USPC .......................................................... 435/7.1

(58) Field of Classification Search
None
See application file for complete search history.

(56) References Cited

U.S. PATENT DOCUMENTS

| | | | |
|---|---|---|---|
| 4,739,044 A | 4/1988 | Stabinsky | |
| 4,757,141 A | 7/1988 | Fung et al. | |
| 4,997,928 A | 3/1991 | Hobbs, Jr. | |
| 5,143,854 A | 9/1992 | Pirrung et al. | |
| 5,156,810 A * | 10/1992 | Ribi | 422/82.01 |
| 5,231,191 A | 7/1993 | Woo et al. | |
| 5,244,813 A | 9/1993 | Walt et al. | |
| 5,250,264 A | 10/1993 | Walt et al. | |
| 5,252,494 A | 10/1993 | Walt | |
| 5,298,741 A | 3/1994 | Walt et al. | |
| 5,320,814 A | 6/1994 | Walt et al. | |
| 5,324,591 A | 6/1994 | Georger, Jr. et al. | |
| 5,324,633 A | 6/1994 | Fodor et al. | |
| 5,376,556 A * | 12/1994 | Tarcha et al. | 436/525 |
| 5,432,610 A | 7/1995 | King et al. | |
| 5,485,277 A | 1/1996 | Foster | |
| 5,512,490 A | 4/1996 | Walt et al. | |
| 5,631,734 A | 5/1997 | Stern et al. | |
| 5,633,724 A * | 5/1997 | King et al. | 356/445 |
| 5,800,992 A | 9/1998 | Fodor et al. | |
| 5,814,524 A | 9/1998 | Walt et al. | |
| 5,834,758 A | 11/1998 | Trulson et al. | |
| 5,847,400 A | 12/1998 | Kain et al. | |
| 6,023,540 A | 2/2000 | Walt et al. | |
| 6,025,601 A | 2/2000 | Trulson et al. | |
| 6,040,586 A | 3/2000 | Slettnes | |
| 6,084,991 A | 7/2000 | Sampas | |
| 6,095,555 A | 8/2000 | Becker et al. | |
| 6,096,497 A | 8/2000 | Bauer et al. | |
| 6,110,426 A | 8/2000 | Shalon et al. | |
| 6,121,983 A | 9/2000 | Fork et al. | |
| 6,124,102 A | 9/2000 | Fodor et al. | |
| 6,134,002 A | 10/2000 | Stimson et al. | |
| 6,180,415 B1 * | 1/2001 | Schultz et al. | 436/518 |
| 6,410,245 B1 * | 6/2002 | Northrop et al. | 506/9 |
| 6,455,303 B1 | 9/2002 | Orwar et al. | |
| 6,456,423 B1 | 9/2002 | Nayfeh et al. | |
| 6,753,200 B2 | 6/2004 | Craighead et al. | |
| 6,917,726 B2 | 7/2005 | Levene et al. | |
| 6,953,694 B2 * | 10/2005 | Salafsky et al. | 436/164 |
| 7,013,054 B2 | 3/2006 | Levene et al. | |
| 7,033,764 B2 | 4/2006 | Korlach et al. | |
| 7,045,337 B2 | 5/2006 | Schultz et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,108,970 B2 * | 9/2006 | Levinson | 435/6.11 |
| 7,181,122 B1 | 2/2007 | Levene et al. | |
| 7,292,742 B2 | 11/2007 | Levene et al. | |
| 7,316,769 B2 | 1/2008 | Craighead et al. | |
| 7,336,359 B1 * | 2/2008 | Simpson et al. | 356/364 |
| 7,336,389 B2 * | 2/2008 | Silverbrook et al. | 358/1.18 |
| 7,361,466 B2 | 4/2008 | Korlach et al. | |
| 7,416,844 B2 | 8/2008 | Korlach et al. | |
| 7,473,361 B2 | 1/2009 | Craighead et al. | |
| 7,485,424 B2 | 2/2009 | Korlach et al. | |
| 2002/0094528 A1 | 7/2002 | Salafsky | |
| 2002/0127563 A1 | 9/2002 | Salafsky | |
| 2003/0148391 A1 * | 8/2003 | Salafsky | 435/7.2 |
| 2004/0146460 A1 | 7/2004 | Salafsky | |
| 2006/0228725 A1 * | 10/2006 | Salafsky | 435/6 |
| 2010/0068144 A1 * | 3/2010 | Salafsky | 424/9.1 |

FOREIGN PATENT DOCUMENTS

| | | |
|---|---|---|
| EP | 0740156 A1 | 10/1996 |
| JP | 11119270 A | 4/1999 |
| WO | WO 03/064991 A2 | 8/2003 |

OTHER PUBLICATIONS

Rinuy et al. [Second Harmonic Generation of Glucose Oxidase at the Air/Water Interface, Biophysial Journal, vol. 77, Dec. 1999, 3350-3355].*

(Continued)

*Primary Examiner* — Ann Lam
(74) *Attorney, Agent, or Firm* — Wilson Sonsini Goodrich & Rosati

(57) ABSTRACT

A nonlinear optical technique, such as second or third harmonic or sum or difference frequency generation, is used to detect binding interactions, or the degree or extent of binding, that comprise conformational change. In one aspect of the present invention, the nonlinear optical technique detects a conformational change in a probe due to target binding. In another aspect of the invention, the nonlinear optical technique screens candidate probes by detecting a conformational change due to a probe-target interaction. In another aspect of the invention, the nonlinear optical technique screens candidate modulators of a probe-target interaction by detecting a conformational change in the presence of the modulator.

8 Claims, 15 Drawing Sheets

OTHER PUBLICATIONS

Yang. SPEI vol. 2676, 290-296.*
Wang. J Phys Chem A, 1997, 101, 713-718.*
Theodossiou. Lasers Med Sci, 2002, 17: 34-41.*
Abbyad, P. et al. (2007). Journal of Physical Chemistry B 111, 8269.
Achari, A. et al. (1992). Biochemistry 31, 10449.
Agrawal et al., Tetrahedron Letters, 31: 1543-1546 (1990).
Antony T. et al. (2001) A molecular beacon strategy for the thermodynamic characterization of triplex DNA: triplex formation at the promoter region of cyclin DI. Biochemistry 40, 9387-9395.
Aplin et al., Analyt. Biochem. 113:144-148, 1981.
Arnold S F et al. (1999) Identification of bone morphogenetic proteins and their receptors in human breast cancer cell lines: importance of BMP2. Cytokine 11, 1031-1037.
Bakhtiar, R. "Peptide nucleic acids: deoxyribonucleic acid mimics with a peptide backbone" Biochem. Educ. 26 (1998) 277-280.
Ben-Oren et al. (Sep. 1996). "Infrared Nonlinear Optical Measurements of Membrane Potential on Photoreceptor Cells," *Biophysical Journal* 71:1616-1620.
Bentin, T. et al. "Triplexes involving PNA" Triple Helix Form. Oligonucleotides (1999) 245-255.
Berkovic, G. et al. (1989). Journal of the Optical Society of America B-Optical Physics 6, 205.
Bethea (Experimental technique of dc induced SHG in liquids: measurements of the nonlinearity of CH2I2, Applied Optics, 1975, 14, 1447.
Bieri et al., "Micropatterned immobilization of a G protein-coupled receptor and direct detection of G protein activation", Nature Biotechnology, 17, 1105 (1999).
Blanchard et al., Biosens. And Bioelectron. 11 (1996) 687.
Bonnet G. et al. (1998) Kinetics of conformational fluctuations in DNA hairpin-loops. Proc Natl Acad Sci USA 95, 8602-8606.
Bouevich, A. et al. "Probing Membrane Potential with Non-linear Optics," Biophys. J. 65, 672 (1993).
Brian et al., "Allogeneic Stimulation of Cyto-toxic T-cells by Supported Planar Membranes," PNAS-Biological Sciences 81(19): 6159-6163 (1984).
Brown et al. (1999). "exploring the new world of the genome with DNA microarrays," *Nature Genet.* 21 (Suppl.) (1999), 33-37.
Brown L J et al. (2000) Molecular beacons attached to glass beads fluoresce upon hybridisation to target DNA. Chemical Comm, 621-622.
Buchardt, et al. "Peptide nucleic acids and their potential applications in biotechnology" TIBTECH 11 (1993) 384-386.
Case-Green et al., Curr. Opin. Chem. Biol. 2 (1998), 404-410.
Cha, A. et al. (1999). "Atomic Scale Movement of the Voltage-Sensing Region in a Potassium Channel Measureed via Spectroscopy," Nature 402, 809.
Chen, C.K. et al. (1981). "Detection of Molecular Monolayers by Optical Second-Harmonic Generation," Physical Review Letters 46, 1010.
Chen W et al. (2000) Molecular beacons: a real-time polymerase chain reaction assay for detecting *Salmonella*. Anal Biochem 280, 166-172.
Cheung et al., "Making and reading microarrays", Nature Genetics (Suppl.), 1999, 21:15-19.
Chrisey et al., "Covalent Attachment of Synthetic DNA to Self-Assembled Monolayer Films", Nucleic Acids Research 24, 3031, (1996).
Clarke, M.L. et al. (2005). Journal of Physical Chemistry B 109, 22027.
Clays, K. et al., (Nov. 1993). "Nonlinear Optical Properties of Proteins Measured by Hyper-Rayleigh Scattering in Solution", Science, v. 262 (5138), 1419-22.
Clayton S J et al. (2000) K-ras point mutation detection in lung cancer: comparison of two approaches to somatic mutation detection using ARMS allele-specific amplification. Clin Chem 46, 1929-1938.
Cohen, B.E. et al. (May 31, 2002). "Probing Protein Electrostatics with a Synthetic Fluorescent Amino Acid," Science 296:1700-1703.
Cohen, B.E. et al. (Jan. 25, 2005). "A Fluorescent Probe Designed for Studying Protein Conformational Change," PNAS 102(4):965-970.
Corey "Peptide nucleic acids: expanding the scope of nucleic acid recognition" TIBTECH 15 (1997) 224-229.
Craighead et al., Appl. Phys. Lett. 37:653, 1980.
Craighead et al., J. Vac. Sci. Technol. 20:316, 1982.
De Baar M P et al. (2001) Single rapid real-time monitored isothermal RNA amplification assay for quantification of Human Immunodeficiency Virus Type 1 isolates from groups M, N, and O. J Clin Microbiol 39(4):1378-1384.
Delprincipe et al. (1999). "Two Photo and UV-Laser Flash Photlysis of CA Cage Dimethoynitrophenyl-EGTA-4," Cell Calcium 2585.
De Ronde A et al. (2001) Establishment of new transmissible and drug-sensitive Human Immunodeficiency Virus Type 1 wild types due to transmission of nucleoside analogue-resistant virus. J Virol 75, 595-602.
Derrick, J.P. et al. (1992). Nature 359, 752-754.
Devor E J (2001) Use of molecular beacons to verify that the serine hydroxymethyltransferase pseudogene SHMT-psl is unique to the order primates. Genome Biol 2. 6.1-6.5.
Ditlbacher, H. et al. (2001). "Electromagnetic Interaction of Fluorophores with Designed Two-Dimensional Silver Nanoparticle Arrays," *Applied Physics B* (73) 373-377.
Dracheva S et al. (2001) N-Methyl-D-Aspartic Acid Receptor expression in Dorsolateral Prefrontal Cortex of elderly patients with schizophrenia. American Journal of Psychiatry. 158, 1400-1410.
Dubertret et al. (2001) Single-mismatch detection using gold quenched fluorescent oligonucleotides. Nat Biotechnol 19, 365-370.
Dueholm, K. L. et al. "Chemistry, properties, and applications of PNA (Peptide Nucleic Acid)" New J. Chem. 21 (1997) 19-31.
Duggan et al., Nature Genet. 21 (Suppl.) (1999), 10-14.
Durand R, et al. (2000) Use of molecular beacons to detect an antifolate resistance-associated mutation in *Plasmodium falciparum*. Antimicrob Agents Chemother 44, 3461-3464.
Dworczak, R. et al. Phys. Chem. Chem. Phys., 2000, 2, 5057-5064.
Eldrup et al. "Peptide nucleic acids: potential as antisense and antigene drugs" Adv. Amino Acid Mimetics Peptidomimetics 2 (1999) 221-245.
El-Hajj H H et al (2001) Detection of rifampin resistance in *Mycobacterium tuberculosis* in a single tube with molecular beacons. J Clin Microbiol 39, 4131-4137.
Emory et al. (1998). "Screening and Enrichment of Metal Nanoparticles with Novel Optical Properties," *J. Phys. Chem. B* 102:493-497.
Emory et al. (1998). "Direct Observation of Size-Dependent Optical Enhancement in Single Metal Nanoparticles," *J. Am. Chem. Soc.* 120: 8009-8010.
England, P.M. (2004). "Unnatural amino acid mutagenesis: A precise tool for probing protein structure and function," Biochemistry 43(37): 11623-11629.
Eun A J C et al. (2000) Molecular beacons: a new approach to plant virus detection. Phytopathology 90, 269-275.
Fang X. et al. (2000) Using molecular beacons to probe molecular interactions between lactate dehydrogenase and single-stranded DNA. Anal Chem 72, 3280-3285.
Fejer et al., IEEE Journal of Quantum Electronics, v. 28, 1992, 2631.
Felderhof, B.U. et al. (1993). Journal of the Optical Society of America B-Optical Physics 10, 1824.
Feller, M.B.et al. (1991). Physical Review A 43(12), 6778-6792.
Finn et al. J. Chem. Phys., 1974, 60, 454-458.
Fodor et al., "Light-directed Spatially-addressable Parallel Chemical Synthesis," Science, 1991, 251, 767-773.
Fortin et al. (2001). "Use of Real-Time Poylmerase Chain Reaction and Molecular Beacons for the Detection of *Escherichia coli* O157:H7," *Analytical Biochemistry* 389:281-288.
Galletto et al., *J. Phys. Chem. B* 1999, 103, 8706-8710.
Gao. et al. (1997) Messenger RNA release from ribosomes during 5'-translational blockage by consecutive low-usage arginine but not leucine codons in *Escherichia coli.* Mol Microbiol 25, 707-716.
Georger et al.,( Apr. 30, 1992). "Coplanar Patterns of Self-assembled Monolayers for Selective Cell-adhesion and Outgrowth," Thin Solid Films 210 (1-2): 716-719.
Gether et al. (1995). "Fluorescent Labeling of Purified $\beta_2$ Adrenergic Receptor," Journal of Biological Chemistry 270(47): 28268-28275.
Ghanouni, P. et al. (2001). PNAS 98(11) 5997-6002.

Ghanouni et al. (2001). "Functionally Different Agonists Induce Distinct Conformations in the G Protein Coupling Domain of the B2 Adrenergic Receptor", Journal of Biological Chemistry, v.276, 24433-24436.
Giesendorf et al.(1998) Molecular beacons: a new approach for semiautomated mutation analysis. Clin Chem 44(3): 482-486.
Giusti et al., (1993). PCR Methods and Applications, 2: 223-227.
Glauner et al. (1999). "Spectroscopic Mapping of Voltage Sensor Movement in the *Shaker* Potassium Channel," Nature 402: 813-817.
Goddard, N. et al. (Sep. 2000). "sequence Dependent Rigidity of Single Stranded DNA," Physical Review Letters 85(11): 2400-2403.
Gold, B. et al. (2001). Molecular Microbiology 42(3):851-865.
Goh, M.C. et al. (1988). "Absolute Orientation of Water-Molecules at the Neat Water-Surface," Journal of Physical Chemistry 92, 5074-5075.
Gonzalez, E. et al. (1999). PNAS 96(21):12004-12009.
Greijer, A.E. (2002) "Multiplex real-time NASBA for monitoring expression dynamics of human cytomegalovirus encoded IE1 and pp 67 RNA" Journal of Clinical Virology 24:57-66.
Gronenborn, A.M. et al. (1991). Science 253, 657-661.
Groves, J. T. et al. "Micropatterning fluid bilayers on solid supports", Science, 1997, 275, 651-653.
Heil et al. (200). Molecular Genetics and Metabolism 71:511-519.
Heinz, T.F. (1991). "Second-Order Nonlinear Optical Effects at Surfaces and Interfaces," Elsevier: Amsterdam. Physical Review A 28(3):1883-1885.
Helmreich et al. (1996) Biochemica et Biophysica Acta 1286:285-322.
Helps C et al. (2001) Use of real-time quantitative PCR to detect *Chlamydophila felis* infection. J Clin Microbiol 39, 2675-2676.
Hoffmann, R., et al. "Low scale multiple array synthesis and DNA hybridization of peptide nucleic acids" Pept. Proc. Am. Pept. Symp., 15th (1999) 233-234.
Hoheisel, J. D. "Improved solid supports and spacer/linker systems for the synthesis of spatially addressable PNA libraries" Nucleosides Nucleotides 18 (1999) 1289-1291.
Huang, J. Y. et al. (1988) "Non-linear Optical Properties of Potential Sensitive Styryl Dyes", Biophysical J. 53, 665-670.
Hubbard, S.R. (1998). "Autoregulatory mechanisms in protein-tyrosine kinases," Journal of Biological Chemistry 273(20) 11987-11990.
Huse, M. et al. (2002). The conformational plasticity of protein kinases. Cell 109, 275-282.
deBaar et al. (2001). Journal of Clinical Microbiology 39(5):1895-1902.
Hyrup, B. et al. "Peptide Nucleic Acids (PNA): Synthesis, Properties and Potential Applications" Bioorg. Med. 4 (1996) 5-23.
International Search Report mailed on Feb. 10, 2006 for PCT Application No. PCT/US03/17807, 1 page.
Ishima, R. et al. (2000). Protein dynamics from NMR Nature Structural Biology vol. 7; pp. 740-743.
Jager et al. (Feb. 1996). Apply Phys Lett 68(9) 1183-1185.
Jordens J Z et al. (2000) Amplification with molecular beacon primers and reverse line blotting for the detection and typing of human papillomaviruses. J Virol Methods 89, 29-37.
Joshi, H. S. Metal-containing DNA hairpins as hybridization probes, Chem. Commun., 2001, 549-550.
Kaboev et al. (2000) PCR hot start using primers with the structure of molecular beacons (hairpin-like structure). Nucleic Acids 28(94), 2 pages.
Kamat et al. J. Phys. Chem. B, 1998, 102, 3123-3128.
Kemnitz, K. et al. (1986). "The Phase of 2nd-Harmonic Light Generated at an Interface and Its Relation to Absolute Molecular-Orientation," Chemical Physics Letters 131, 285-290.
Khatchatouriants, A. et al. Lewis, Z. Rothman, L. Loew and M. Treinin, "GFP is a Selective Non-Linear Optical Sensor of Electrophysiological Processes in *C. elegans*," Biophys. J. (in press, 2000) 2345-2352.
Klerks M M et al. (2001) Development of a multiplex AmpliDet RNA for the simultaneous detection of Potato leafroll virus and Potato virus Y in potato tubers. J Virol Methods 93, 115-125.
Kleinfeld et al., J. Neurosci. 8:4098-4120, 1988.

Knudsen et al. "Application of Peptide Nucleic Acid in Cancer Therapy" Anti-Cancer Drug 8 (1997) 113-118.
Kostrikis L G et al. (1998) Spectral genotyping of human alleles. Science 279, 1228-1229.
Kota, R. et al. (1999). Plant Molecular Biology Reporter 17:363-370.
Kriech, M.A. et al. (2005). "Using the intrinsic chirality of a molecule as a label-free probe to detect molecular adsorption to a surface by second harmonic generation," Applied Spectroscopy vol. 59; pp. 746-753.
Lamprecht et al., Appl. Phys. B, 1997, 64, 269-272.
Lanciotti R. S. et al. (2001) Nucleic acid sequence-based amplification assays for rapid detection of West Nile and St. Louis encephalitis viruses. J Clin Microbiol 39(12), 4506-4513.
Landry et al. Optics Express, v.5, 1999, 176-187.
Leone G. et al. (1998) Molecular beacon probes combined with amplification by NASBA enable homogeneous, real-time detection of RNA. Nucleic Acids Res 26, 2150-2155.
Levine et al. J. Chem. Phys., 1975, 63, 2666.
Levine et al. J. Chem. Phys., 1976, 65(5), 1989-1993.
Levine et al. J. Chem. Phys. 1977, 66, 1070-1074.
Levine et al. J. Chem. Phys. 1978,69(12): 5240-5245.
Lewin S R et al. (1999) Use of real-time PCR and molecular beacons to detect virus replication in human immunodeficiency virus type 1-infected individuals on prolonged effective antiretroviral therapy. J Virol 73, 6099-6103.
Lewis,A. et al. "Second Harmonic Generation of Biological Interfaces: Probing the Membrane Protein Bacteriorhodopsin and Imaging Membrane Potential Around GFP Molecules at Specific Sites in Neuronal Cells of *C. elegans*," Chemical Physics 245, 133-144 (1999).
Li J J. et al. (2000) Using molecular beacons as a sensitive fluorescence assay for enzymatic cleavage of single-stranded DNA. Nucleic Acids Res 28(11):e52.
Li J J et al. (2000) Molecular beacons: a novel approach to detect protein-DNA interactions. Angew Chem Int Ed 39(6): 1049-1052.
Li Q et al. (2000) Molecular beacon-based homogeneous fluorescence PCR assay for the diagnosis of infectious diseases. Analytical Sciences 16, 245-248.
Lindquist J N et al. (2000) Characterization of the interaction between alphaCP(2) and the 3'-untranslated region of collagen alpha1 (I) mRNA. Nucleic Acids Res 28, 4306-4316.
Liu et al., "Site-Directed fluorescent labeling of P-glycoprotein on cysteine residues in the nucleotide binding domains," Biochemistry 35, 11865-11873, (1996).
Liu J. et al. (2002) Real-time monitoring in vitro transcription using molecular beacons. Anal Biochem 300, 40-45.
Liu X et al. (1999) A fiber-optic evanescent wave DNA biosensor based on novel molecular beacons. Anal Chem 71, 5054-5059.
Liu, X. et al. Molecular Beacons for DNA Biosensors with Micrometer to Submicrometer Dimensions, Anal. Biochem., 283, 56-63, 2000.
Lopez et al., "Convenient Methods for Patterning the Adhesion of Mammalian Cells to Surfaces Using Self-Assembled Monolayers of Alkanethiolates on Gold," J. Am. Chem. Soc., 1993, 115, 5877-5878.
MacBeath et al. "Printing Proteins as Microarrays for High-Throughput Function Determination", Science 2000, 289, 1760-1763.
Majumdar, D.S. et al. (2007). Proceedings of the National Academy of Sciences of the United States of America 104, 12640-12645.
Manganelli R et al. (1999) Differential expression of 10 sigma factor genes in *Mycobacterium tuberculosis*. Mol Microbiol 31, 715-724.
Mannuzzu et al. (1996) Science 271, 213-216.
Marras et al., Multiplex detection of single-nucleotide variations using molecular beacons, S. A. E., Genetic Analysis: Biomolecular Engineering, 14 (1999), 151-156.
Marshall et al., "DNA chips—an array of possibilities," Nature Biotechnology 1998, 16(1), 27-31.
Martinson J J et al. (2000) Global distribution of the CCR2-641/CCR5-59653T HIV-1 disease-protective haplotype. Aids 14, 483-489.
Matsuo T. et al. (1998) In situ visualization of mRNA for basic fibroblast growth factor in living cells. Biochimica Biophysica Acta 1379, 178-184.

Matysiak, S. et al. "Improved solid supports and spacer/linker systems for the synthesis of spatially addressable PNA-libraries" Nucleosides Nucleotides 18 (1999) 1289-1291.
Mesmaeker, A. D. et al. "Backbone modifications in oligonucleotides and peptide nucleic acid systems" Curr. Opin. Struct. Biol. 5 (1995) 343-355.
McAllister et al., Am. J. Hum. Genet. 61 (Suppl.) (1997), 1387.
McConnell et al., J. Phys. Chem. B 2000, 104, 8925.
McKillip J L et al. (2000) Molecular beacon polymerase chain reaction detection of Escherichia coli 0157:H7 in milk. J Food Prot 63, 855-859.
Metzner K J et al. (2000) Effects of in vivo CD8(+) T cell depletion on virus replication in rhesus macaques immunized with a live, attenuated simian immunodeficiency virus vaccine. J Exp Med 191, 1921-1931.
Mrksich et al., Ann. Rev. Biophys. Biomol. Struct. 25:55-78, 1996.
Mullah B et al (1999) Efficient automated synthesis of molecular beacons. Nucleosides & Nucleotides 18, 1311-1312.
Nagar, B. et al. (2002). Crystal structures of the kinase domain of c-Abl in complex with the small molecule inhibitors PD173955 and imatinib (STI-571). Cancer Research 62, 4236-4243.
Nazarenko I A. et al. (1997) A closed tube format for amplification and detection of DNA based on energy transfer. Nucleic Acids Res 25, 2516-2521.
Nelson et al., Nucleic Acids Research, 17: 7187-7194 (1989).
Nie et al. Science, 1997, 75, 1102-1106.
Nielsen, et al. "Peptide nucleic acids-(PNA): Oligonucleotide analogues with a polyamide backbone" Antisense Research and Applications (1992) 363-372.
Nielsen, et al. "Peptide nucleic acids (PNAs): Potential Antisense and Anti-gene Agents." Anti-Cancer Drug Design 8 (1993) 53-63.
Nielsen, P. E., Egholm, M. and Buchardt, O. "Peptide Nucleic Acid (PNA). A DNA mimic with a peptide backbone" Bioconjugate Chemistry 5 (1994) 3-7.
Nielsen, P. E. "DNA analogues with nonphosphodiester backbones"Annu Rev.Biophys.Biomol.Struct. 24 (1995) 167-183.
Nielsen, P. E. et al. "Peptide nucleic acid (PNA), a new molecular tool." In Molecular Biology: Current Innovations and Future Trends, Part2. Horizon Scientific Press, (1995) 73-89.
Nielsen "Peptide nucleic acid (PNA): A lead for gene therapeutic drugs" Antisense Therapeutics 4 (1996) 76-84.
Nielsen, P. E. "Design of Sequence-Specific DNA-Binding Ligands" Chem. Eur. J. 3 (1997) 505-508.
Nielsen, P. E. and Haaima, G. "Peptide nucleic acid (PNA). A DNA mimic with a pseudopeptide backbone" Chem. Soc. Rev. (1997) 73-78.
Nielsen, P. E. "Structural and Biological Properties of Peptide Nucleic Acid (Pna)" Pure & Applied Chemistry 70 (1998) 105-110.
Nielsen "Peptide Nucleic Acids" Science and Medicine (1998) 48-55 Planning.
Nielsen, P. E. "Sequence-specific recognition of double-stranded DNA by peptide nucleic acids" Advances in DNA Sequence-Specific Agents 3 (1998) 267-278.
Nielsen "Antisense Properties of Peptide Nucleic Acid" Handbook of Experimental Pharmacology 131 (1998) 545-560.
Nielsen, P. E. "Applications of peptide nucleic acids" Curr Opin Biotechnol 10 (1999) 71-75.
Noble, et al. "Impact on Biophysical Parameters on the Biological Assessment of Peptide Nucleic Acids, Antisense Inhibitors of Gene Expression" Drug.Develop.Res. 34 (1995) 184-195.
Noble, M.E.M. et al. (2004). "Protein kinase inhibitors: Insights into drug design from structure," Science 303, 1800-1805.
Novak et al. "Assembly of Phenylacetylene-Bridged Silver and Gold Nanoparticle Arrays", J. Am. Chem. Soc., 2000, 122, 3979-3980.
Novak et al., "Nonlinear Optical Properties of Molecularly Bridged Gold Nanoparticle Arrays", J. Am. Chem. Soc. 2000, 122, 12029-12030.
Ong, S.W. et al. (1992). Chemical Physics Letters 191, 327-335.
Ortiz E et al (1998) PNA molecular beacons for rapid detection of PCR amplicons. Mol Cell Probes 12, 219-226.
Orum, H., Kessler, C. and Koch, T. "Peptide Nucleic Acid" Nucleic Acid Amplification Technologies: Application to Disease Diagnostics (1997) 29-48.

Oudar et al. J. Chem. Phys., 1977, 66, 2664-2668.
Park Set al. (2000) Rapid identification of Candida dubliniensis using a species-specific molecular beacon. J Clin Microbiol 38(8): 2829-2836.
Paszti, Z. et al. (2004). Journal of Physical Chemistry B 108, 7779.
Peleg et al., "Nonlinear optical measurement of membrane potential around single molecules at selected cellular sites," Proc. Natl. Acad. Sci. V. 96, (1999), 6700-6704.
Piatek A S et al. (1998) Molecular beacon sequence analysis for detecting drug resistance in Mycobacterium tuberculosis. Nat Biotechnol 16, 359-363.
Piatek A S et al. (2000) Genotypic analysis of Mycobacterium tuberculosis in two distinct populations using molecular beacons: implications for rapid susceptibility testing. Antimicrob Agents Chemother 44, 103-110.
Pierce K. et al. (2000) Real-time PCR using molecular beacons for accurate detection of the Y chromosome in single human blastomeres. Mol Hum Reprod 6, 1155-1164.
Poddar S. et al. (2000) Symmetric vs asymmetric PCR and molecular beacon probe in the detection of a target gene of adenovirus. Mol Cell Probes 14, 25-32.
Polizzi, M.A. et al. (2004). Journal of the American Chemical Society 126, 5001-5007.
Ramsay, "DNA chips—states-of-the-art," Nature Biotechnology 1998, 16(1), 40-44.
Rhee, J.T. et al. (Jun. 1999). Journal of Clinical Microbiology 37(6) 1764-1770.
Rinuy et al. Dec. 1999. "Second Harmonic Generation of Glucose Oxidase at the Air/Water Interface," Biophysical Journal, 77:3350-3355.
Rodriguez, E.A. et al. (2006). "In vivo incorporation of multiple unnatural amino acids through nonsense and frameshift suppression," Proceedings of the National Academy of Sciences of the United States of America 103, 8650-8655.
Saha B K. et al. (2001) Quantitation of HIV-1 by real-time PCR with a unique fluorogenic probe. J Virol Methods 93, 33-42.
Salafsky, J.S. et al. (2000). Journal of Physical Chemistry B 104, 7752-7755.
Salafsky, J.S. (2006). Journal of Chemical Physics 125, 074701.
Salafsky, J.S. et al. (2000). Chemical Physics Letters 319: 435-439.
Schena et al., Science 270 (1995), 467.
Schofield P. et al. (1997) Molecular beacons: trial of a fluorescence based solution hybridization technique for ecological studies with ruminal bacteria. Appl Environ Microbiol 63, 1143-1147.
Sebti, A. et al. (Apr. 2001). "Candida dubliniensis at a Cancer Center," CID 32:1034-1038.
Salafsky, J.S. (2007). "Second-harmonic generation for studying structural motion of biological molecules in real time and space," Phys Chem 9:5704-5711.
Gupta, K.C. et al. (1991). Nucleic Acids Research, 19: 3019-3025.
Samanta, A. et al. (2000). Journal of Physical Chemistry A 104, 8972-8975.
Sauer-Eriksson, A.E. et al. (1995). Structure 3, 265-278.
Schena et al., Science 270 (1995), 467-469.
Schofield P. et al. (1997) Molecular beacons: trial of a fluorescence based solution hybridization technique for ecological studies with ruminal bacteria. Appl Environ Microbiol 63(3) 1143-1147.
Seeliger, M.A. (2005). Protein Science 14:3135-3139.
Shih, I-M. et al. (Feb. 2001). Cancer Research 61: 818-822.
Sicheri, F. (Feb. 1997). "Crystal structure of the Src family tyrosine kinase Hck," Nature 385: 602-609.
Sicheri, F. et al. (1997). "Structures of Src-family tyrosine kinases," Current Opinion in Structural Biology 7, 777-785.
Singhvi et al., Science 264:696-698, 1994.
Smit M L et al. (2001) Semiautomated DNA mutation analysis using a robotic workstation and molecular beacons. Clin Chem 47, 739-744.
Sokol D L. et al. (1998) Real time detection of DNA.RNA hybridization in living cells. Proc Natl Acad Sci USA 95, 11538-11543.
Sonnichsen et al., Appl. Phys. Lett., 2000, 77(19): 2949-2951.
Spargo, B. J. (Nov. 1994). Proc Natl Acad Sci 91:11070-11074.
Srivastava, A. et al. "Kinetics of molecular transport across a liposome bilayer," Chem. Phys. Lett. 292 (3): 345-351 (1998).

Singer, K.D. (Oct. 1981). J Chem Phys 75(7):3572-3580.
Steemers F J et al. (2000) Screening unlabeled DNA targets with randomly ordered fiber-optic gene arrays. Nat Biotechnol 18, 91-94.
Steuerwald N et al. (1999) Analysis of gene expression in single oocytes and embryos by real-time rapid cycle fluorescence monitored RT-PCR. Mol Hum Reprod 5, 1034-1039.
Strouse R J. et al. (2000) Using molecular beacons to quantify low levels of type I endonuclease activity. Biopharm 13, 40-47.
Suh et al. Proc. SPIE 382:199, 1983.
Summerer, D. et al. (2006). "A genetically encoded fluorescent amino acid," Proceedings of the National Academy of Sciences of the United States of America 103, 9785-9789.
Szuhai K et al. (2001) Simultaneous A8344G heteroplasmy and mitochondrial DNA copy number quantification in myoclonus epilepsy and ragged-red fibers (MERRF) syndrome by a multiplex molecular beacon based real-time fluorescence PCR. Nucleic Acids Res 29(3) E13.
Szuhai K et al. (2001) A novel strategy for human papillomavirus detection and genotyping with SybrGreen and molecular beacon polymerase chain reaction. Am J Pathol 159(5):1651-1660.
Tan W. et al. (2000) Molecular beacons: a novel DNA probe for nucleic acid and protein studies. Chemistry 6, 1107-1 1111.
Tapp I et al (2000) Homogeneous scoring of single-nucleotide polymorphisms: comparison of the 5'-nuclease TaqMan assay and molecular beacon probes. Biotechniques 28, 732-738.
Thelwell N. et al. (2000) Mode of action and application of scorpion primers to mutation detection. Nucleic Acids Res 28, 3752-3761.
Thomas, G.J.J. (1999). Annual Review of Biophysics and Biomolecular Structure vol. 28; pp. 1-27.
Tung, C-H et al. (2000). Cancer Res 60:4953-4958.
Turcatti et al., "Probing the Structure and Function of the Tachykinin Neurokinin-Receptor through Biosynthetic incorporation of fluorescent amino acids at specific sites," J. Biol. Chem. 271, 19991-19998, (1996).
Bonnet, G. (May 1999). Thermodynamic basis of the enhanced specificity of structured DNA probes. Proc Natl Acad Sci USA 96, 6171-6176.
Tyagi et al., Molecular Beacons: Probes that Fluoresce upon Hybridization, Nature Biotechnology, v. 14, 1996, 303-308.
Tyagi S. et al. (1998) Multicolor molecular beacons for allele discrimination. Nat Biotechnol 16, 49-53.
Tyagi et al. Wavelength-shifting molecular beacons, Nature Biotechnology, v. 18, 2000, 1191-1196.
Uhlmann, E. "Peptide nucleic acids (PNA) and PNA-DNA chimeras: from high binding affinity towards biological function" Biol Chem 379 (1998) 1045-52.
Uhlmann, E. et al. "PNA: Synthetic polyamide nucleic acids with unusual binding properties" Angewandte Chemie-International Edition 37 (1998) 2797-2823.
Valentin, A. (2000). Virology 269:294-304.
Van Beuningen R. et al (2001) Development of a high-throughput detection system for HIV-1 using real-time NASBA based on molecular beacons. Proceedings—SPIE the International Society for Optical Engineering. 4264, 66-71.
Van Schie R C. et al. (2000) Semiautomated clone verification by real-time PCR using molecular beacons. Biotechniques 29, 1296-1306.
Vance, F W et al., Enormous Hyper-Rayleigh Scattering from Nanocrystalline Gold Particle Suspensions, J. Phys. Chem. B 102:10091-93 (1999).
Vet J A. et al. (1999) Multiplex detection of four pathogenic retroviruses using molecular beacons. Proc Natl Acad Sci USA 96, 6394-6399.
Vogelstein B et al. (1999) Digital PCR. Proc Natl Acad Sci USA 96, 9236 9241.
Wang "DNA biosensors based on peptide nucleic acid (PNA) recognition layers. A review" Biosens Bioelectron 13 (1998) 757-62.
Watson et al. Technology for microarray analysis of gene expression, Current Opinion in Biotechnology, 9, 609-614, 1998.
Weber, G. et al. (1979). Biochemistry 18, 3075-3078.
Doring, K. et al. (2000). Protein Science 9:2246-2250.
Weisz, K. "Polyamides as artificial regulators of gene expression" Angew. Chem. Int. Ed. Eng 36 (1997) 2592-2594.
Weljie, A.M. et al. (2003). "Protein conformational changes studied by diffusion NMR spectroscopy: Application to helix-loop-helix calcium binding proteins," Protein Science vol. 12: 228-235.
Whitcombe D. et al. (1999) Detection of PCR products using self-probing amplicons and fluorescence. Nat Biotechnol 17, 804-807.
Wittung, P., Nielsen, P. and Norden, B. "Recognition of double-stranded DNA by peptide nucleic acid" Nucleosid. Nucleotid. 16 (1997) 599-602.
Xiao G et al. (2000) A DNA damage signal is required for p53 to activate gadd45. Cancer Res 60, 1711-1719.
Xie, J.M. et al. (2006). "Innovation: A chemical toolkit for proteins—an expanded genetic code," Nature Reviews Molecular Cell Biology 7, 775-782.
Xu, W.Q. et al. (1997). "Three-dimensional structure of the tyrosine kinase c-Src," Nature 385, 595-602.
Xu, W. (May 1999). Molecular Cell 3:629-638.
Yamamoto R. et al. (2000) Molecular beacon aptamer fluoresces in the presence of Tat protein of HIV-1. Genes Cells 5, 389-396.
Yates, S. et al. (2001). J Clin Microbiol 39(10): 3656-3665.
Ying L. et al. (2001) Two-state model of conformational fluctuation in a DNA hairpin-loop. Chemical Physics Letters 334, 145-150.
Zhang P. et al. (2001) Design of a molecular beacon DNA probe with two fluorophores. Angew. Chem. Int. Ed. 40, 402-405.
Zhang, B.L. et al. (1999). J Exp Med 190(5):725-732.
Zimdars, D. et al. (2001). "Static and Dynamic Solvation at the Air/Water Interface," Journal of Physical Chemistry B vol. 105; pp. 3993-4002.
Zuckerman et al., Nucleic Acids Research, 15: 5305-5321 (1987).
Lazurkin, Y.S. (1999) Molecular Biology 33(1):79-83.
Levicky et al. "Using Self-Assembly to Control the Structure of DNA Monolayers on Gold: A Neutron Reflectivity Study," Journal of the American Chemical Society 120: 9787-9792 (1998).
Oudar, J. L. (1977). The Journal of Chemical Physics 67(2): 446-457.
Sigal, G. B. (1996). Anal Chem 68:490-497.
Sproat, B. S. (1987). Nucleic Acid Research 15(12):4837-4848.
Vance, F.W. (1998). J Phys Chem 102:10091-10093.
U.S. Appl. No. 60/350,322, filed Jan. 17, 2002, Salafsky.
Boyd, et al. Local-field enhancement on rough surfaces with the use of optical 2nd-harmonic generation. Phys. Rev. B 1984; 30:519-526.
Campagnola, et al. High-resolution nonlinear optical imaging of live cells by second harmonic generation. Biophys J. Dec. 1999;77(6):3341-9.
Cha, et al. Characterizing voltage-dependent conformational changes in the Shaker K+ channel with fluorescence. Neuron. Nov. 1997;19(5):1127-40.
Conboy, et al. Studies of Alkane/water interfaces by total internal reflection second harmonic generation. J. Phys. Chem. 1994; 98:9688-9698.
Ditcham, et al. An immunosensor with potential for the detection of viral antigens in body fluids, based on surface second harmonic generation. Biosens Bioelectron. May 2001;16(3):221-4.
Eisenthal. Photochemistry and photophysics of liquid interfaces by second harmonic spectroscopy. J. Phys. Chem. 1996; 100:12997-13006.
European search report Jan. 24, 2008 for EP Application No. 03736879.2.
European search report May 18, 2005 for EP Application No. 01995403.1.
European search report Dec. 3, 2004 for EP Application No. 01957166.0.
Fittinghoff. Collinear type II second-harmonic-generation frequency-resolved optical gating for use with high-numerical-aperature objectives, 1998, Opt Left, 23(13), 1046-1048.
Hicks. Studies of Chemical Processes in Liquids Using Short Laser Pulses: 1. The Dynamics of Photoisomerization of Polar Molecules in Solution 2. Studies of Liquid Surfaces by Second Harmonic Generation Ph.D. dissertation, Columbia University. 1986.
International search report dated Jan. 22, 2002 for PCT/US2001/022411.
International search report dated Feb. 10, 2006 for PCT/US2003/017807.
International search report dated Mar. 23, 2006 for PCT/US2002/022681.

International search report dated Apr. 20, 2012 for PCT/US2012/030010.
International search report dated May 1, 2002 for PCT/US2001/046932.
International search report dated Oct. 20, 2001 for PCT/US2001/022412.
International search report dated Dec. 27, 2001 for PCT/US2001/022441.
Levine, et al. Absolute signs of hyperpolarizabilities in the liquid state. J. Chem. Phys. 1974; 60(10)3856-3858.
Levine. Conjugated electron contributions to the second order hyperpolarizability of substituted benzene molecules J. Chem. Phys. 1975; 63:115-117.
Milosevic, et al. Extreme-ultraviolet harmonic generation near 13 nm with a two-color elliptically polarized laser field, 2000, Opt Lett, 25(20), 1532-1534.
Moreaux, et al. Membrane imaging by second harmonic generation microscopy. Journal of Optical Society of America B: Optical Physics. 2000; 17(10):1685-1694.
Office action dated Jan. 14, 2013 for U.S. Appl. No. 12/535,631.
Office action dated Feb. 7, 2002 for U.S. Appl. No. 09/731,366.
Office action dated Feb. 23, 2004 for U.S. Appl. No. 09/731,366.
Office action dated Mar. 24, 2008 for U.S. Appl. No. 11/327,199.
Office action dated Mar. 30, 2009 for U.S. Appl. No. 11/327,199.
Office action dated Apr. 3, 2012 for U.S. Appl. No. 12/535,631.
Office action dated Apr. 21, 2004 for U.S. Appl. No. 09/907,038.
Office action dated May 8, 2002 for U.S. Appl. No. 09/907,035.
Office action dated Jun. 18, 2007 for U.S. Appl. No. 11/327,199.
Office action dated Aug. 25, 2003 for U.S. Appl. No. 09/907,035.
Office action dated Sep. 10, 2004 for U.S. Appl. No. 09/731,366.
Office action dated Sep. 20, 2005 for U.S. Appl. No. 10/467,098.
Office action dated Oct. 23, 2003 for U.S. Appl. No. 09/731,366.
Office action dated Oct. 28, 2002 for U.S. Appl. No. 09/731,366.
Office action dated Nov. 3, 2006 for U.S. Appl. No. 10/970,754.
Office action dated Nov. 20, 2002 for U.S. Appl. No. 09/907,035.
Salafsky, et al. SHG labels for detection of molecules by second harmonic generation. Chemical Physics Letters. 2001; 342:485-491.
Salafsky, et al.. Architecture and function of membrane proteins in planar supported bilayers: A study with photosynthetic reaction centers' Biochemistry. 1996; 35(47):14773-14781.
Shen. The Principles of Nonlinear Optics, John Wiley & Sons, New York. 1984.
Shen.. Surface properties probed by second-harmonic and sum-frequency generation. Nature. 1989; 337: 20 519-525.
Theodossiou, et al.Thermally Induced Irreversible Conformational Changes in Collagen Probed by Optical Second Harmonic Generation and Laser-induced Fluorescence, 2002; 17:34-41.
Wang, et al. In situ, nonlinear optical probe of Surfactant Adsorption on the Surface of Microparticles in Colloids. Langmuir 2000, 16, 2475-2481.
Wang, et al. Polarity of liquid interfaces by second harmonic generation spectroscopy, 1997, J Phys Chem A, 101, 713-718.
Yang, et al. Surface second harmonic generation (SSHG)—a new scheme for immunoassay. Proceedings of the SPIE. 1996; 2676:290-296. http://dx.doi.org/10.1117/12.238808.

* cited by examiner

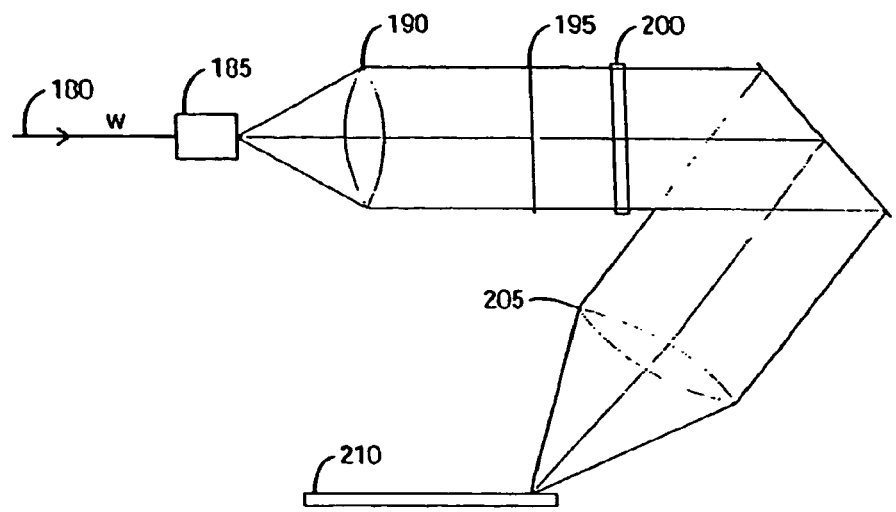
FIG. 6
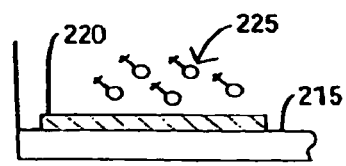
FIG. 7B
FIG. 7A

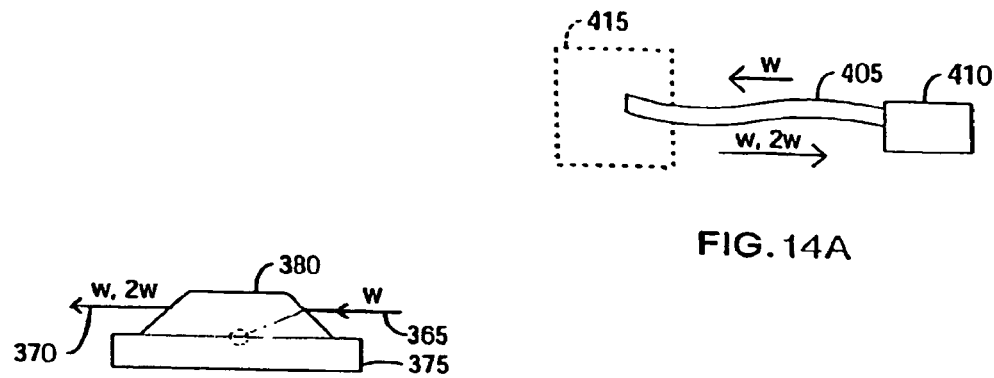
FIG. 13A
FIG. 14A
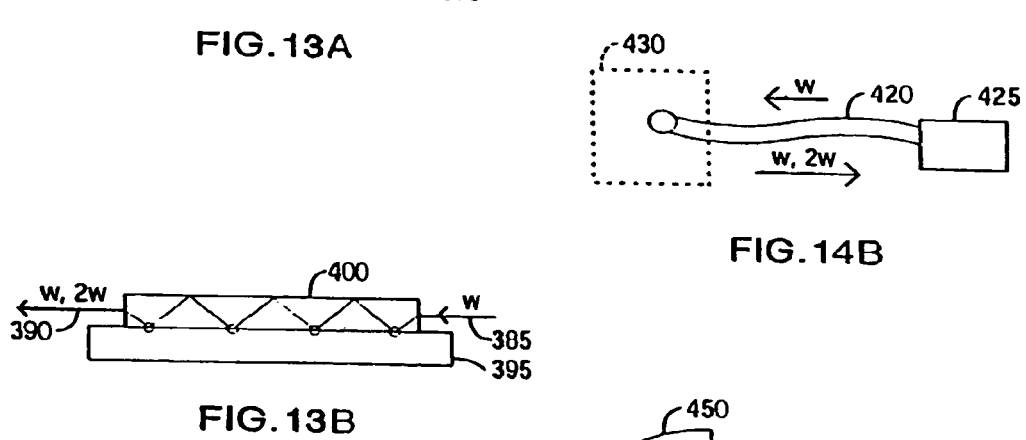
FIG. 13B
FIG. 14B
FIG. 14C

Target 1: 5'-AAAAAAAAAAAAAAACTCGC-3'
Target 2: 5'-GAAAAAAAAAAAAAAAA-3'
Target 3: 5'-GAAAAAAACAAAAAAA-3'
Target 4: 5'-CTACCTACAGTACCAAGCTT(X)$_{30}$
         TTACTCGAGGGATCCTAGTC-3'

METHOD USING A NONLINEAR OPTICAL TECHNIQUE FOR DETECTION OF INTERACTIONS INVOLVING A CONFORMATIONAL CHANGE

CROSS REFERENCE TO RELATED APPLICATIONS

This application is a continuation application of U.S. patent application Ser. No. 11/327,199, filed on Jan. 5, 2006, now abandoned, which is a continuation of U.S. patent application Ser. No. 10/164,915, filed on Jun. 6, 2002, now abandoned, which claims the benefit of U.S. Provisional Application No. 60/362,003, filed on Mar. 5, 2002; U.S. Provisional Application No. 60/354,679, filed on Feb. 6, 2002; U.S. Provisional Application No. 60/354,668, filed on Feb. 6, 2002; and U.S. Provisional Application No. 60/351,879, filed on Jan. 24, 2002, each of which is incorporated herein by reference in its entirety.

FIELD OF THE INVENTION

The present invention relates to a method for detecting interactions between biological components using a surface-selective nonlinear optical technique. In one aspect of the present invention this relates to detection of binding between probes and targets that results in a conformational change.

BACKGROUND OF THE INVENTION

Detection of Binding

Detecting and quantifying interactions such as binding between biomolecules is of central interest in modern molecular biology and medicine. Ligand and drug binding to molecules is an important theme in modern biology, medicine and drug development. Binding reactions between biological components often result in a conformational or dipole moment (or induced dipole moment) change. Conformational change (a change in orientation or position of a molecule or subpart(s) of a molecule) is an essential feature of signaling in many systems. A technique for detecting activation of a signal transducer (e.g., a receptor in a membrane), through a direct measure of conformational change or change in dipole moment, would be of value in basic research and drug discovery. For example, high-throughput drug screening for potential agonists or antagonists of a receptor can be carried out using the present invention as a method for detection of whether potential agonists or antagonists induce a conformational change—indicative of binding and activation of a receptor. Because the conformational change is a direct indicator of receptor activation, it is an excellent means of screening for drugs; current techniques often rely on indirect measures of activation such as changes in fluorescence intensity that are concomitant with changes in $Ca^{2+}$ ion concentration, which in turn is caused by the receptor activation. Current techniques that directly measure activation, such as patch-clamping techniques with an ion channel protein, are not amenable to high-throughput scaleup and require a skilled technician to operate, resulting in higher cost to the user.

Fluorescence-based or surface plasmon-based detection are used to detect binding interactions, with varying success and efficiency. Problems using fluorescence include the presence of a natural fluorescent background in many (non-labeled) biological samples as well as photobleaching. Detection of orientational changes accompanying target binding is difficult to do using fluorescence as the technique is not very sensitive to label orientation: fluorescence polarization, not being a coherent technique, is sensitive to rotational motion during the fluorescence lifetime that makes it difficult to assign small measured changes in a particular polarization direction to conformational changes (rather than due to rotational motion). It is also difficult to separate small changes in probe orientation from the large fluorescent background that may be present in many biological samples. Furthermore, it is often not trivial to separate a signal indicative of binding from one indicative of a receptor activation using fluorescence; for example, fluorescently tagged targets are tested for their ability to bind to a given receptor using fluorescence polarization—but binding of a target to a surface such as a cell surface can occur non-specifically such that the target does not specifically bind to the receptor of interest, yet can still give a signal indicative of said binding; direct detection of conformational change as an indicator of receptor activation is a more direct means of assaying for activation. Wavelength-based changes due to changes in the microenvironment of the label as a result of conformational change can be followed, but not all conformational changes lead to a change in microenvironment and it may be difficult to assign relative changes due to microenvironment to the degree of conformational change that actually occurs. Examples of fluorescent-based prior art to detect conformational changes in proteins include the following: Mannuzzu et al. (1996) Science 271, 213-216 describe the direct physical measure of conformational rearrangement underlying potassium channel gating using an fluorescently tagged channel protein. Gether et al., "Fluorescent labeling of purified P2 adrenergic receptor," J. Biol. Chem. 270, 28628-28275 (1995), describe the fluorescent labeling of soluble purified 02 adrenergic receptor to detect ligand-specific conformational changes. Turcatti et al., "Probing the Structure and Function of the Tachykinin Neurokinin-Receptor through Biosynthetic incorporation of fluorescent amino acids at specific sites," J. Biol. Chem. 271, 19991-19998, (1996), describe the incorporation of non-natural fluorescent amino acids into a receptor to monitor ligand binding. Liu et al., "Site-Directed fluorescent labeling of P-glycoprotein on cysteine residues in the nucleotide binding domains," Biochemistry 35, 11865-11873, (1996), describe fluorescent labeling of soluble purified P-glycoprotein to detect ligand binding.

Fluorescence has also been used to detect binding of targets to ion channel receptors when the binding leads to a change in transmembrane potential in cells. The transmembrane potential change (e.g., a depolarization) leads to a change in the intensity, lifetime, wavelength, etc. of the fluorescent or non-linear-active label in the membrane. Apart from various problems in the detection itself—concerning photobleaching, artifacts and background noise, these methods only provide indirect assays for the probe-target binding. For example, it is possible that a given target binds to ion channel probes and the ion channels are activated, but that this does not lead to a change in transmembrane potential, either for natural reasons or because there are problems in the cells in the normal mechanism for producing the change in transmembrane potential. It is desirable therefore to have a direct, optical means of detecting probe-target binding reactions in cases where the binding reaction results in a change in orientation or conformation of the probe.

Molecular Beacons

Molecular beacons are also used for the detection of binding interactions. A molecular beacon (MB) probe is well known in the art as a hairpin-loop, single-stranded oligonucleotide comprising a probe sequence embedded within complementary sequences that form a hairpin stem. The loop portion of the molecule can form a double-stranded DNA in the presence of complementary nucleic acid. A fluorophore is covalently attached to one end of the oligonucleotide, and a nonfluorescent quencher is covalently attached to the other end. There are typically five to eight bases at each side of the two ends of the beacon which are complementary to each other. The stem keeps these two moieties in close proximity to each other, causing the fluorescence of the fluorophore to be quenched by energy transfer. When the beacon binds to its target, the rigidity of the probe-target duplex forces the stem to unwind, which causes the separation of the fluorophore and the quencher and the restoration of fluorescence. This permits the detection of probe-target hybrids in the presence of unhybridized probes.

The following (and references therein) describe the production, design and use of molecular beacons (MBs) in the fluorescence literature:

Sequence Dependent Rigidity of Single Stranded DNA, Phys. Rev. Lett., 85, 2400 No. 11, Noel L. Goddard, 1 Gregoire Bonnet, 1 Oleg Krichevsky, 2 and Albert Libchaber, 2000.

Metal-containing DNA hairpins as hybridization probes, H. S. Joshi and Y. Tor, Chem. Commun., 2001, 549-550.

Spectral Genotyping of Human Alleles, L. G. Kostrikis, S. Tyagi, M. M. Mhlanga, D. D. Ho, F. R. Kramer, Science v. 279, February 1998.

Molecular Beacons for DNA Biosensors with Micrometer to Submicrometer Dimensions, X. Liu, W. Farmerie, S. Schuster, W. Tan, Anal. Biochem., 283, 56-63, 2000.

Multiplex detection of single-nucleotide variations using molecular beacons, S. A. E. Marras, F. R. Kramer, S. Tyagi, Genetic Analysis: Biomolecular Engineering, 14 (1999), 151-156.

Screening unlabeled DNA targets with randomly ordered fiber-optic gene arrays, F. J. Steemers, J. A. Ferguson, D. R. Walt, Nature Biotechnology, v. 18, 2000, 91.

Wavelength-shifting molecular beacons, S. Tyagi, S. A. E. Marras, F. R. Kramer, Nature Biotechnology, v. 18, 2000, 1191.

Molecular Beacons: Probes that Fluoresce upon Hybridization, S. Tyagi, F. R. Kramer, Nature Biotechnology, v. 14, 1996, 303.

Technology for microarray analysis of gene expression, A. Watson, A. Mazumder, M. Stewar, S. Balasubramanian, Current Opinion in Biotechnology, 9, 609-614, 1998.

Design of a Molecular Beacon DNA Probe with Two Fluorophores, P. Zhang, T. Beck, W. Tan, Angew. Chem. Int. Ed. 40, 402, 2001

Bonnet G, Tyagi S, Libchaber A, and Kramer F R (1999) Thermodynamic basis of the enhanced specificity of structured DNA probes. Proc Natl Acad Sci USA 96, 6171-6176.

Dubertret B, Calame M, and Libchaber A (2001) Single-mismatch detection using gold-quenched fluorescent oligonucleotides. Nat Biotechnol 19, 365-370.

Marras S A E, Kramer F R, and Tyagi S (1999) Multiplex detection of single-nucleotide variations using molecular beacons. Genet Anal 14, 151-156.

Mullah B and Livak K (1999) Efficient automated synthesis of molecular beacons. Nucleosides & Nucleotides 18, 1311-1312.

Ortiz E, Estrada G, and Lizardi P M (1998) PNA molecular beacons for rapid detection of PCR amplicons. Mol Cell Probes 12, 219-226.

Tyagi S, Marras S A E, and Kramer F R (2000) Wavelength-shifting molecular beacons. Nat Biotechnol 18, 1191-1196.

Tyagi S, Bratu D P, and Kramer F R (1998) Multicolor molecular beacons for allele discrimination. Nat Biotechnol 16, 49-53.

Tyagi S and Kramer F R (1996) Molecular beacons: probes that fluoresce upon hybridization. Nat Biotechnol 14, 303-308.

El-Hajj H H, Marras S A, Tyagi S, Kramer F R, and Alland D (2001) Detection of rifampin resistance in *Mycobacterium tuberculosis* in a single tube with molecular beacons. J Clin Microbiol 39, 4131-4137.

Giesendorf B A, Vet J A, Tyagi S, Mensink E J, Trijbels F J, and Blom H J (1998) Molecular beacons: a new approach for semiautomated mutation analysis. Clin Chem 44, 482-486.

Kostrikis L G, Tyagi S, Mhlanga M M, Ho D D, and Kramer F R (1998) Spectral genotyping of human alleles. Science 279, 1228-1229.

Piatek A S, Telenti A, Murray M R, El-Hajj H, Jacobs W R, Jr., Kramer F R, and Alland D (2000) Genotypic analysis of *Mycobacterium tuberculosis* in two distinct populations using molecular beacons: implications for rapid susceptibility testing. Antimicrob Agents Chemother 44, 103-110.

Piatek A S, Tyagi S, Pol A C, Telenti A, Miller L P, Kramer F R, and Alland D (1998) Molecular beacon sequence analysis for detecting drug resistance in *Mycobacterium tuberculosis*. Nat Biotechnol 16, 359-363.

Rhee J T, Piatek A S, Small P M, Harris L M, Chaparro S V, Kramer F R, and Alland D (1999) Molecular epidemiologic evaluation of transmissibility and virulence of *Mycobacterium tuberculosis*. J Clin Microbiol 37, 1764-1770.

Szuhai K, Ouweland J M, Dirks R W, Lemaitre M, Truffert J C, Janssen G M, Tanke H J, Holme E, Maassen J A, and Raap A K (2001) Simultaneous A8344G heteroplasmy and mitochondrial DNA copy number quantification in myoclonus epilepsy and ragged-red fibers (MERRF) syndrome by a multiplex molecular beacon based real-time fluorescence PCR. Nucleic Acids Res 29, E13.

Szuhai K, Sandhaus E, Kolkrnan-Uljee S M, Lemaitre M, Truffert J C, Dirks R W, Tanke H J, Fleuren G J, Schuuring E, and Raap A K (2001) A novel strategy for human papillomavirus detection and genotyping with SybrGreen and molecular beacon polymerase chain reaction. Am J Pathol 159, 1651-1660.

Tapp I, Malmberg L, Rennel E, Wik M, and Syvanen A C (2000) Homogeneous scoring of single-nucleotide polymorphisms: comparison of the 5'-nuclease TaqMan assay and molecular beacon probes. Biotechniques 28, 732-738.

Vogelstein B and Kinzler K W (1999) Digital PCR. Proc Natl Acad Sci USA 96, 9236-9241.

Arnold S F, Tims E, and McGrath B E (1999) Identification of bone morphogenetic proteins and their receptors in human breast cancer cell lines: importance of BMP2. Cytokine 11, 1031-1037.

Chen W, Martinez G, and Mulchandani A (2000) Molecular beacons: a real-time polymerase chain reaction assay for detecting *Salmonella*. Anal Biochem 280, 166-172.

Clayton S J, Scott F M, Walker J, Callaghan K, Hague K, Liloglou T, Xinarianos G, Shawcross S, Ceuppens P, Field J K, and Fox J C (2000) K-ras point mutation detection in lung cancer: comparison of two approaches to somatic mutation detection using ARMS allele-specific amplification. Clin Chem 46, 1929-1938.

Devor E J (2001) Use of molecular beacons to verify that the serine hydroxymethyltransferase pseudogene SHMT-ps1 is unique to the order primates. Genome Biol 2. 6.1-6.5.

Dracheva S, Marras S A E, Elhakem A L, Kramer F R, Davis K L, and Haroutunian V (2001) N-Methyl-D-Aspartic Acid Receptor expression in Dorsolateral Prefrontal Cortex of elderly patients with schizophrenia. American Journal of Psychiatry. 158, 1400-1410.

Durand R, Eslahpazire J, Jafari S, Delabre J F, Marmorat-Khuong A, di Piazza J P, and Le Bras J (2000) Use of molecular beacons to detect an antifolate resistance-associated mutation in *Plasmodium falciparum*. Antimicrob Agents Chemother 44, 3461-3464.

Eun A J C and Wong S M (2000) Molecular beacons: a new approach to plant virus detection. Phytopathology 90, 269-275.

Fortin N Y, Mulchandani A, and Chen W (2001) Use of real-time polymerase chain reaction and molecular beacons for the detection of *Escherichia coli* O157:H7. Anal Biochem 289, 281-288.

Gonzalez E, Bamshad M, Sato N, Mummidi S, Dhanda R, Catano G, Cabrera S, McBride M, Cao X H, Merrill G, O'Connell P, Bowden D W, Freedman B I, Anderson S A, Walter E A, Evans J S, Stephan K T, Clark R A, Tyagi S, Ahuja S S, Dolan M J, and Ahuja S K (1999) Race-specific HIV-1 disease-modifying effects associated with CCR5 haplotypes. Proc Natl Acad Sci USA 96, 12004-12009.

Heil S G, Lievers K J, Boers G H, Verhoef P, den Heijer M, Trijbels F J, and Blom H J (2000) Betaine-Homocysteine Methyltransferase (BHMT): genomic sequencing and relevance to hyperhomocysteinemia and vascular disease in humans. Mol Genet Metab 71, 511-519.

Helps C, Reeves N, Tasker S, and Harbour D (2001) Use of real-time quantitative PCR to detect *Chlamydophila felis* infection. J Clin Microbiol 39, 2675-2676.

Kota R, Holton T A, and Henry R J (1999) Detection of transgenes in crop plants using molecular beacon assays. Plant Mol Biology Rep 17, 363-370.

Lewin S R, Vesanen M, Kostrikis L, Hurley A, Duran M, Zhang L, Ho D D, and Markowitz M (1999) Use of real-time PCR and molecular beacons to detect virus replication in human immunodeficiency virus type 1-infected individuals on prolonged effective antiretroviral therapy. J Virol 73, 6099-6103.

Li Q, Liang J, Luan G, Zhang Y, and Wang K (2000) Molecular beacon-based homogeneous fluorescence PCR assay for the diagnosis of infectious diseases. Analytical Sciences 16, 245-248.

Manganelli R, Dubnau E, Tyagi S, Kramer F R, and Smith I (1999) Differential expression of 10 sigma factor genes in *Mycobacterium tuberculosis*. Mol Microbiol 31, 715-724.

Martinson J J, Hong L, Karanicolas R, Moore J P, and Kostrikis L G (2000) Global distribution of the CCR2-64I/CCR5-59653T HIV-1 disease-protective haplotype. Aids 14, 483-489.

McKillip J L and Drake M (2000) Molecular beacon polymerase chain reaction detection of *Escherichia coli* O157:H7 in milk. J Food Prot 63, 855-859.

Metzner K J, Jin X, Lee F V, Gettie A, Bauer D E, Di Mascio M, Perelson A S, Marx P A, Ho D D, Kostrikis L G, and Connor R I (2000) Effects of in vivo CD8(+) T cell depletion on virus replication in rhesus macaques immunized with a live, attenuated simian immunodeficiency virus vaccine. J Exp Med 191, 1921-1931.

Park S, Wong M, Marras S A, Cross E W, Kiehn T E, Chaturvedi V, Tyagi S, and Perlin D S (2000) Rapid identification of *Candida dubliniensis* using a species-specific molecular beacon. J Clin Microbiol 38, 2829-2836.

Pierce K E, Rice J E, Sanchez J A, Brenner C, and Wangh L J (2000) Real-time PCR using molecular beacons for accurate detection of the Y chromosome in single human blastomeres. Mol Hum Reprod 6, 1155-1164.

Poddar S K (2000) Symmetric vs asymmetric PCR and molecular beacon probe in the detection of a target gene of adenovirus. Mol Cell Probes 14, 25-32.

Poddar S K (1999) Detection of adenovirus using PCR and molecular beacon. J Virol Methods 82, 19-26.

Sebti A, Kiehn T E, Perlin D, Chaturvedi V, Wong M, Doney A, Park S, and Sepkowitz K A (2001) *Candida dubliniensis* at a Cancer Center. Clin Infect Dis 32, 1034-1038.

Shih I M, Zhou W, Goodman S N, Lengauer C, Kinzler K W, and Vogelstein B (2001) Evidence that genetic instability occurs at an early stage of colorectal tumorigenesis. Cancer Res 61, 818-822.

Smit M L, Giesendorf B A, Vet J A, Trijbels F J, and Blom H J (2001) Semiautomated DNA mutation analysis using a robotic workstation and molecular beacons. Clin Chem 47, 739-744.

Steuerwald N, Cohen J, Herrera R J, and Brenner C A (1999) Analysis of gene expression in single oocytes and embryos by real-time rapid cycle fluorescence monitored RT-PCR. Mol Hum Reprod 5, 1034-1039.

Valentin A, Trivedi H, Lu W, Kostrikis L G, and Pavlakis G N (2000) CXCR4 mediates entry and productive infection of syncytia-inducing (X4) HIV-1 strains in primary macrophages. Virology 269, 294-304.

Van Schie R C, Marras S A, Conroy J M, Nowak N J, Catanese J J, and de Jong P J (2000) Semiautomated clone verification by real-time PCR using molecular beacons. Biotechniques 29, 1296-1306.

Vet J A, Majithia A R, Marras S A E, Tyagi S, Dube S, Poiesz B J, and Kramer F R (1999) Multiplex detection of four pathogenic retroviruses using molecular beacons. Proc Natl Acad Sci USA 96, 6394-6399.

Xiao G, Chicas A, Olivier M, Taya Y, Tyagi S, Kramer F R, and Bargonetti J (2000) A DNA damage signal is required for p53 to activate gadd45. Cancer Res 60, 1711-1719.

Zhang L, Lewin S R, Markowitz M, Lin H H, Skulsky E, Karanicolas R, He Y, Jin X, Tuttleton S, Vesanen M, Spiegel H, Kost R, van Lunzen J, Stellbrink H J, Wolinsky S, Borkowsky W, Palumbo P, Kostrikis L, and Ho D D (1999) Measuring recent thymic emigrants in blood of normal and HIV-1-infected individuals before and after effective therapy. J Exp Med 190, 725-732.

De Baar M P, van Dooren M W, de Rooij E, Bakker M, van Gemen B, Goudsmit J, and de Ronde A (2001) Single rapid real-time monitored isothermal RNA amplification assay for quantification of Human Immunodeficiency Virus Type 1 isolates from groups M, N, and O. J Clin Microbiol 39, 1378-1384.

De Baar M P, Timmermans E C, Bakker M, de Rooij E, van Gemen B, and Goudsmit J (2001) One-tube real-time isothermal amplification assay to identify and distinguish Human Immunodeficiency Virus Type 1 subtypes A, B, and C and circulating recombinant forms AE and AG. J Clin Microbiol 39, 1895-1902.

De Ronde A, van Dooren M, van Der Hoek L, Bouwhuis D, de Rooij E, van Gemen B, de Boer R, and Goudsmit J (2001) Establishment of new transmissible and drug-sensitive Human Immunodeficiency Virus Type 1 wild types due to transmission of nucleoside analogue-resistant virus. J Virol 75, 595-602.

Greijer A. E., Adriaanse H. M., Dekkers C. A., and Middeldorp J. M. (2002) Multiplex real-time NASBA for monitoring expression dynamics of human cytomegalovirus encoded IE1 and pp 67 RNA. J Clin Virol 24, 57-66.

Klerks M M, Leone G O, Verbeek M, van den Heuvel J F, and Schoen C D (2001) Development of a multiplex AmpliDet RNA for the simultaneous detection of Potato leafroll virus and Potato virus Y in potato tubers. J Virol Methods 93, 115-125.

Leone G, van Schijndel H, van Gemen B, Kramer F R, and Schoen C D (1998) Molecular beacon probes combined with amplification by NASBA enable homogeneous, real-time detection of RNA. Nucleic Acids Res 26, 2150-2155.

Lanciotti R. S, and Kerst A. J. (2001) Nucleic acid sequence-based amplification assays for rapid detection of West Nile and St. Louis encephalitis viruses. J Clin Microbiol 39, 4506-4513.

Szemes M., Klerks M. M., van den Heuvel J. F., and Schoen C. D. (2002) Development of a multiplex AmpliDet RNA assay for simultaneous detection and typing of potato virus Y isolates. J Virol Methods 100, 83-96.

Van Beuningen R, Marras S A E, Kramer F R, Oosterlaken T, Weusten J, Borst G, and van de Wiel P (2001) Development of a high-throughput detection system for HIV-1 using real-time NASBA based on molecular beacons. Proceedings—SPIE the International Society for Optical Engineering. 4264, 66-71.

Yates S, Penning M, Goudsmit J, Frantzen I, van De Weijer B, van Strijp D, and van Gemen B (2001) Quantitative detection of Hepatitis B Virus DNA by real-time nucleic acid sequence-based amplification with molecular beacon detection. J Clin Microbiol 39, 3656-3665.

Brown L J, Cummins J, Hamilton A, and Brown T (2000) Molecular beacons attached to glass beads fluoresce upon hybridisation to target DNA. Chemical Comm, 621-622.

Liu X, Farmerie W, Schuster S, and Tan W (2000) Molecular beacons for DNA biosensors with micrometer to submicrometer dimensions. Anal Biochem 283, 56-63.

Liu X and Tan W (1999) A fiber-optic evanescent wave DNA biosensor based on novel molecular beacons. Anal Chem 71, 5054-5059.

Steemers F J, Ferguson J A, and Walt D R (2000) Screening unlabeled DNA targets with randomly ordered fiber-optic gene arrays. Nat Biotechnol 18, 91-94.

Antony T, Thomas T, Sigal L H, Shirahata A, and Thomas T J (2001) A molecular beacon strategy for the thermodynamic characterization of triplex DNA: triplex formation at the promoter region of cyclin D1. Biochemistry 40, 9387-9395.

Bonnet G, Krichevsky O, and Libchaber A (1998) Kinetics of conformational fluctuations in DNA hairpin-loops. Proc Natl Acad Sci USA 95, 8602-8606.

Fang X, Li J J, and Tan W (2000) Using molecular beacons to probe molecular interactions between lactate dehydrogenase and single-stranded DNA. Anal Chem 72, 3280-3285.

Gao W, Tyagi S, Kramer F R, and Goldman E (1997) Messenger RNA release from ribosomes during 5'-translational blockage by consecutive low-usage arginine but not leucine codons in Escherichia coli. Mol Microbiol 25, 707-716.

Goddard N L, Bonnet G, Krichevsky O, and Libchaber A (2000) Sequence dependent rigidity of single stranded DNA. Phys Rev Lett 85, 2400-2403.

Gold B, Rodriguez M, Marras S A E, Pentecost M, and Smith I (2001) The *Mycobacterium tuberculosis* IdeR is a dual functional regulator that controls transcription of genes involved in iron acquisition, iron storage, and survival in macrophages. Molecular Microbiology 42, 851-866.

Jordens J Z, Lanham S, Pickett M A, Amarasekara S, Abeywickrema I, and Watt P J (2000) Amplification with molecular beacon primers and reverse line blotting for the detection and typing of human papillomaviruses. J Virol Methods 89, 29-37.

Joshi H S and Tor Y (2001) Metal-containing DNA hairpins as hybridization probes. Chemical Comm 6, 559-550.

Kaboev O K, Luchkina L A, Tret'iakov A N, and Bahrmand A R (2000) PCR hot start using primers with the structure of molecular beacons (hairpin-like structure). Nucleic Acids Res 28, E94.

Li J J, Geyer R, and Tan W (2000) Using molecular beacons as a sensitive fluorescence assay for enzymatic cleavage of single-stranded DNA. Nucleic Acids Res 28, E52.

Li J J, Fang X H, Schuster S M, and Tan W H (2000) Molecular beacons: a novel approach to detect protein-DNA interactions. Angew Chem Int Ed 39, 1049-1052.

Lindquist J N, Kauschke S G, Stefanovic B, Burchardt E R, and Brenner D A (2000) Characterization of the interaction between alphaCP(2) and the 3'-untranslated region of collagen alpha1 (I) mRNA. Nucleic Acids Res 28, 4306-4316.

Liu J., Feldman P., and Chung T. D. (2002) Real-time monitoring in vitro transcription using molecular beacons. Anal Biochem 300, 40-45.

Matsuo T (1998) In situ visualization of mRNA for basic fibroblast growth factor in living cells. Biochimica Biophysica Acta 1379, 178-184.

Nazarenko I A, Bhatnagar S K, and Hohman R J (1997) A closed tube format for amplification and detection of DNA based on energy transfer. Nucleic Acids Res 25, 2516-2521.

Saha B K, Tian B, and Bucy R P (2001) Quantitation of HIV-1 by real-time PCR with a unique fluorogenic probe. J Virol Methods 93, 33-42.

Schofield P, Pell A N, and Krause D 0 (1997) Molecular beacons: trial of a fluorescence-based solution hybridization technique for ecological studies with ruminal bacteria. Appl Environ Microbiol 63, 1143-1147.

Sokol D L, Zhang X, Lu P, and Gewirtz A M (1998) Real time detection of DNA.RNA hybridization in living cells. Proc Natl Acad Sci USA 95, 11538-11543.

Strouse R J, Hakki F Z, Wang S C, DeFusco A W, Garrett J L, and Schenerman M A (2000) Using molecular beacons to quantify low levels of type I endonuclease activity. Biopharm 13, 40-47.

Tan W, Fang X, Li J, and Liu X (2000) Molecular beacons: a novel DNA probe for nucleic acid and protein studies. Chemistry 6, 1107-1 1111.

Thelwell N, Millington S, Solinas A, Booth J, and Brown T (2000) Mode of action and application of scorpion primers to mutation detection. Nucleic Acids Res 28, 3752-3761.

Tung C H, Mahmood U, Bredow S, and Weissleder R (2000) In vivo imaging of proteolytic enzyme activity using a novel molecular reporter. Cancer Res 60, 4953-4958.

Whitcombe D, Theaker J, Guy S P, Brown T, and Little S (1999) Detection of PCR products using self-probing amplicons and fluorescence. Nat Biotechnol 17, 804-807.

Yamamoto R, Baba T, and Kumar P K (2000) Molecular beacon aptamer fluoresces in the presence of Tat protein of HIV-1. Genes Cells 5, 389-396.

Ying L, Wallace M I, and Klenerman D (2001) Two-state model of conformational fluctuation in a DNA hairpin-loop. Chemical Physics Letters 334, 145-150.

Zhang P, Beck T, and Tan W (2001) Design of a molecular beacon DNA probe with two fluorophores. Angew. Chem. Int. Ed. 40, 402-405.

Nonlinear Optical Techniques

Surface-selective nonlinear optical techniques have previously been confined mainly to physics and chemistry since relatively few biological samples are intrinsically non-linearly active. Examples include the use of an optically nonlinear-active dye as a membrane stain—and an endogenous nonlinear-active stain (GFP) that is used to image biological cells (Campagnola et al., "High-resolution nonlinear optical imaging of live cells by second harmonic generation," Biophysical Journal 77 (6), 3341-3349 (1999), Peleg et al., "Nonlinear optical measurement of membrane potential around single molecules at selected cellular sites," Proc. Natl. Acad. Sci. V. 96, (1999), 6700-6704 and references therein). The following references (and references therein) are exemplary of this art:

A. Lewis, A. Khatchatouriants, M. Treinin, Z. Chen, G. Peleg, N. Friedman, O. Bouevitch, Z. Rothman, L. Loew and M. Sheves, "Second Harmonic Generation of Biological Interfaces: Probing the Membrane Protein Bacteriorhodopsin and Imaging Membrane Potential Around GFP Molecules at Specific Sites in Neuronal Cells of C. elegans," Chemical Physics 245, 133 (1999).

O. Bouevich, A. Lewis, I. Pinnevsky and L. Loew, "Probing Membrane Potential with Non-linear Optics," Biophys. J. 65, 672 (1993).

I. Ben-Oren, G. Peleg, A. Lewis, B. Minke and L. Loew, "Infrared nonlinear optical measurements of membrane potential in photoreceptor cells," Biophys. J. 71, 616 (1996).

G. Peleg, A. Lewis, M. Linial and L. M. Loew, "Non-linear Optical Measurement of Membrane Potential Around Single Molecules at Selected Cellular Sites," Proc. Acad. Sci. USA 96, 6700 (1999).

P. Campagnola, Mei-de Wei, A. Lewis and L. Loew, "High-Resolution Nonlinear Optical Imaging of Live Cells by Second Harmonic Generation," Biophys. J. 77, 3341 (1999).

J. Y. Huang, A. Lewis and L. Loew, "N[on-linear Optical Properties of Potential Sensitive Styryl Dyes", Biophysical J. 53, 665 (1988).

A. Lewis, A. Khatchatouriants, M. Treinin, Z. Chen, G. Peleg, N. Friedman, O. Bouevitch, Z. Rothman, L. Loew and M. Sheves, "Second Harmonic Generation of Biological Interfaces: Probing Membrane Proteins and Imaging Membrane Potential Around GFP Molecules at Specific Sites in Neuronal Cells of C. elegans," Chemical Physics 245, 133-144 (1999).

A. Khatchatouriants, A. Lewis, Z. Rothman, L. Loew and M. Treinin, "GFP is a Selective Non-Linear Optical Sensor of Electrophysiological Processes in C. elegans," Biophys. J. (in press, 2000)

In the prior art, nonlinear-active stains are immobilized in membranes and these stains are used to image the cell surfaces. However, the stains intercalate into the membranes in either an 'up' or 'down' direction, thus reducing the total nonlinear signal due to destructive interference. Nonlinear optically active dyes have also been used to measure the kinetics of those dyes crossing lipid bilayers in liposomes (A. Srivastava and K B Eisenthal, "Kinetics of molecular transport across a liposome bilayer," Chem. Phys. Lett. 292 (3): 345-351 (1998)).

The present invention provides advantages over fluorescence-based detection, such as reduced background, reduced photobleaching, simplified optical detection, and no need for labor- or time-consuming washing steps. These advantages are due to the low background of the nonlinear optical techniques and the fact that the method is a scattering rather than an absorption process.

It is therefore an object of the present invention to provide a direct, optical means of detecting probe-target binding reactions in cases where the binding reaction results in a change in orientation or conformation of the probe, target, or both probe and target.

SUMMARY OF THE INVENTION

The invention discloses a method for screening one or more candidate binding partners (referred to herein as probes) for binding to a test molecule (referred to herein as targets). The method involves illuminating a sample with one or more light beams at one or more fundamental frequencies, said sample comprising the test molecule exposed to the one or more candidate binding partners, and measuring one or more physical properties of a nonlinear optical light beam emanating from the sample. A change in the value of the one or more physical properties measured relative to a value for the one or more physical properties measured in the absence of exposure of said test molecule to said one or more candidate binding partners indicates that said one or more candidate binding partners bind said test molecule.

The invention discloses a method for screening one or more candidate modulator molecules for the ability to modulate an interaction between a test molecule and its binding partner. The method involves illuminating a sample with one or more light beams at one or more fundamental frequencies, said sample comprising said test molecule exposed to (i) said binding partner, and (ii) said one or more candidate modulator molecules, and measuring one or more physical properties of a nonlinear optical light beam emanating from said sample. A change in the value of said one or more physical properties measured relative to the value for said one or more physical properties measured in the absence of exposure to said one or more candidate modulator molecules indicates that said one or more candidate modulator molecules modulate the interaction between said test molecule and its binding partner.

The invention provides a method for detecting a conformational change in a test molecule upon binding of the test molecule to a binding partner comprising contacting said test molecule with one or more candidate binding partners, where the test molecule or the one or more candidate binding partners is labeled with a nonlinear-active moiety that is not native to the test molecule or the one or more candidate binding partners, respectively. The method involves illuminating said contacted test molecule with one or more light beams at one or more fundamental frequencies, and measuring one or more physical properties of a nonlinear optical light beam emanating from said sample. A change in the value of said one or more physical properties measured relative to the value for said one or more physical properties measured in the absence of said one or more candidate binding partners indicates that at least one of said one or more candidate binding partners bind to said test molecule and that said binding induces a conformational change in said candidate binding partners, in said test molecule, or in both said candidate binding partners and said test molecule.

The invention provides a method for detecting the degree or extent of the binding interaction between a test molecule and one or more binding partner comprising contacting said test molecule with one or more candidate binding partners, wherein the test molecule or the one or more candidate binding partners is labeled with a nonlinear-active moiety that is not native to the test molecule or the one or more candidate binding partners, respectively. The method involves illuminating said contacted test molecule with one or more light beams at one or more fundamental frequencies, and measuring one or more physical properties of a nonlinear optical light beam emanating from the sample. A change in the value of said one or more physical properties measured relative to the value for the one or more physical properties measured in the absence of said one or more candidate binding partners indicates that at least one of said one or more candidate binding partners binds to said test molecule, the degree or extent of the conformational change that said binding induces.

In a specific embodiment, the present invention relates to a method for detecting interactions between biological components using a surface-selective nonlinear optical technique. In one aspect of the present invention this relates to detection of binding between probes and targets that results in a conformational change. The invention discloses methods for screening one or more probes through the conformational changes they induce on binding targets. The invention also discloses methods for screening modulators of the probe-target binding interaction, and for determining the degree or extent of binding through the conformational changes the binding induces.

BRIEF DESCRIPTION OF THE DRAWINGS

In FIG. 5A, the second harmonic beam is co-linear with the fundamental. In FIG. 5B, the second harmonic is collected from a direction orthogonal to the fundamental ('right-angle collection'). In FIG. 5C, the second harmonic light is collected by an integrating sphere and a fiber optic line.

FIG. 6 depicts an embodiment of the transformation, using a series of optical components, of a collimated beam of the fundamental light into a line shape suitable for scanning a substrate.

FIGS. 7A-B depict an embodiments patterned in an array format. FIG. 7A depicts an embodiment of a substrate surface (containing attached probes) which has been patterned into an array format (elements 1-35). FIG. 7B depicts one element of a substrate array in which each element is a well with walls, with surface-attached probes, and the well is capable of holding some liquid and serves to physically separate the well's contents from adjacent wells or other parts of the substrate.

FIG. 9A depicts the substrate containing multiple wells (1-16), each of which contains surface-attached probes as depicted in FIG. 9B.

FIGS. 11 A-B depict an embodiment of an apparatus in which the mode of generation and collection of the second harmonic light is through a fiber optic.

FIG. 12A depicts both the fundamental and second harmonic beams travelling co-linearly through a sample. FIG. 122B depicts the fundamental and second harmonic beams being refracted at the top surface (top surface contains attached probes) of a substrate with this surface generating the second harmonic light. FIG. 12C depicts a similar apparatus to FIG. 12B except that the bottom surface (bottom surface contains attached probes) generates the second harmonic light.

FIGS. 13A-B depict two embodiments of an apparatus in which second harmonic light is generated by total internal reflection at an interface. The points of generation of the second harmonic light are denoted by the circles. In FIG. 13A, a dove prism is used to guide the light to a surface capable of generating the second harmonic light (bottom surface of prism but can also be another surface coupled to the prism through an index-matching material). In FIG. 133B, a wave-guide structure is used to produce multiple points of second harmonic generation.

FIGS. 14A-C depict three embodiments of an apparatus in which second harmonic light is generated using a fiber optic line (with attached probes at the end of the fiber). FIG. 14A depicts an apparatus in which both generation and collection of the second harmonic light occur in the same fiber. FIG. 14B depicts the use of a bead containing surface-attached probes at the end of the fiber. FIG. 14C depicts an apparatus in which the second harmonic light is generated at the end of the fiber optic (containing attached probes) and collected using a mirror or lens external to the fiber optic.

FIG. 19C depicts a conformational change process. Receptors in a membrane surface (e.g., a host cell) are labeled with nonlinear-active labels which, on average, possess an orientation with respect to the surface plane, specifically an angle of .theta. of the hyperpolarizability with respect to the surface plane; binding and subsequent activation of the receptor by ligands causes the labels to shift orientation to angle 74. Small shifts in angle can cause a substantial change in a physical property of the measured nonlinear optical light (e.g., intensity of the light).

In FIG. 20A, a single strand of nucleotides is coupled to a nonlinear-active dye (gray-hatch) and an enhancer (open circle). When the molecular beacon analogue is hybridized to a complementary target, the dye and enhancer are separated by the conformational change, leading to a measurable change in the nonlinear response of the dye. The amount of the change can be made quantitative with the amount of probe-target hybridization. In FIG. 20B, an example of a particular oligonucleotide sequence with attached dye and enhancer (Au particle) is shown (SEQ ID NO: 5). The sequences of various targets (SEQ ID NOs: 1-4, respectively) used for testing the degree of hybridization to this probe are also shown.

DESCRIPTION OF THE INVENTION

Figure 1:
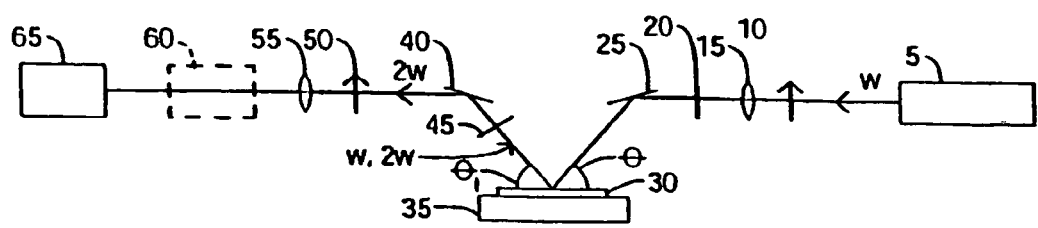
FIG. 1 depicts one embodiment of the apparatus in which the mode of generation and collection of the second harmonic light is by reflection off the substrate with surface-attached probes.

The present invention uses a nonlinear optical technique to detect probe-target interactions involving a conformational change. Examples of nonlinear optical technique include but are not limited to second-harmonic generation, sum-frequency generation, difference-frequency generation, third-harmonic generation and hyper-Rayleigh scattering HRS). The present invention can be used with any of the nonlinear optical techniques, however many embodiments describe the use of the second-order techniques (e.g., second-harmonic generation and hyper-Rayleigh scattering). The following references, and references therein, describe the field of nonlinear optics:

Nonlinear Optics, R. W. Boyd, 1991, Academic Press.
The Elements of Nonlinear Optics, P. N. Butcher and D. Cotter, Cambridge University Press, 1991.
Nonlinear Optical Techniques Nonlinear optical light is any light that results from a nonlinear transformation of light beams at one or more fundamental frequencies (also referred to herein as fundamental beam(s)). A nonlinear optical technique is capable of transforming the physical properties, such as frequency, intensity, etc., of one or more incident light beams, called the fundamental beams. The nonlinear beams emanating from the sample are the higher order frequency beams, e.g. second or third harmonic, etc., or the beams at the sum or difference frequencies. For example, in second harmonic generation (SHG), two photons of the fundamental beam are virtually scattered by the sample to produce one photon of the second harmonic. A nonlinear optical technique is also referred to herein as a surface-selective nonlinear optical technique.

Second harmonic generation (SHG) and other surface-selective nonlinear optical techniques are directly related to the orientation of the nonlinear-active species in a sample, because the fundamental and nonlinear beams have well-defined phase relationships, and the wavefronts of the nonlinear beam in a macroscopic sample (within the coherence length) are in phase. Any change in the orientation of the nonlinear-active species can be detected by measuring one or more physical properties of the nonlinear optical beam emanating from the sample. These coherency properties of the nonlinear optical technique offer a number of advantages useful for surface or high-throughput studies in which, for example, either a single surface or a microarray surface is examined. The coherent nature of the nonlinear optical beam emanating from the sample also allows discrimination among more than one nonlinear optical beam emanating from a sample. In alternate embodiments of the invention, assays can be conducted where multiple fundamental light beams at one or more frequencies, incident with one or more polarization directions relative to the sample, can be used, with the resulting emanation of at least two nonlinear beams. An apparatus using nonlinear optical surface-selective-based detection, such as with second harmonic generation, requires minimal collection optics since generation of the nonlinear light only occurs at the interface (in the absence of an applied field) and thus, in principle, allows extremely high depth discrimination and fast scanning.

A common equation used to model orientation dependence of nonlinear-active species at an interface is:

$$\chi^{(2)} = N_S \langle \alpha^{(2)} \rangle$$

where $\omega^{(2)}$ is the nonlinear susceptiblity, $N_S$ is the total number of molecules per unit area at the interface and $\langle \alpha^{(2)} \rangle$ is the average over the orientational distribution of the nonlinear hyperpolarizabilities—$\alpha^{(2)}$—in these molecules. Typical equations describing the nonlinear interaction for second harmonic generation are: $\alpha^{(2)}(2\omega) = \beta E(\omega) \cdot E(\omega)$ or $P^{(2)}(2\omega) = \chi^{(2)} : E(\omega)E(\omega)$ where $\alpha$ and P are, respectively, the induced molecular and macroscopic dipoles oscillating at frequency $2\omega$, $\beta$ and $\chi^{(2)}$ are, respectively, the hyperpolarizability and second-harmonic (nonlinear) susceptibility tensors, and $E(\omega)$ is the electric field component of the incident radiation oscillating at frequency $\omega$. The macroscopic nonlinear susceptibility $\chi^{(2)}$ is related by an orientational average of the microscopic hyperpolarizability. The next order term in the expansion of the induced macroscopic dipole describes other nonlinear phenomenon, such as third harmonic generation. The third order term is responsible for such nonlinear phenomena as two-photon fluorescence. For sum or difference frequency generation, the driving electric fields (fundamentals) oscillate at different frequencies (i.e., $\omega_1$ and $\omega_2$) and the nonlinear radiation oscillates at the sum or difference frequency $(\omega_1 \pm \omega_2)$.

The intensity of SHG is proportional to the square of the nonlinear susceptibility and is dependent on the amount of oriented nonlinear-active species in a sample, and thus to changes in this orientation, both at an interface and species aligned in the bulk (the latter through an electric field-poled mechanism, for example). This property can be exploited to detect a conformational change. For example, conformational change in receptors can be detected using a nonlinear-active label or moiety wherein the label is attached to or associated with the receptor; a conformational change leads to a change in the direction (orientation) of the label with respect to the surface plane (or applied field direction) and thus to a change in a physical property of the nonlinear optical signal. The techniques are intrinsically sensitive to these changes at an interface and can be made sensitive to them in the bulk as well, by applying an electric field to pole molecules or simply by detecting that fraction of the ensemble which produce hyper-Rayleigh scattering (HRS) due to fluctuational changes in their number density or orientation as is well known to one skilled in the art.

In hyper-Rayleigh scattering (HRS), the fluctuations of nonlinear-active molecules lead to instantaneous departures from centrosymmetry, and thus allow for a low amount of second-harmonic emission to occur, although this emission is incoherent. Because the fluctuations depend on molecular size, among other properties, HRS can be used to discriminate an unbound molecule in solution from the same molecule bound to one or more binding partners (also referred to herein as probes). Thermal energy drives the fluctuations required for HRS, however, an external force can also be applied to induce or amplify the fluctuations, thus increasing the HRS signal. For example, a flow-field can be used to transiently orient molecules in solution by injecting a burst or stream of fluid into it. Pulsed and alternating electric fields applied to the sample can also increase the HRS signal.

There are a number of examples in the literature of the use of HRS to measure beta (hyperpolarizability) of nonlinear optical molecules. The present invention extends the use of HRS to detect binding interactions and to screen for test molecules (also referred to herein as targets) or modulators (described below) capable of binding or modulating probe-target interactions.

The following references, and references therein, describe the HRS technique:

Clays, K. et al., "Nonlinear Optical Properties of Proteins Measured by Hyper-Rayleigh Scattering in Solution", Science, v. 262 (5138), 1419-22

Vance, F W, Lemon B. I., Hupp, J. T. Enormous Hyper-Rayleigh Scattering from Nanocrystalline Gold Particle Suspensions", J. Phys. Chem. B 102:10091-93 (1999).

Electric field induced second harmonic (EFISH) is technique well known in the field of nonlinear optics that can be used according to the invention to render a system nonlinear-active that is not normally so, such as a bulk phase, through the application of an electric field that breaks the symmetry of the bulk phase. In a specific embodiment, the EFISH technique can be used to measure the hyperpolarizability of molecules in solution by using a dc field to induce alignment in the medium, and allowing nonlinear-activity (such as SHG) to be observed. This is sometimes called the reorientational mechanism.

EFISH is a third order nonlinear optical effect, with the polarization source written as:

$$P^{(2)}(\omega_3) = \chi^{(2)}(-\omega_3;\omega_1,\omega_2):E^{\omega 1}E^{\omega 2}$$

The polarization is the result of the application of two optical fields and a static (dc) field.

The following references describe applying the EFISH technique to, e.g., liquid and condensed phase samples:

R. Dworczak and D. Kieslinger, Phys. Chem. Chem. Phys., 2000, 2, 5057-5064.

J. L. Oudar, J. Chem. Phys., 1977, 67, 446.

B. F. Levine and C. G. Bethea, J. Chem. Phys., 1974, 60, 3856.

B. F. Levine and C. G. Bethea, J. Chem. Phys., 1975, 63, 2666.

K. D. Singer and A. F. Garito, J. Chem. Phys., 1981, 75, 3572.

C. G. Bethea, Applied Optics, 1975, 14, 1447.

B. F. Levine and C. G. Bethea, J. Chem. Phys., 1976, 65, 1989.

B. F. Levine and C. G. Bethea, J. Chem. Phys., 1974, 60, 3856.

B. F. Levine, J. Chem. Phys., 1975, 63, 115.

B. F. Levine and C. G. Bethea, J. Chem. Phys. 1977, 66, 1070.

J. L. Oudar and D. S. Chemla, J. Chem. Phys., 1977, 66, 2664.

R. S. Finn and J. F. Ward, J. Chem. Phys., 1974, 60, 454.

B. F. Levine and C. G. Bethea, Appl. Phys. Lett., 1974, 24, 445.

In addition, the electrodes used to apply the electric field can be spatially patterned (periodically patterned) to achieve quasi-phase matching. Quasi-phase matching is a well known technique for increasing the effective nonlinear path length in a nonlinear-active material, by alternating the nonlinear susceptibility of a material with a period of a coherence length. The following references (and references therein) describe this technique:

M. Jager et al., Appl. Phys. Lett. 68, 1996, 1183.

M. M. Fejer et al., IEEE Journal of Quantum Electronics, v. 28, 1992, 2631.

G. D. Landry et T. A. Maldonado, Optics Express, v. 5, 1999, 176.

The electrodes used to apply the external electric field in the EFISH technique can assume a variety of shapes, forms and compositions as, for example, are found in the prior art. For instance, the electrodes can be angled or pointed to increase the electric field strength that results in these cases. The electrodes can be oriented in a variety of ways to the sample; for example, the electrodes can be placed (e.g., patterned lithographically, printed, etched, etc.) on a substrate which itself is in contact with the liquid sample containing the targets and probes; or, for example, the electrodes can lie at the bottom and top of a thin cavity in which the sample containing targets and probes is flowing or is held.

Non-Random Orientations and Nonlinear Activity

A non-random orientation is a necessary condition for generation of the surface-selective nonlinear optical signal. Only the non-centrosymmetric region of a system, is capable of generating non-linear light. A molecule or material phase is centrosymmetric if there exists a point in space, called the 'center' or 'inversion center,' through which an inversion $(x,y,z) \rightarrow (-x,-y,-z)$ of all atoms can be performed that leaves the molecule or material unchanged. For example, if the molecule is of uniform composition and spherical in shape, it is centrosymmetric. Centrosymmetric molecules or materials have no nonlinear susceptibility or hyperpolarizability, necessary for second or higher harmonic, sum frequency and difference frequency generation. A non-centrosymmetric molecule or material lacks this center of inversion, and therefore can be nonlinear-active. Non-centrosymmetric regions can be at surfaces, e.g. arrays, substrates, etc., or in bulk phase, e.g. solutions, however, a bulk phase may require the application of an electric field to break the symmetry of the region and render the bulk phase nonlinear-active (as in the EFISH technique).

The present invention exploits the property that any non-random orientation of probes with respect to a surface to which they are attached or localized leads to non-random orientation of targets when these targets bind to the probes. As a result of the non-random orientation of the system, a non-linear optical technique can be used to monitor, e.g., the binding activity at the surface. Any change in the non-random orientation of the system, such as due to a conformational change on occurrence of a binding event, would modify the nonlinear optical signal. Verification that a change in the detected nonlinear optical signal is due to a conformational change can be accomplished using controls known to one skilled in the art including, for example, measuring binding of a blocking compound to the receptor—where the blocking compound is known not to produce a conformational change in the receptor.

In an embodiment in which the probe or target, or neither, is not natively nonlinear-active, then different types of nonlinear-active species can be introduced into the system to render the system nonlinear-active. Such species that affect the one or more nonlinear-active beams emanating from a sample comprising probes and targets include labels, decorators, indicators, modulators, inhibitors, and enhancers, as described below. When the present invention is used with labels or decorators, the non-random orientation of the target produces a non-random label or decorator orientation and this leads directly to an increase in surface-selective nonlinear optical signal (e.g., intensity). Non-specific interactions of the targets with attached or localized probes (e.g., non-specific binding to probes) or of targets to regions on the surface where no probe is present (e.g., non-specific binding to substrate or solid support) will lead to zero or to a much lower surface-selective nonlinear optical signal due to destructive interference as would be apparent to one skilled in the art. When the present invention is used with indicators, a non-random probe orientation also leads to an increase in the surface-selective nonlinear optical signal since the surface charge density close to the surface plane will be larger than if the probes are randomly oriented which results in a lower surface electric charge density.

Nonlinear-Active Labels

A label for use in the present invention refers to a nonlinear-active moiety, particle or molecule which can be bound, either covalently or non-covalently, to a molecule, particle or phase (e.g., lipid bilayer) in order to render the resulting system more nonlinear optical active. Labels can be employed in the case where the molecule, particle or phase (e.g., lipid bilayer) is not nonlinear-active to render the system nonlinear-active, or with a system that is already nonlinear-active to add an extra manipulation parameter into the system. The exogenous labels can be pre-attached to the molecules or particles, and any unbound or unreacted labels separated from the labeled entities before a measurement is made. In a specific embodiment, the nonlinear-active moiety is attached to the target or probe molecule in vitro. Alternatively, the labels can be left in solution with probes and targets and allowed to adsorb to some particle (e.g., an enhancer) or surface to yield a different nonlinear-active response (i.e., hyperpolarizability or second order susceptibility) from the bound labels. By way of example, EFISH or Hyper-Rayleigh scattering can be used to determine if a candidate molecule or particle is nonlinearly active according to techniques well known in the art, where appropriate controls and background measurements are made in the absence of access to the candidate nonlinear-active species. The labeling of probes with nonlinear-active labels and/or modulators of the labels allows a direct, optical means of detecting probe-target binding reactions in the cases where the binding reaction results in a change in orientation or conformation of the probe using a surface-selective nonlinear optical technique.

In alternate embodiments of the invention, at least two distinguishable nonlinear-active labels are used. The orientation of the attached two or more distinguishable labels would then be chosen to facilitate well defined directions of the emanating coherent nonlinear light beam. The two or more distinguishable labels can be used in assays where multiple fundamental light beams at one or more frequencies, incident with one or more polarization directions relative to the sample, are used, with the resulting emanation of at least two nonlinear light beams.

One means of determining whether a particular molecule or particle can be used as a nonlinear-active label is by studying it using second harmonic generation at an air-water interface. For instance, in the case of particles, if the particles assemble at the air-water interface in a manner which gives a net orientation of the particles (on a length scale of the coherence length) the layer of particles will generate second harmonic light. Another means of doing this is by measuring a sample of a suspension of the particles and detecting the hyper-Rayleigh scattering. Yet another means involves the use of EFISH to determine if a candidate molecule or particle is nonlinearly active. The effect can be used to measure the hyperpolarizability of molecules in solution by using a dc field to induce alignment in the medium, and allowing SHG to be observed. This type of measurement does not require that the particle themselves be ordered at an interface, but does require that the particles be nonlinear-active and thus non-centrosymmetric.

In a specific embodiment, metal nanoparticles and assemblies thereof are modified to create biological nonlinear-active labels. The following references describe the modification metal nanoparticles and assemblies:

J. P. Novak and D. L. Feldheim, "Assembly of Phenylacetylene-Bridged Silver and Gold Nanoparticle Arrays", J. Am. Chem. Soc., 2000, 122, 3979-3980.

J. P. Novak et al., "Nonlinear Optical Properties of Molecularly Bridged Gold Nanoparticle Arrays", J. Am. Chem. Soc. 2000, 122, 12029-12030.

Vance, F W, Lemon B. I., Hupp, J. T. Enormous Hyper-Rayleigh Scattering from Nanocrystalline Gold Particle Suspensions", J. Phys. Chem. B 102:10091-93 (1999).

The following reference and references therein describe the techniques available for creating a biological label from a synthetic dye and many other molecules:

Greg T. Hermanson, Bioconjugate Techniques, Academic Press, 1996.

In a specific embodiment, nonlinear-active labels can be constructed according to well known procedures in the art to be photoactivated or photomodulated with a beam of light such that, upon irradiation of the sample with a selected beam of light, the labels become nonlinear optical active (or more or less nonlinear optical active). The beam of light can, for example, cleave a chemical bond (e.g., using UV light), well known in the art as 'caged' compounds.

Modulators

Modulators include any substance (e.g., moiety, molecule, biological component or compound) that alters the nonlinear response of a nonlinear-active species when the modulator is in proximity to the nonlinear-active species, or alters the kinetic or equilibrium properties of probe-target interactions (e.g., binding reaction). Modulators may change the rate of probe-target binding, the equilibrium constant of probe-target binding or, in general, enhance or reduce probe-target interactions. Examples of modulators are the following: inhibitors, drugs, small molecules, agonists and antagonists and Au particles. Candidate modulators can be tested for their ability to perform as modulators, e.g., in a screening process.

In a specific embodiment, target-probe interactions can be measured in the presence of some modulator of the interactions—the modulator being, for example, a small molecule, drug, or other moiety, molecule or particle which changes in some way the target-probe interactions (e.g., has some affinity for the probe and blocks or inhibits target binding). The modulator can be added before, during or after the time in which the probe-target interactions occur.

Inhibitors

Inhibitors decrease or prevent probe-target interactions Inhibitors can be any substance, e.g., moiety, molecule, compound or particle. Preferably the inhibitor competes with a known binding interaction between target and probe. Inhibitors are a form of modulator Inhibitors are also referred to herein as blocking agents or blockers.

In a specific embodiment, compounds that are potential inhibitors of an agonist to a receptor are screened by testing for removal of a conformational change induced by the agonist when the receptor and agonist are also in the presence of an inhibitor candidate (the agonist can be a natural molecule, synthetic, etc.).

Decorators

A decorator refers to a nonlinear-active substance (e.g., molecule or particle) which can be bound to targets, probes or target-probe complexes, and allow detection and discrimination among them. Ideally, a decorator should not appreciably alter or participate in the target-probe reaction itself. A decorator is distinguished from a nonlinear-active label, such as a SHG-active label, in that it possesses a specific binding affinity for the target, probe, or the target-probe complex, while an SHG-label can be attached to, for example a biological component, via specific chemical bonds or non-specific (e.g., electrostatic) means. A decorator can be used to detect probe-target complexes by its specific binding affinity (in some art, 'molecular recognition') to the targets, probes or the target-probe complexes and to thereby discriminate among targets, probes and target-probe complexes in a surface-selective nonlinear optical technique. For example, a decorator which has a stronger affinity (larger binding constant) to double-stranded DNA than single-stranded DNA can be used to detect hybridization with surface-attached probes since the amount of oriented decorator will increase as hybridization proceeds between single-stranded targets and probes. In a specific embodiment, decorators are constructs of a nonlinear-active species and another species, where the other species is a biological component (protein, antibody, etc.) and where the construct has a differential binding affinity among probes, targets and probe-target complexes to allow discrimination among them using a surface-selective nonlinear optical technique. Decorators can also be a non-natural molecules (e.g., synthetic chemical molecule, drug, etc.) with a nonlinear activity and which binds specifically (recognizes) targets, probes or target-probe complexes, and has a differential binding affinity among the three to allow for discrimination among them using a surface-selective nonlinear optical technique. In a specific embodiment, the decorator is dissolved or suspended in a solution or aqueous phase containing the target component.

Exemplary decorator molecules or particles include, but are not limited to, a biological component, a nucleic acid, protein, small molecule, biological cell, virus, liposome, receptor, agonist, antagonist, inhibitor, hormone, antibody, antigen, peptide, receptor, drug, enzyme, ligand, nucleoside, polynucleoside, carbohydrate, cDNA, hormone, allergen, cDNA, hapten, oligonucleotide, biotin, streptavidin, polynucleotide, oligosaccharide, peptide nucleic acid (PNA), or nucleic acid analog. In other non-limiting embodiments, decorators comprise a moiety in the family of, or that is, psoralen, ethidium bromide, methane phosphonate, phosphoramidate, propidium iodide, acridine, 9-aminoacridine, acridine orange, chloroquine, pyrine, echinomycin, 4',6-diamidino-2-phenylindole, dihydro chloride (DAPI), succinimidyl acridine-9-carboxylate, chloroquine, pyrine, echinomycin, 4',6-diamidino-2-phenylindole, dihydrochloride (DAPI), single-strand binding protein (SSB), tripyrrole peptides, flavopiridol, or pyronin Y.

Indicators

The following section describes indicators in detail. Indicators include nonlinear-active molecules or particles whose nonlinear optical properties or orientation near a surface or interface is modulated as the electric charge polarization, charge density or potential of the surface is modulated. In one aspect of the invention, the charge or potential of an interface is modulated by the binding of a target to probes immobilized on the surface. In another aspect, the surface electric potential of a cell is changed by a change in the ion channel properties—an opening, closing, increase or decrease in ionic permeability in response to target (ligand) binding, for instance. In another aspect of the invention, an indicator serves as a marker for imaging purposes, e.g., to image cells or tissues. An indicator preferably does not appreciably alter or participate in the target-probe reaction itself. The indicator can be dissolved or suspended in the liquid, medium, solution or aqueous phase containing the target component. An indicator preferably does not translocate into the lipid bilayer of vesicles or cells. An indicator preferably possesses freedom of movement to respond to changes in surface electric charge density or potential.

Measuring the nonlinear optical response of a glass-solvent or glass-water interface, in the presence of dissolved or suspended indicators in the water or solvent, is one means of assaying whether a candidate molecule would function as an indicator. Since glass carries a net negative charge, a candidate molecule can function as an indicator if the intensity of the nonlinear optical radiation generated at the interface in the presence of the molecule is greater than the background signal in its absence. Another means of assaying for a candidate molecule's ability as an indicator is by measuring the intensity of nonlinear optical radiation generated by a semiconductor-liquid interface as a function of applied voltage (and hence surface electric charge density) between the semiconductor and the bulk of the liquid. Yet another means is to measure the hyper-rayleigh scattering (HRS) from a solution or suspension of the indicator candidates, since if HRS is generated and the candidate itself is charged or dipolar, it should serve as an indicator.

Oxazole dye 4-[5-methoxyphenyl)-2-oxazolyl]pyridinium methanesulfonate (also known as 4PyMPO-MeMs) is an indicator that can be used, that is strongly second harmonic-active and chemically stable at neutral pH (Salafsky and Eisenthal, Chemical Physics Letters 2000, 319, 435-439). Furthermore, the Stokes shift of the fluorescence which results from two-photon absorption is large so that the second harmonic beam can readily be separated from the fluorescence. Other dyes in this family have similar properties (J. H. Hall et al., "Syntheses and Photophysical Properties of Some 5(2)-Aryl-2(5)-(4-pyridyl)oxazoles and Related Oxadiazoles and Furans", J. Heterocyclic Chem. 29, 1245 (1992)). These and other molecules, or assemblies of the molecules, can be used as indicators in the present invention. Such molecules include, but are not limited to:

5-(4-methoxyphenyl)-2-(4-methoxyphenyl)-2-(4-pyridyl) oxazole
2-(4-methoxyphenyl)-5-(4-pyridyl)oxazole
2-(4-methoxyphenyl)-5-(4-pyridyl)oxadiazole
2-(4-methoxyphenyl)-5-(4-pyridyl)furan
2-(4-pyridyl)-4,5-dihydronapthol[1,2-d]-1,3-oxazole 5-Aryl-2-(4-pyridyl)-4-R-oxazole where R is a hydrogen atom, methyl group, ethyl group or other alkyl group.
2-(4-pyridyl)cycloalkano[d]oxazole
2-(4-pyridyl)phenanthreno[9,10-d]-1,3-oxazole
6-Methoxy-4,4-dimethyl-2-(4-pyridyl)indeno[2,1-d]oxazole
4,5-Dihydro-7-methoxy-2-(4-pyridyl)napthol[1,2-d]-1,3-oxazole Other molecules or molecules of the following families which can be used as indicators, include, but are not limited to:

Merocyanines
Stilbenes
Indodicarbocyanines
Hemicyanines
Stilbazims
Azo dyes
Cyanines
Stryryl-based dyes
Methylene blue
Diaminobenzene compounds
Polyenes
Diazostilbenes
Tricyanovinyl aniline
Tricyanovinyl azo
Melamines
Phenothiazine-stilbazole
Polyimide
Sulphonyl-substituted azobenzenes
Indandione-1,3-pyidinium betaine
Fluorescein
Benzooxazole
Perylene
Polymethacrylates
Oxonol Derivatized Particle Indicators A solid microparticle or a nanoparticle of size nanometers to microns in scale including, but not limited to, a sphere (latex, polystyrene, silica, etc.) or a strip, offers a surface area which can be derivatized with a nonlinear-active moiety via chemical or electrostatic means so that the entire object has a much higher hyperpolarizability than can be obtained otherwise. For instance, nonlinear-active dyes can be ordered on silica bead surfaces via electrostatic interactions (dye is positively charged, silica surface is negatively charged) and the entire bead, if derivatized with target-reactive linkers, can then function as an indicator. If the nonlinear-active moieties can be aligned on the solid surface so that phase interference between moieties is small, the overall hyperpolarizability will scale nonlinearly (e.g., quadratically) in their number. The solid particle can vary in shape and its size can range from nanometers to microns in scale. Examples of the particles to be used include, but are not limited to, polystyrene beads and silica beads, both readily commercially available.

a. Covalent Attachment

The solid particles to be used as indicators can be surface-derivatized using a variety of chemistries available in the prior art. Nonlinear-active moieties can be covalently coupled either to the solid particles or to a derivatized layer.

For instance, polystyrene beads can be derivatized with dextran, lactose or amines (the latter case for example, via chloromethyl groups with ethylenediamine). Silica can be derivatized using organofunctional silanes, for example using trichlorosilanes or other functional silanes (such as methoxy, amine, or other functional groups), to produce surfaces with a variety of chemical functionalities. The surfaces of the derivatized beads can then be reacted with a nonlinear-active moiety via appropriate chemistry to produce the indicator.

b. Electrostatic Attachment

Nonlinear-active moieties can also be electrostatically bound to a micron- or nanometer-sized particle surface to produce indicators with large hyperpolarizabilities. A charged nonlinear-active moiety, an organic dye for example, can be oriented at a counter-charged microparticle surface, thus allowing for a net hyperpolarizability of the object when using an appropriate geometry. An example of an appropriate geometry is a microparticle sphere where the diameter is approximately the wavelength of the fundamental light, i.e. from tens of nanometers to microns so that destructive phase interference between nonlinear-active moieties on opposing faces of the sphere is minimized. The hyperpolarizability of each dye at the spheres's surface, when integrated across the entire surface of the sphere of ~wavelength of light size, is large and positive. By way of example, but not limitation, the following procedure can be used. Silica beads (~200 nm, roughly spherical) are reacted with a low concentration of 3-aminopropyltrimethoxysilane or 3-aminooctyltrimethoxysilane so that only ~5-10% of the surface silanols become covalently coupled to the silane agent. These amine groups are then reacted with the amine-reactive homobifunctional crosslinker disuccinimidyl glutarate (DSG, Pierce Chemical) to create amine-reactive linkers on ~5-10% of the bead surface. The beads are then incubated with 4-[5-methoxyphenyl)-2-oxazolyl]pyridinium methanesulfonate (also known as 4PyMPO-MeMs), a positively charged dye which binds electrostatically to the charged silanols on the surface and orients to some degree. The excess dye is removed from the beads by centrifugation. The electrostatic adsorption can be sufficiently high in some cases to immobilize the charged dye, even in the absence of a bulk concentration of it. Many nonlinear-active species are known in the art that can be used and include, but are not limited to, the following and their derivatives:

Oxazole or Oxadizole Molecules
5-aryl-2-(4-pyridyl)oxazole
2-aryl-5-(4-pyridyl)oxazole
2-(4-pyridyl)cycloalkano[d]oxazoles
Merocyanines
Stilbenes
Indodicarbocyanines
Hemicyanines
Stilbazims
Azo dyes
Cyanines
Stryryl-based dyes
Methylene blue
Diaminobenzene compounds
Polyenes
Diazostilbenes
Tricyanovinyl aniline
Tricyanovinyl azo
Melamines
Phenothiazine-stilbazole
Polyimides
Sulphonyl-substituted azobenzenes
Indandione-1,3-pyidinium betaine
Fluoresceins
Benzooxazoles
Perylenes
Polymethacrylates
Oxonols
Thiophenes
Bithiophenes In evaluating whether a species may be nonlinear-active, the following characteristics can indicate the potential for nonlinear activity: a large difference dipole moment (difference in dipole moment between the ground and excited states of the molecule), a large Stokes shift in fluorescence, an aromatic or conjugated bonding character. In further evaluating such a species, an experimenter can use a simple technique known to those skilled in the art to confirm the nonlinear activity using, for example, detection of SHG from an air-water interface or from EFISH in the absence and presence of the species in question in a medium. Once a suitable nonlinear-active species has been selected for the experiment at hand, the species can be conjugated, if desired, to a species with specificity to a biological target to produce a targeting construct used in the surface-selective nonlinear optical detection or imaging technique.

Enhancers

An enhancer as used herein refers to a substance (e.g., moiety, molecule or particle) which can enhance (increase) the cross-section of a nonlinear-active substance (e.g., moiety, molecule or particle) when placed near to it (e.g., increase the intensity of second harmonic radiation generated). Examples of the enhancement effect referred to in the art include 'resonance enhancement' and 'surface enhancement.' Enhancement of the nonlinear-active cross-section moiety, molecule or particle can occur via a resonance with an electronic transition or plasmon resonance of the enhancer. The addition of an enhancer onto, or near to, a molecule or surface, can result in the enhancer coupling to the molecule or surface, e.g., covalently, electrostatically, non-covalently, etc., or the enhancer is not coupled directly to the molecule or surface, but rather is near to the molecule or surface, e.g., enhancer adsorption on to a cell surface, causing the enhancer to increase the nonlinear response of the label on the probes.

The following (and references therein) describe the production, design and use of resonance-enhancing particles, such as metal nanoparticles, for nonlinear optical processes (SHG, Surface-enhanced resonance Raman, etc.): S, Nie and S. Emory, Science, 1997, 75, 1102; P. V. Kamat, M. Flumiani, G. V. Hartland, J. Phys. Chem. B, 1998, 102, 3123; H. Ditlbacher et al., Appl. Phys. B, 2001, DOI: 10, 1007/s003400100700; C. Sonnichsen et al., Appl. Phys. Lett., 2000, 77, 2949; B. Lamprecht et al., Appl. Phys. B, 1997, 64, 269; J. P. Novak, J. Am. Chem. Soc., 2000, 122, 12029; S. R. Emory, W. E. Haskins, S, Nie, J. Am. Chem. Soc. 1998, 120, 8009; W. P. McConnell et al., J. Phys. Chem. B 2000, 104, 8925; F. W. Vance, B. I. Lemon, J. T. Hupp, J. Phys. Chem. B 1998, 102, 10091; P. Galletto et al., J. Phys. Chem. B 1999, 103, 8706; S. R. Emory, S, Nie, J. Phys. Chem. B 1998, 102, 493

The presence of the resonance-enhancing or surface-enhancing species serves to increase the nonlinear-active cross-section of samples. Examples of resonance-enhancing species in the art are the following: metal or metallic (e.g., gold and silver) nanoparticles or colloidal particles, metal-coated particles (e.g., silver-coated latex nanospheres), aggregates or clusters of any of the aforementioned, rationally-designed clusters, chains or aggregates of the aforementioned (e.g., for symmetry-breaking: non-centrosymmetric aggregates, particles or clusters), etc.

In some instances, experimentation may be required to determine the optimal labeling strategy and/or use of enhancers or decorators for a given measurement. For instance, the coupling chemistry, reaction conditions, etc. may be adjusted empirically to determine the optimal labeling strategy. Candidates for an enhancer can be tested for their effect on a nonlinear-active species by measuring, for example, the SHG intensity of a nonlinear-active species in the absence and presence of the candidate enhancer (the enhancer can be attached to the nonlinear-active label, through a linker if necessary; or the enhancer can be brought into proximity to the label, e.g. by virtue of the probe-target reaction). The enhancer's effect on a nonlinear-active label can be made at an interface (e.g., air-water or solid-liquid) or in bulk phase under the application of an electric field (EFISH).

Molecular Beacon Analogues

The nonlinear activity of a system can also be manipulated through the introduction of nonlinear analogues to molecular beacons, that is, molecular beacon probes that have been modified to incorporate a nonlinear-active label (or modulator thereof) instead of fluorophores and quenchers. These nonlinear optical analogues of molecular beacons are referred to herein as molecular beacon analogues (MB analogues or MBA). The MB analogues to be used in the invention can be synthesized according to procedures known to one of ordinary skill in the art.

In specific embodiments, the MB analogue probes can be used according to the present invention as hybridization probes that can report the presence of complementary nucleic acid targets without having to separate probe-target hybrids from excess probes in hybridization assays and without the need to label the targets. Target labeling is not only time-consuming, but it can change the levels of targets originally present in a sample. MB analogue probes can also be used for the detection of RNAs within living cells, for monitoring the synthesis of specific nucleic acids in sealed reaction vessels, and for the construction of self-reporting oligonucleotide arrays. They can be used to perform homogeneous one-tube assays for the identification of single-nucleotide variations in DNA and for the detection of pathogens or cells immobilized to surfaces for interfacial detection.

Figure 20A:
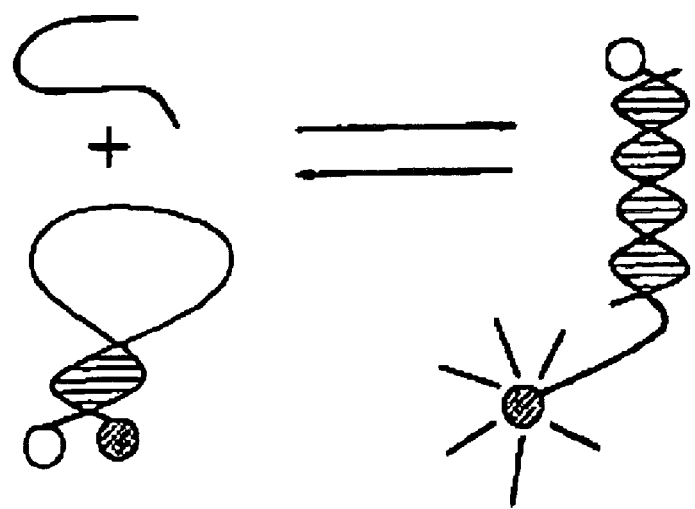
FIGS. 20A-B depict a molecular beacon that has been modified to form a nonlinear-active analogue.
Figure 20B:
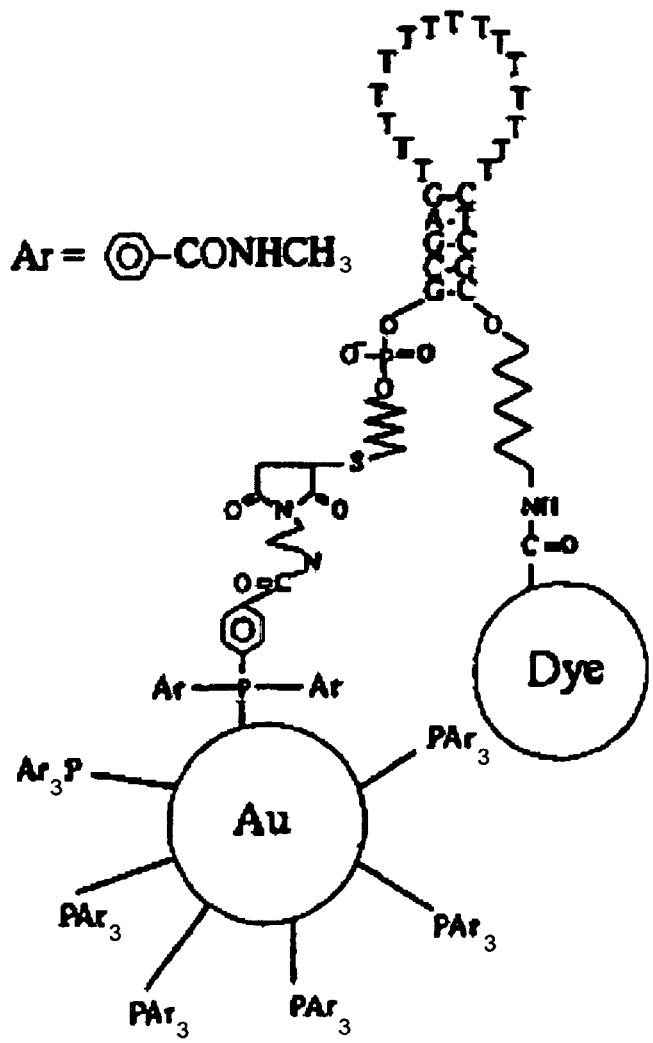

FIGS. 20A and 20B illustrate an embodiment of a MB analogue probe. A species with a hyperpolarizability capable of generating nonlinear optical radiation in response to illumination with one or more fundamental beams is attached to one end of a probe or at one location (e.g., a dye molecule, see FIG. 20B). At the other end of the probe or in another location in proximity to the nonlinear-active label, a species capable of increasing or decreasing the nonlinear optical radiation generated by a nonlinear-active label when the two species are in proximity is attached (e.g., a 10 nm gold particle, see FIG. 20B). The attachment can be via a covalent bond or through some other well known means in the art. In a specific embodiment, the nonlinear-active label is an organic dye with a hyperpolarizability such as the well known oxazole dyes and their derivatives. The oxazole dyes and their derivatives are commercially available from Molecular Probes (Eugene, Oreg.) for attachment to a variety of probes including nucleic acids using amine and sulfhydryl chemistries. A species such as a gold nanoparticle, well known for its ability to enhance the nonlinear optical radiation generated by a nonlinear-active species to which it is in proximity, can be used as the species capable of modulating the nonlinear optical radiation generated by the label. In specific embodiments, the MB analogue probes can be immobilized to a solid surface such as a planar glass surface or to the surface of microspheres, or the MB analogue probes can be used in homogeneous solution and detected using an applied electric field in an EFISH measurement. If the MBAs are immobilized to a surface, the nonlinear-active species becomes at least partially oriented at the surface and satisfies the non-centrosymmetric condition required for surface-selective nonlinear optical techniques.

The Au nanoparticle can enhance the intensity of nonlinear optical radiation, such as second harmonic generation scattered by the oxazole dye by several orders of magnitude when the nanoparticle and oxazole dye are in proximity to each other. Upon hybridization of the probe to a complementary target, the intensity of the nonlinear optical radiation decreases and this decrease can be quantitatively related to the amount of probe-target hybridization. The sensitivity of the technique is determined by, among other factors, the background nonlinear optical signal before hybridization occurs. The sequences of various targets used for testing the degree of hybridization to the probe in FIG. 20B are Target 1-4 in FIG. 20 (SEQ ID NOs: 1-4 respectively).

The present invention can be used for detection of single nucleotide polymorphisms (SNPs) in target samples because the MBA probes are highly selective in their binding of targets and a one base pair difference in sequence between probes and targets will yield a much reduced hybridization affinity compared with a target that is perfectly complementary. The MBA probe can act also as a label.

Assaying Probe-Target Interactions

Throughout the description of the present invention test molecules are also referred to as "targets," and candidate binding partners are also referred to herein as "probes." The following are examples of the types of probe-target interactions that can be assayed according to the present invention:
  i) Probe-target binding that results in a conformational change in the probe, target or both.
  ii) Probe-target binding that results in a change in the dipole moment of a nonlinear-active species, said species being the probe, target or both, as a result of probe-target binding.

Probe-target binding can also result in a combination of both conformational and dipole moment changes.

Furthermore, detection of the probe-target interactions can occur at an interface, in bulk phase (homogeneous phase), or in regions that comprise a combination of interface and bulk.

The present invention can be applied to an ensemble of molecules or to a single molecule—i.e., ensemble reaction measurements or a single-molecule reaction measurement.

In a preferred embodiment, the target is a G protein-coupled receptor (GPCR). GPCRs are one class of proteins that undergo a conformational change when activated by a ligand and are thus amenable to study using the present invention. In this case, if the GPCR is not intrinsically nonlinear-active, the protein is labeled using a nonlinear-active label, and the conformational change is detected or queried for via a change in the orientation of the nonlinear-active label. The GPCRs can be attached to a surface and the conformational change that results when a ligand activates the receptor causes a change in the orientation of the label and thus a change in properties of the nonlinear optical beams (e.g., second harmonic generation) such as intensity, wavelength or polarization. A background signal can be measured before exposure of the sample to a ligand, if desired.

In some cases, binding of a component to a receptor will lead to a change in measured nonlinear optical properties even though the receptor is not activated. For example, this can be due to an interaction between the component and the receptor in the bound complex which alters the orientation of a label attached to the receptor. A control can be performed, if desired, to assign measured changes in nonlinear optical properties to binding or activation of components to a given receptor. For example, a component which is known to bind to a given receptor but not to produce a conformational change can be used as a control of the label reaction; if any measured change in label orientation is due only to receptor activation, the position of the label can be changed by changing the conjugation chemistry of the label and/or genetically modifying the receptor to introduce new labeling sites.

For example, receptors can be labeled with a nonlinear-active label that possesses, on average, an orientation (or orientation of hyperpolarizability) of some angle $\theta$ with respect of the surface plane (e.g., host cell membrane). Upon binding and/or activation to some ligand, the average label angle can shift to angle P with respect to the surface plane. Even small shifts in angle as a result of receptor binding or activation can cause substantial changes in a property of the measured nonlinear optical light (e.g., intensity of the nonlinear light). For example, if the intensity of the nonlinear optical light generated is proportional to the component of the hyperpolarizability that is normal to the membrane plane, then the percentage change of intensity upon a shift is: $[\cos(\theta)/\cos(\beta)]^2$ with the nonlinear intensity dependent quadratically on the normal component of the hyperpolarizability. For example, assuming a delta function in hyperpolarizability orientation, if $\theta \rightarrow \beta$ is a change of 25 degrees to 30 degrees, the nonlinear optical intensity will decrease about 9%.

In some instances, some experimentation may be required to determine the optimal labeling strategy and/or use of enhancers or decorators for a given measurement. For instance, the coupling chemistry, reaction conditions, etc. may need to be adjusted empirically to determine the optimal labeling strategy.

Alternatively, the target molecules can be solubilized and, using their intrinsic dipole moments, poled by an electric field in solution phase; if the target possesses a hyperpolarizability (i.e., is nonlinear-active, either intrinsically or made so by attachment of a nonlinear-active label), a nonlinear optical signal will be generated via EFISH technique, and this signals serves as the background. Upon addition of a ligand (i.e., a probe) that activates the target molecule, a conformational change will occur. If this conformational change does not result in an appreciable dipole moment change in the target molecule, the number and net orientation of the target molecules will not change appreciably. If, however, this conformational change is passed to the nonlinear-active moiety, its overall orientation will change, resulting in a change in measured nonlinear optical properties. If the binding of a ligand to the target molecules results in an appreciable dipole moment change of the nonlinear-active target molecule, the number of aligned target molecules in the applied field will change, resulting in-change in measured nonlinear optical properties. The number of aligned molecules in an applied electric field in solution is dependent on the dipole moment of the molecules. An equation used to model the dependence is the Langevin equation: $N=N_0 \exp(-\mu E/kT)$ where N is the number of aligned species, $\mu$ is their dipole moment, E is the electric field magnitude parallel to the dipole moment, $N_0$ the number of molecules exposed to the field, k is the Boltzmann constant and T is the temperature in Kelvin. Changes in dipole moment as a result of probe-target interactions can lead to large changes in the number of aligned molecules and thus large changes in the intensity of nonlinear optical light generated by the molecules. For example, a probe with a nonlinear-active label and a given dipole moment binds to a target; the resulting probe-target complex with a larger or smaller dipole moment leads to a change in intensity of the generated nonlinear light. Measured changes as a result of binding can also be used to calculate binding conformations between molecules if the position and amount of charge is well known on each molecule (e.g., as is often the case with proteins, whose crystal structure is known).

The above illustrations are exemplary of any probe-target interaction that results in a change in dipole moment or conformational change. Ion channel proteins are examples of another important class of proteins that undergo conformational change in response to activation and are also amenable to study using the present invention.

Surface-selective nonlinear optical techniques are also coherent techniques, meaning that the fundamental and nonlinear beams have well-defined phase relationships, and the wavefronts of a nonlinear beam in a macroscopic sample (within the coherence length) are in phase. These properties offer a number of advantages useful for surface or high-throughput studies in which, for example, either a single surface or a microarray surface is examined. An apparatus using nonlinear optical surface-selective-based detection, such as with second harmonic generation, requires minimal collection optics since generation of the nonlinear light only occurs at the interface and thus, in principle, allows extremely high depth discrimination and fast scanning Probe-target interactions (e.g., a binding reaction, a conformational change, etc.) can be correlated with the present invention to the following measurable information, for example:

i) the intensity of the nonlinear or fundamental light.
ii) the wavelength or spectrum of the nonlinear or fundamental light.
iii) position of incidence of the fundamental light on the surface or substrate (e.g., for imaging).
iv) the polarization of the nonlinear light
v) the time-course of i), ii), iii) or iv).
vi) one or more combinations of i), ii), iii), iv) and v).

The advantages of the present invention are enumerated as follows:

i) Sensitive and direct dependence on the orientation and/or dipole moment of the nonlinear-active species in a sample, useful for detection of conformational changes in probes and binding that results in an appreciable change in the dipole moment of the nonlinear-active species (i.e., probe, target or both).
ii) Higher signal to noise (lower background) than fluorescence-based detection since surface-selective nonlinear optical light is generated only at surfaces that create a non-centrosymmetric situation, or in homogeneous phase under application of an electric field to induce the non-centrosymmetry surface-selective nonlinear optical light detection of a surface has a very narrow 'depth of field'. Sources of fluorescence in fluorescence-based detection schemes include that from materials in the field of view but not in the focal plane, autofluorescence, and contamination of the emitted fluorescence with stray excitation light; these are not sources of background nonlinear optical radiation.
iii) The nonlinear optical technique is useful when the presence of a liquid solution is required for the measurement, i.e. where the binding process can be obviated or disturbed by a wash-away step. This aspect of the invention can be useful for equilibrium measurements (free energy, binding constants, etc.), which require the presence of bulk species or kinetics measurements with measurements made over a period of time.
iv) Lower photobleaching and heating effects than those that occur in fluorescence—the two-photon absorption cross-section is much lower than the one-photon cross-section in a molecule and the nonlinear optical technique involves scattering, not absorption.
v) A minimum of collection optics is needed and higher signal to noise is expected since the fundamental and nonlinear beams (e.g., second harmonic) have well-defined incoming and outgoing directions with respect to the interface. This is advantageous compared to fluorescence-based detection in which the fluorescence is emitted isotropically and there may be a large auto-fluorescence background out of the plane of interest (e.g., the interface containing the probes).
vi) Ease of use with beads, biological cells, liposomes or other particles whose non-planar surface makes an interface with the supporting medium, solution, etc.
vii) Convenience of discriminating between binding of targets to probes from actual activation of probes (e.g., a receptor) by a target.
viii) The binding process between probes and targets can be performed in the presence of one or more small molecules, drugs, blocking agents, or other components which affect properties of the probe-target binding process, e.g. equilibrium constants, kinetics of binding, etc.

In an embodiment, using surface arrays, arrays can be constructed according a plurality of methods found in the art. For DNA microarrays, most are prepared with one of three non-standard approaches (S. C. Case-Green et al., Curr. Opin. Chem. Biol. 2 (1998), 404): Affymetrix, Inc. probe arrays are prepared using patterned, light-directed combinatorial chemical synthesis (S. A. Fodor, Science 277 (1997), 393); spotted arrays can be made according to D. H. Duggan et al., Nature Genet. 21 (Suppl.) (1999), 10; M. Schena et al., Science 270 (1995), 467; P. O. Brown and D. Botstein, Nature Genet. 21 (Suppl.) (1999), 33; and L. McAllister et al., Am. J. Hum. Genet. 61 (Suppl.) (1997), 1387; ink-jet techniques can also be used to synthesize oligonucleotides base by base through sequential solution-based reactions on an appropriate substrate (A. P. Blanchard et al., Biosens. And Bioelectron. 11 (1996) 687—relevant portions of all of which references are incorporated by reference herein).

For example, nucleic acid, oligo- or nucleotide arrays can be constructed according to U.S. Pat. No. 6,110,426, U.S. Pat. Nos. 5,143,854 6,110,426—relevant portions of which are incorporated by reference herein, U.S. Pat. No. 5,143,854—relevant portions of which are incorporated by reference herein or Fodor et al., "Light-directed Spatially-addressable Parallel Chemical Synthesis," Science, 1991, 251, 767-773. Soluble protein arrays can be constructed according to R. Ekins, F. W. Chu, Trends in Biotechnology, 1999, 17, 217, relevant portions of which are incorporated by reference herein. Membrane proteins arrays can be constructed by micropatterning of fluid lipid membranes according, for example, to the method of Groves, J. T., Ulman, N., Boxer, S. G., "Micropatterning fluid bilayers on solid supports", Science, 1997, 275, 651-3 (relevant portions of which are incorporated by reference herein). The array substrate can be composed of glass, silicon, indium tin oxide, or any other substrate known in the art. The surface array under study can contain physical barriers between elements so that the elements (and their biomolecules) can remain in isolation from each other during a chemical reaction step. The array locations can consist of different probes, the same probes everywhere, or some combination thereof. The array can also be constructed on the underside of a prism allowing for total internal reflection of the beam and evanescent generation of the nonlinear light. Or an array substrate can be brought into contact with a prism with the same result.

An electrophoretic system can also be used in conjunction with the surface array, for example to deliver reagents or biological components to one or a plurality of locations using flow channels or microcapillaries. The sample can include an array of microcapillary channels, each distinct from the other and each allowing a target-probe reaction to occur; the imaging technique would then consist of array elements, each one a microcapillary channel or reaction chamber into which the channel feeds or drains.

The polarization of the fundamental and nonlinear beams can be selected with polarizing optics elements. By analyzing the intensity of the nonlinear beam as a function of fundamental and nonlinear polarization, more information (e.g., higher signal to noise) about the probe-target complexes can be obtained. Furthermore, by selecting and analyzing the polarization of the fundamental or nonlinear optical radiation, background radiation can be reduced or signal intensity enhanced.

Detection can be accomplished with the use of multiple internal reflection plates (N. J. Harrick, "Internal Reflection Spectroscopy", John Wiley & Sons, Inc., New York, 1979—relevant portions of which are incorporated by reference herein) allowing the fundamental beam to make multiple contacts with the array surface, thus increasing the intensity of the generated nonlinear light. Another alternative is to construct an optical cavity with the array surface on one side and a lossy coupler at one end to permit the output coupling of the nonlinear light, creating an optical microcavity which would allow the buildup of very high intensities under resonance and thus increase the amount of nonlinear light generated.

Polynucleotide arrays can be used as probes. Where oligonucleotides are targets or probes, preferably a nonlinear-active label is attached to the 5' or 3' termini. There are many linking moieties and methodologies for attaching molecules which can be nonlinear-active labels to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoraridate linkages); Sproat et al., Nucleic Acids Research, 15: 4837 (1987) (5' mercapto group); Nelson et al., Nucleic Acids Research, 17: 7187-7194 (1989) (3' amino group); and the like, relevant portions of which are incorporated by reference herein.

Preferably, commercially available linking moieties are employed that can be used to a label to an oligonucleotide during synthesis, e.g., available from Clontech Laboratories (Palo Alto, Calif.). In a specific embodiment, rhodamine and fluorescein dyes can be conveniently attached to the 5' hydroxyl of an oligonucleotide at the conclusion of solid phase synthesis by way of dyes derivatized with a phosphoramidite moiety, e.g., Woo et al., U.S. Pat. No. 5,231,191; and Hobbs, Jr., U.S. Pat. No. 4,997,928, relevant portions of which are incorporated by reference herein.

Preferable, the oligonucleotides are present on arrays.

Protein arrays can be used to determine whether a given target protein binds to the immobilized probe protein on the surface; these arrays can also be used to study small molecule binding to the probe proteins. Protein arrays can be prepared by the method of G. MacBeath and S. L. Schreiber, "Printing Proteins as Microarrays for High-Throughput Function Determination", Science 2000, 289, 1760-1763, for example, to determine whether a given target protein binds to the immobilized probe protein on the surface.

The surface on which the probes are formed may be composed from a wide range of material, either biological, non-biological, organic, inorganic, or a combination of any of these, existing as particles, strands, precipitates, gels, sheets, tubing, spheres, containers, capillaries, pads, slices, films, plates, slides, etc. The surface may have any convenient shape, such as a disc, square, sphere, circle, etc. The surface is preferably flat but may take on a variety of alternative surface configurations. For example, the surface may contain raised or depressed regions on which a sample is located. The surface and its surface preferably form a rigid support on which the sample can be formed. The surface and its surface are also chosen to provide appropriate light-absorbing characteristics. For instance, the surface may be a polymerized Langmuir Blodgett film, functionalized glass, Si, Ge, GaAs, GaP, $Si_xO_y$, $Si_xN_y$, modified silicon, or any one of a wide variety of gels or polymers such as (poly) tetrafluoroethylene, (poly)vinylidenedifluoride, polystyrene, polycarbonate, or combinations thereof. Other surface materials will be readily apparent to those of skill in the art upon review of this disclosure. In a preferred embodiment the surface is flat glass or silica.

According to some embodiments, the surface of the substrate is etched using well known techniques to provide for desired surface features. For example, by way of the formation of trenches, v-grooves, mesa structures, or the like, the synthesis regions may be more closely placed within the focus point of impinging light. The surface may also be provided with reflective "mirror" structures for maximization of emission collected therefrom.

The chemical identity of the probes (e.g., protein structure or oligonucleotide sequence) can vary from site to site across the solid surface, or the same probe can uniformly cover the surface. Targets can be of a single identity or a combination of targets with different identities.

In a specific embodiment, the kinetics of probe-target binding reactions are measured as a function of target concentration. In this embodiment, the time course of the intensity and/or spectrum of the nonlinear optical light are measured. The measured information is converted into a time course of bound target concentration (e.g., probe-target concentration in mM/s or EM/s). Drugs or modulators of the probe-target binding equilibrium or kinetic rate of formation can be used so as to compare the effect of the added substance on the probe-target reactions.

Various art not involving the use of a surface-selective nonlinear optical technique contains relevant portions for the present invention and the following exemplary list and their references therein is referenced herein: King et al., U.S. Pat. No. 5,633,724 for the scanning and analysis of the scans; Fork et al., U.S. Pat. No. 6,121,983 for the multiplexing of a laser to produce a laser array suitable for scanning; Foster, U.S. Pat. No. 5,485,277; Fodor et al., U.S. Pat. No. 5,324,633 and Fodor et al., U.S. Pat. No. 6,124,102 for a substrate containing an array of attached probes and for the analysis of scans to determine kinetic and equilibrium properties of a binding reaction between probes and targets; Kain et al., U.S. Pat. No. 5,847,400 for laser scanning of a substrate; King et al., U.S. Pat. No. 5,432,610 for an optical resonance cavity for power build-up; Walt et al., U.S. Pat. No. 5,320,814, Walt et al., U.S. Pat. No. 5,250,264, Walt et al., U.S. Pat. No. 5,298,741, Walt et al., U.S. Pat. No. 5,252,494, Walt et al., U.S. Pat. No. 6,023,540, Walt et al., U.S. Pat. No. 5,814,524, Walt et al., U.S. Pat. No. 5,244,813 for fiber-optic-based apparatus; Fiekowsky et al., U.S. Pat. No. 6,095,555 for imaging and software-based analysis of images; Stem et al., U.S. Pat. No. 5,631,734 for data acquisition; Stimson et al., U.S. Pat. No.

6,134,002 for confocal imaging techniques; Sampas, U.S. Pat. No. 6,084,991 for CCD-based imaging techniques; Stem et al., U.S. Pat. No. 5,631,734 for photolithographical preparation of probes attached to surfaces; Shalon et al., U.S. Pat. No. 6,110,426 for methods and apparatus for creating attached probes on a surface; Slettnes, U.S. Pat. No. 6,040,586 for position-based scanning techniques; Trulson et al, U.S. Pat. No. 6,025,601 for methods of imaging probe-target binding on a surface.

Cells Attached to Surfaces and Microarrays of Cells

This section outlines some of the methods concerned with interfacing biological cells with surfaces and fabricating arrays of biological cells on surfaces, which can be used in the assays of the present invention. Many methods have been described for making uniform micro-patterned arrays of cells for other applications, using for example photochemical resist-photolithograpy. (Mrksich and Whitesides, Ann. Rev. Biophys. Biomol. Struct. 25:55-78, 1996). According to this photoresist method, a glass plate is uniformly coated with a photoresist and a photo mask is placed over the photoresist coating to define the "array" or pattern desired. Upon exposure to light, the photoresist in the unmasked areas is removed. The entire photolithographically defined surface is uniformly coated with a hydrophobic substance such as an organosilane that binds both to the areas of exposed glass and the areas covered with the photoresist. The photoresist is then stripped from the glass surface, exposing an array of spots of exposed glass. The glass plate then is washed with an organosilane having terminal hydrophilic groups or chemically reactable groups such as amino groups. The hydrophobic organosilane binds to the spots of exposed glass with the resulting glass plate having an array of hydrophilic or reactable spots (located in the areas of the original photoresist) across a hydrophobic surface. The array of spots of hydrophilic groups provides a substrate for non-specific and non-covalent binding of certain cells, including those of neuronal origin (Klienfeld et al., J. Neurosci. 8:4098-4120, 1988). Reactive ion etching has been similarly used on the surface of silicon wafers to produce surfaces patterned with two different types of texture (Craighead et al., Appl. Phys. Lett. 37:653, 1980; Craighead et al., J. Vac. Sci. Technol. 20:316, 1982; Suh et al. Proc. SPIE 382:199, 1983).

In another method based on specific yet non-covalent interactions, photoresist stamping is used to produce a gold surface coated with protein adsorptive alkanethiol. (Singhvi et al., Science 264:696-698, 1994). The bare gold surface is then coated with polyethylene-terminated alkanethiols that resist protein adsorption. After exposure of the entire surface to laminin, a cell-binding protein found in the extracellular matrix, living hepatocytes attach uniformly to, and grow upon, the laminin coated islands (Singhvi et al. 1994). An elaboration involving strong, but non-covalent, metal chelation has been used to coat gold surfaces with patterns of specific proteins (Sigal et al., Anal. Chem. 68:490-497, 1996). In this case, the gold surface is patterned with alkanethiols terminated with nitriloacetic acid. Bare regions of gold are coated with tri(ethyleneglycol) to reduce protein adsorption. After adding $Ni^{2+}$, the specific adsorption of five histidine-tagged proteins is found to be kinetically stable.

More specific uniform cell-binding can be achieved by chemically crosslinking specific molecules, such as proteins, to reactable sites on the patterned substrate (Aplin and Hughes, Analyt. Biochem. 113:144-148, 1981). Another elaboration of substrate patterning optically creates an array of reactable spots. A glass plate is washed with an organosilane that chemisorbs to the glass to coat the glass. The organosilane coating is irradiated by deep UV light through an optical mask that defines a pattern of an array. The irradiation cleaves the Si—C bond to form a reactive Si radical. Reaction with water causes the Si radicals to form polar silanol groups. The polar silanol groups constitute spots on the array and are further modified to couple other reactable molecules to the spots, as disclosed in U.S. Pat. No. 5,324,591, incorporated by reference herein. For example, a silane containing a biologically functional group such as a free amino moiety can be reacted with the silanol groups. The free amino groups can then be used as sites of covalent attachment for biomolecules such as proteins, nucleic acids, carbohydrates, and lipids. Other methods for patterning the adhesion of mammalian cells to surfaces using self-assembled monolayers on a surface include Lopez et al., "Convenient Methods for Patterning the Adhesion of Mammalian Cells to Surfaces Using Self-Assembled Monolayers of Alkanethiolates on Gold," J. Am. Chem. Soc., 1993, 115, 5877-5878, Georger et al., "Coplanar Patterns of Self-assembled Monolayers for Selective Cell-adhesion and Outgrowth," Thin Solid Films 210 (1-2): 716-719 Apr. 30, 1992, and Spargo et al., PNAS 91 (23): 11070-11074 (1994).

The non-patterned covalent attachment of a lectin, known to interact with the surface of cells, to a glass substrate through reactive amino groups has been demonstrated (Aplin and Hughes, Analyt. Biochem. 113:144-148, 1981). The optical method of forming a uniform array of cells on a support requires fewer steps and is faster than the photoresist method, (i.e., only two steps), but it requires the use of high intensity ultraviolet light from an expensive light source.

Cells can also be cultured or grown on surfaces that require no additional derivatization. Surfaces of this type well known in the art include Becton-Dickinson Falcon plates and others.

In all of these methods the resulting array of cells or surface-attached cell layer is uniform. In the photoresist method, cells bind to the array of hydrophilic spots and/or specific molecules attached to the spots, which, in turn, bind cells. Thus cells bind to all spots in the array in the same manner. In the optical method, cells bind to the array of spots of free amino groups by adhesion. Methods for attaching a variety of cell types to the same substrate for simultaneously binding against these cell types also exist and can be used.

Nucleic Acid Arrays

Nucleic acid arrays are useful in a number of biological and clinical studies in which one or more genes are analyzed in parallel using the array. Genetic disease is often caused by genes that are inappropriately transcribed—either too much or too little—or which are missing altogether. Such defects are especially common in cancers, which can occur when regulatory genes are deleted, inactivated, or become constitutively active. Unlike some genetic diseases (e.g. cystic fibrosis) in which a single defective gene is always responsible, cancers that appear clinically similar can be genetically heterogeneous. For example, prostate cancer (prostatic adenocarcinoma) may be caused by several different, independent regulatory gene defects even in a single patient. In a group of prostate cancer patients, every one may have a different set of missing or damaged genes, with differing implications for prognosis and treatment of the disease.

Comparative hybridization can serve two purposes in studying cancer: it can pinpoint the transcription differences responsible for the change from normal to cancerous cells, and it can distinguish different patterns of abnormal transcription in heterogeneous cancers. Understanding the diverse basis of a cancer is crucial for inventing therapies targeted to the different varieties of the disease, so that each patient receives the most appropriate and effective treatment.

Cancers are common examples of genetically heterogeneous diseases, but they are by no means the only ones. Diabetes, heart disease, and multiple sclerosis are among the diseases for which genetic risk factors are known to be heterogeneous.

Peptide-Nucleic Acids

In an alternative embodiment, peptide nucleic acids or oligomers, which are analogs of nucleic acids in which, for example, the peptide-like backbone is replaced with an uncharged backbone, can be used with the present invention. PNAs are well known in the art. References below give extensive reviews of the use of these nucleic acid analogs in a wide range of applications, including surface and array-based hybridization wherein PNAs are attached to surfaces and allowed to bind with sequence-complementary DNAs or RNAs.

For instance, oligomers of PNA can be used as the surface-attached probe components instead of DNA oligomers. A key advantage to using PNAs is that the hybridization reaction with DNAs or RNAs, for example, (containing charged phosphate groups) is only weakly dependent (e.g., the melting temperature) on ionic strength because there is much less charge repulsion as found with conventional DNA-DNA, etc. hybridization. Thus, one can use the surface-selective nonlinear optical technique to follow a probe-target hybridization at any desired ionic strength. The PNAs are commercially available (for instance via Applied Biosystems, Foster City, Calif.) or other analogs of DNA can be synthesized and used.

The following references are broad reviews of the use of PNAs:

Nielsen, et al. "Peptide nucleic acids—(PNA): Oligonucleotide analogues with a polyamide backbone" Antisense Research and Applications (1992) 363-372

Nielsen, et al. "Peptide nucleic acids (PNAs): Potential Antisense and Anti-gene Agents." Anti-Cancer Drug Design 8 (1993) 53-63

Buchardt, et al. "Peptide nucleic acids and their potential applications in biotechnology" TIBTECH 11 (1993) 384-386

Nielsen, P. E., Egholm, M. and Buchardt, O. "Peptide Nucleic Acid (PNA). A DNA mimic with a peptide backbone" Bioconjugate Chemistry 5 (1994) 3-7

Nielsen "Peptide nucleic acid (PNA): A lead for gene therapeutic drugs" Antisense Therapeutics 4 (1996) 76-84

Nielsen, P. E. "DNA analogues with nonphosphodiester backbones" Annu. Rev. Biophys. Biomol. Struct. 24 (1995) 167-183

Hyrup, B. and Nielsen, P. E. "Peptide Nucleic Acids (PNA): Synthesis, Properties and Potential Applications" Bioorg. Med. 4 (1996) 5-23

Mesmaeker, A. D., Altman, K.-H., Waldner, A. and Wendeborn, S. "Backbone modifications in oligonucleotides and peptide nucleic acid systems" Curr. Opin. Struct. Biol. 5 (1995) 343-355

Noble, et al. "Impact on Biophysical Parameters on the Biological Assessment of Peptide Nucleic Acids, Antisense Inhibitors of Gene Expression" Drug. Develop. Res. 34 (1995) 184-195

Dueholm, K. L. and Nielsen, P. E. "Chemistry, properties, and applications of PNA (Peptide Nucleic Acid)" New J. Chem. 21 (1997) 19-31

Knudsen and Nielsen "Application of Peptide Nucleic Acid in Cancer Therapy" Anti-Cancer Drug 8 (1997) 113-118

Nielsen, P. E. "Design of Sequence-Specific DNA-Binding Ligands" Chem. Eur. J. 3 (1997) 505-508

Corey "Peptide nucleic acids: expanding the scope of nucleic acid recognition" TIBTECH 15 (1997) 224-229

Nielsen, P. E. and Orum, H. "Peptide nucleic acid (PNA), a new molecular tool." In Molecular Biology Current Innovations and Future Trends, Part 2. Horizon Scientific Press, (1995) 73-89

Nielsen, P. E. and Haaima, G. "Peptide nucleic acid (PNA). A DNA mimic with a pseudopeptide backbone" Chem. Soc. Rev. (1997) 73-78

Ørum, H., Kessler, C. and Koch, T. "Peptide Nucleic Acid" Nucleic Acid Amplification Technologies: Application to Disease Diagnostics (1997) 29-48

Wittung, P., Nielsen, P. and Norden, B. "Recognition of double-stranded DNA by peptide nucleic acid" Nucleosid. Nucleotid. 16 (1997) 599-602

Weisz, K. "Polyamides as artificial regulators of gene expression" Angew. Chem. Int. Ed. Eng 36 (1997) 2592-2594

Nielsen, P. E. "Structural and Biological Properties of Peptide Nucleic Acid (Pna)" Pure & Applied Chemistry 70 (1998) 105-110

Nielsen, P. E. "Sequence-specific recognition of double-stranded DNA by peptide nucleic acids" Advances in DNA Sequence-Specific Agents 3 (1998) 267-278

Nielsen "Antisense Properties of Peptide Nucleic Acid" Handbook of Experimental Pharmacology 131 (1998) 545-560

Nielsen "Peptide Nucleic Acids" Science and Medicine (1998) 48-55

Uhlmann, E. "Peptide nucleic acids (PNA) and PNA-DNA chimeras: from high binding affinity towards biological function" Biol Chem 379 (1998) 1045-52

Wang "DNA biosensors based on peptide nucleic acid (PNA) recognition layers. A review" Biosens Bioelectron 13 (1998) 757-62

Uhlmann, E., Peyman, A., Breipohl, G. and Will, D. W. "PNA: Synthetic polyamide nucleic acids with unusual binding properties" Angewandte Chemie-International Edition 37 (1998) 2797-2823

Nielsen, P. E. "Applications of peptide nucleic acids" Curr Opin Biotechnol 10 (1999) 71-75

Bakhtiar, R. "Peptide nucleic acids: deoxyribonucleic acid mimics with a peptide backbone" Biochem. Educ. 26 (1998) 277-280

Lazurkin, Y. S. "Stability and specificity of triplexes formed by peptide nucleic acid with DNA" Mol. Biol. 33 (1999) 79-83

Nielsen and Egholm "Peptide Nucleic Acids: Protocols and Applications" (1999) 266 pp.

Eldrup and Nielsen "Peptide nucleic acids: potential as antisense and antigene drugs" Adv. Amino Acid Mimetics Peptidomimetics 2 (1999) 221-245

Bentin, T. and Nielsen, P. E. "Triplexes involving PNA" Triple Helix Form. Oligonucleotides (1999) 245-255

Falkiewicz, B. "Peptide nucleic acids and their structural modifications" Acta Biochim. Pol. 46 (1999) 509-529.

The following references are descriptions of the use of PNAs in array-based detection, including means for attaching the PNA probes to the solid surface.

Hoffmann, R., et al. "Low scale multiple array synthesis and DNA hybridization of peptide nucleic acids" Pept. Proc. Am. Pept. Symp., 15th (1999) 233-234

Matysiak, S., Hauser, N. C., Wurtz, S, and Hoheisel, J. D. "Improved solid supports and spacer/linker systems for the synthesis of spatially addressable PNA-libraries" Nucleosides Nucleotides 18 (1999) 1289-1291.

Additional Embodiments

The drawings illustrate various specific embodiments of an apparatus and sample using second or higher harmonic, sum or difference frequency generation.

FIG. 1 illustrates an embodiment wherein second harmonic light is generated by reflecting incident fundamental light from the surface. Light source 5 provides the fundamental light necessary to generate second harmonic light at the sample. Typically this will be a picosecond or femtosecond laser, either wavelength tunable or not tunable, and commercially available. Light at the fundamental frequency (w) exits the laser and its polarization is selected using, for example a half-wave plate 10 appropriate to the frequency and intensity of the light (e.g., available from Melles Griot, Oriel or Newport Corp.). The beam is then focused by lens 15 and passes through a pass filter 20 designed to pass the fundamental light but block the nonlinear light (e.g., second harmonic). This filter is used to prevent back-reflection of the second harmonic beam into the laser cavity which can cause disturbances in the lasing properties. The beam is reflected from a mirror 25 and impinges at a specific location and with a specific angle θ on the surface. The mirror 25 can be scanned if required using a galvanometer-controlled mirror scanner, a rotating polygonal mirror scanner, a Bragg diffractor, acousto-optic deflector, or other means known in the art to allow control of a mirror's position. The sample surface 30 can be mounted on an x-y translation stage 35 (computer controlled) to select a specific location on the surface for generation of the second harmonic beam. The surface can be glass, plastic, silicon or any other solid surface that reflects the fundamental or second harmonic beams. The sample surface can be enclosed and the surface in contact with liquid. Furthermore, the sample 30 can be fed or drained by microcapillary or other liquid-transporting channels (not shown), pumps or electrophoretic elements, and these devices can be computer-controlled. The fundamental and the second harmonic outgoing beams (at specific angles with respect to the surface, i.e., $\theta_1$—they are typically nearly colinear in direction) then reflected from the surface and the fundamental is filtered using a pass-filter 45 for the second harmonic beam, leaving only the harmonic beam (2ω). The second harmonic is reflected from mirror 40, its polarization selected if necessary by polarizing optic 50, and is focused using a lens 55 onto a detector 60. The lenses 15 and 55 can also be any combination of lenses known in the art for focusing or beam shaping. If required, a monochromator 60 can also be used to select a specific wavelength within the spectral band of the second harmonic beam. The detector can be a photomultiplier tube, a CCD array, or any other detector device known in the art for high sensitivity. For instance, a photomultiplier tube operated in single-photon counting mode can be used. At the detector, the light generates a voltage proportional to its intensity. Data is recorded for each location on the array surface as it is translated by the stage, scanned (or a combination thereof) and an image is built up of the second harmonic intensity generated from each region on the surface.

Applicant envisions the use of sum or difference frequencies, where an apparatus set-up similar to FIG. 1 could be used, with the single light source 5 replaced by two light sources with two fundamental light beams at frequencies $\omega_1$, and $\omega_2$. The sum or difference frequency (Ω) would then be $\Omega = \omega_1 \pm \omega_2$. In the case where the sample surfaces are arrays comprised of discrete elements, a single element or more than one in parallel can be addressed with the fundamental light. Furthermore, detection can be made on a single element or many in parallel depending on the specific apparatus set-up.

Figure 2:
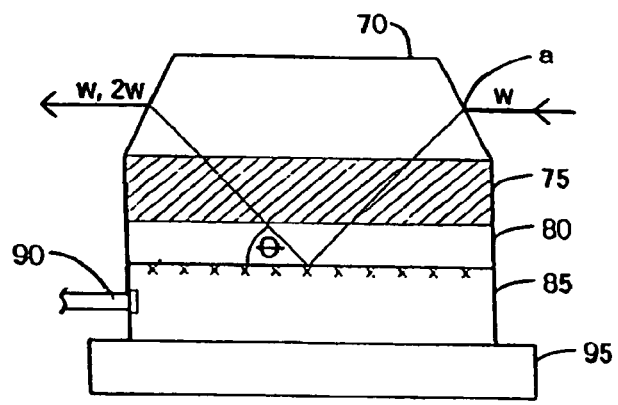
FIG. 2 depicts one embodiment of an apparatus in which the mode of generation and collection of the second harmonic light is by total internal reflection through a prism. The prism is coupled by an index-matching material to a substrate with surface-attached probes.

FIG. 2 illustrates an embodiment in which total internal reflection (evanescent wave generation) is used to generate the second harmonic light. Fundamental light (ω) is directed on to the surface of a prism element 70. The beam is refracted at position (a) and passes through the prism, through an index matching film 75 and impinges on substrate 80. Prism 70 and substrate 80 are made of optically transparent materials and are preferably of the same type. Prism 70 can be a Dove prism or any other element which can support evanescent fields (e.g., waveguides, fibers and thin metallic films). The refractive index matching film 75 can be an oil, but is preferably a compressible optical polymer such as those disclosed by Sjodin, "Optical interface means", PCT publication WO 90/05317, 1990. The prism 75 and the substrate 80 can also be a unitary, integral piece made of the same material (i.e., without the index matching film). An evanescent wave is generated at the interface between 80 and the medium in sample compartment 85 according to the indices of refraction in 80 and 85 and the angle of incidence of the beam at their interface. The electric field amplitude decays exponentially away from the substrate surface with a 1/e length ranging from nanometers to microns depending on several factors, including the surface electric potential, the counterion density in the sample compartment (if any). The sample compartment can be filled with air, a gas, or a liquid such as a solution or water. The 'x' marks on the surface of 80 facing the sample compartment emphasize that the sample of interest (e.g., fabricated probes) are placed on this side. Substrate 80 can be a 'chip' which can be slid out between 75 and 85, allowing for measurement of different substrates. Element 90 in the drawing refers to a port in the sample compartment for drawing liquid or gases in and out of the compartment, for instance by pumps, electrostatic means, etc. The entire sample assembly can be mounted on an x-y translation stage 95 if necessary.

Figure 3:
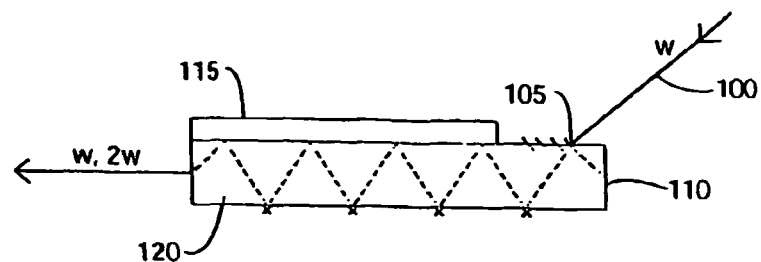
FIG. 3 depicts one embodiment of an apparatus in which the mode of generation and collection of the second harmonic light is by total internal reflection through a wave-guide with multiple reflections as denoted by the dashed line inside the wave-guide.

FIG. 3 illustrates an embodiment in which a slab-dielectric waveguide is used to deliver the fundamental light to the sample surface (the light beams are generated, directed and detected as in Drawing I with elements 1-5 and 8-13). A parallel plate or dielectric waveguide can be used to couple the fundamental light into a waveguide propagating mode. The drawing shows two slabs (110 and 115) and region (120). If the indices of refraction of slab 115 and region 120 are less than the index of refraction of the light (for both fundamental and second harmonic), a waveguiding mode can be developed. This mode produces multiple internal reflections at the substrate which can be used to increase the amount of second harmonic light generated by the interface. The fundamental beam 100 can be coupled into the waveguide 110 using a diffraction grating 105 scribed or embossed on the top surface of the waveguide, for example. The fundamental is propagated along the length of the waveguide and makes multiple total internal reflections at the top and bottom surfaces. The 'x' marks on substrate 110 denote the surface sample to be measured (i.e., containing the probes). If this interface generates significantly more second harmonic light than the interface between materials 110 and 115, the light intensity can be neglected. For example, if SH-labeled targets are bound to immobilized probes at the 'x' locations and the atomic structure at the interface between 110 and 115 is epitaxially matched, the interface 110/120 will generate much more second harmonic light than the interface 110/115.

In an alternative embodiment, a planar waveguide structure 110 is used for the solid substrate (FIG. 3). In this embodiment, a thin layer of high index of refraction material 115 (the waveguide), such as $TiO_2$ or $Ta_2O_5$, is deposited on top of the substrate 110 (typically glass). A thin diffraction grating 115 is scribed into this waveguide and light from the laser 100 is coupled using this grating into the waveguide. Second harmonic light can be collected using lenses and filters and detected with either a PMT-type device or a CCD camera.

Figure 4A:
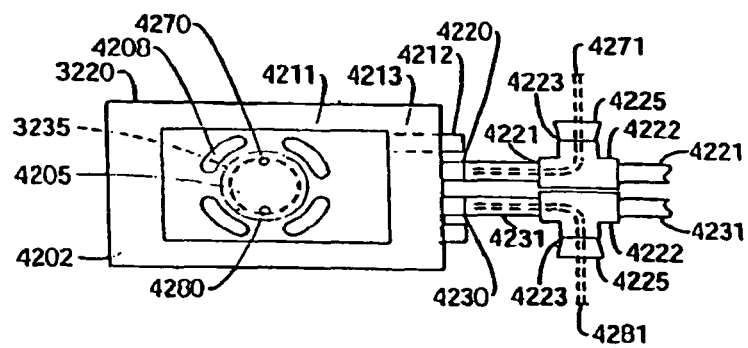
FIGS. 4A-D depict one embodiment of a flow-cell for delivery and removal of biological components and other fluids to the substrate containing attached probes.
Figure 4B:
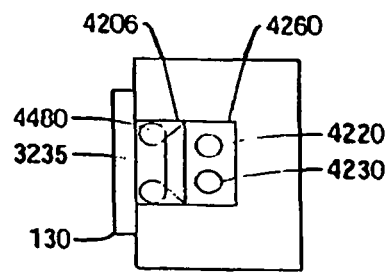
Figure 4C:
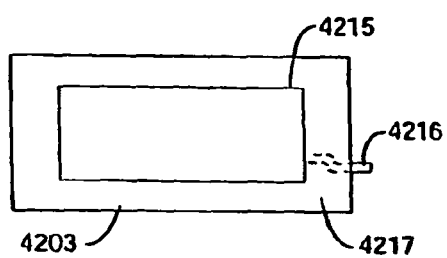

FIGS. 4A-C illustrate an embodiment of a flow cell for carrying out probe-target reactions. The flow cell is 3220 is shown in detail. FIG. 4A is a front view, FIG. 4B is a cross sectional view, and FIG. 4C is a back view of the cavity. Referring to FIG. 4A, flow cell 3220 includes a cavity 3235 on a surface 4202 thereon. The depth of the cavity, for example, may be between about 10 and 1500 μm, but other depths may be used. Typically, the surface area of the cavity is greater than the size of the probe sample, which may be about 13×13 mm. Inlet port 4220 and outlet port 4230 communicate with the cavity. In some embodiments, the ports may have a diameter of about 300 to 400 μm and are coupled to a refrigerated circulating bath via tubes 4221 and 4231, respectively, for controlling temperature in the cavity. The refrigerated bath circulates water at a specified temperature into and through the cavity.

A plurality of slots 4208 may be formed around the cavity to thermally isolate it from the rest of the flow cell body. Because the thermal mass of the flow cell is reduced, the temperature within the cavity is more efficiently and accurately controlled.

In some embodiments, a panel 4205 having a substantially flat surface divides the cavity into two subcavities. Panel 4205, for example, may be a light absorptive glass such as an RG1000 nm long pass filter. The high absorbance of the RG1000 glass across the visible spectrum (surface emissivity of RG1000 is not detectable at any wavelengths below 700 nm) substantially suppresses any background luminescence that may be excited by the incident wavelength. The polished flat surface of the light-absorbing glass also reduces scattering of incident light, lessening the burden of filtering stray light at the incident wavelength. The glass also provides a durable medium for subdividing the cavity since it is relatively immune to corrosion in the high salt environment common in DNA hybridization experiments or other chemical reactions.

Panel 4205 may be mounted to the flow cell by a plurality of screws, clips, RTV silicone cement, or other adhesives. Referring to FIG. 4B, subcavity 4260, which contains inlet port 4220 and outlet port 4230, is sealed by panel 4205. Accordingly, water from the refrigerated bath is isolated from cavity 3235. This design provides separate cavities for conducting chemical reaction and controlling temperature. Since the cavity for controlling temperature is directly below the reaction cavity, the temperature parameter of the reaction is controlled more effectively.

Substrate 130 is mated to surface 4202 and seals cavity 3235. Preferably, the probe array on the substrate is contained in cavity 3235 when the substrate is mated to the flow cell. In some embodiments, an O-ring 4480 or other sealing material may be provided to improve mating between the substrate and flow cell. Optionally, edge 4206 of panel 4205 is beveled to allow for the use of a larger seal cross section to improve mating without increasing the volume of the cavity. In some instances, it is desirable to maintain the cavity volume as small as possible so as to control reaction parameters, such as temperature or concentration of chemicals more accurately. In additional, waste may be reduced since smaller volume requires smaller amount of material to perform the experiment.

Referring back to FIG. 4A, a groove 4211 is optionally formed on surface 4202. The groove, for example, may be about 2 mm deep and 2 mm wide. In one embodiment, groove 4211 is covered by the substrate when it is mounted on surface 4202. The groove communicates with channel 4213 and vacuum fitting 4212 which is connected to a vacuum pump. The vacuum pump creates a vacuum in the groove that causes the substrate to adhere to surface 4202. Optionally, one or more gaskets may be provided to improve the sealing between the flow cell and substrate.

Figure 4D:
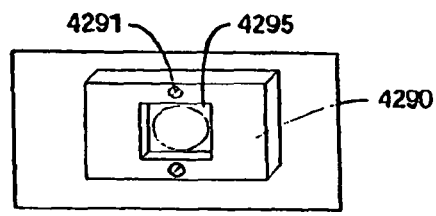

FIG. 4D illustrates an alternative technique for mating the substrate to the flow cell. When mounted to the flow cell, a panel 4290 exerts a force that is sufficient to immobilize substrate 130 located there between. Panel 4290, for example, may be mounted by a plurality of screws 4291, clips, clamps, pins, or other mounting devices. In some embodiments, panel 4290 includes an opening 4295 for exposing the sample to the incident light. Opening 4295 may optionally be covered with a glass or other substantially transparent or translucent materials. Alternatively, panel 4290 may be composed of a substantially transparent or translucent material.

In reference to FIG. 4A, panel 4205 includes ports 4270 and 4280 that communicate with subcavity 3235. A tube 4271 is connected to port 4270 and a tube 4281 is connected to port 4280. Tubes 4271 and 4281 are inserted through tubes 4221 and 4231, respectively, by connectors 4222. Connectors 4222, for example, may be T-connectors, each having a seal 4225 located at opening 4223. Seal 4225 prevents the water from the refrigerated bath from leaking out through the connector. It will be understood that other configurations, such as providing additional ports similar to ports 4220 and 4230, may be employed.

Tubes 4271 and 4281 allow selected fluids to be introduced into or circulated through the cavity. In some embodiments, tubes 4271 and 4281 may be connected to a pump for circulating fluids through the cavity. In one embodiment, tubes 4271 and 4281 are connected to an agitation system that agitates and circulates fluids through the cavity.

Referring to FIG. 4C, a groove 4215 is optionally formed on the surface 4203 of the flow cell. The dimensions of groove, for example, may be about 2 mm deep and 2 mm wide. According to one embodiment, surface 4203 is mated to the translation stage. Groove 4211 is covered by the translation stage when the flow cell is mated thereto. Groove 4215 communicates with channel 4217 and vacuum fitting 4216 which is connected to a vacuum pump. The pump creates a vacuum in groove 4215 and causes the surface 4203 to adhere to the translation stage. Optionally, additional grooves may be formed to increase the mating force. Alternatively, the flow cell may be mounted on the translation stage by screws, clips, pins, various types of adhesives, or other fastening techniques.

Figure 5A:
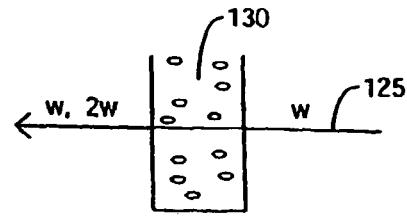
FIGS. 5A-C depict three embodiments of an apparatus in which the mode of generation and collection of the second harmonic light is by transmission through a sample.
Figure 5B:
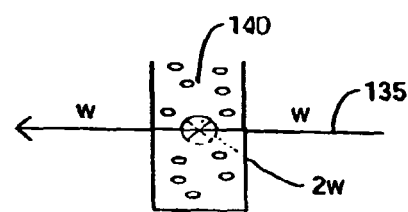
Figure 5C:
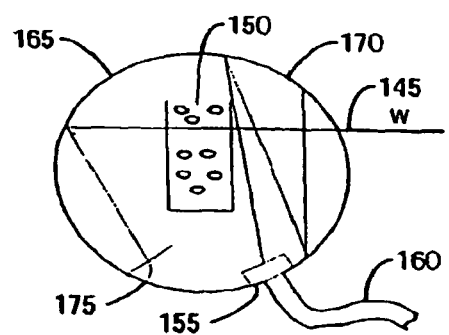

In a further alternative embodiment, a suspension of beads, cells, liposomes or other objects comprise the probes (130) as shown in FIGS. 5A-C. The scattered nonlinear light from such a sample—e.g., an isotropic sample in which each individual beads or other objects are about a coherence length or farther apart—is generated in various directions with some distribution in intensity. Fundamental light is transmitted through the suspension (130) and the nonlinear radiation collected. A number of modes of collecting the scattered nonlinear light is available. For example, collection of the second harmonic can be in the forward direction (A), at a right angle to the fundamental light (B), or using an integrating sphere approach (C). Part C shows an integrating sphere 165 with the sample 150 placed inside. Fundamental light (145) enters the entrance port (170), passes through the sample (150), undergoes a reflection at the sphere wall, and is stopped by baffle (175). The scattered second harmonic light is collected from the sphere surface through exit port (155) and coupled out of the sphere by a fiber optic line (160). Cells are a convenient and natural system of study for conformational changes in receptors, cell surface molecules and other biological components. Beads can support phospholipid bilayers (e.g., with membrane proteins) or probes such as proteins or nucleic acids can be attached to their surface. The beads provide a large amount of distributed surface area in the sample and can be a useful alternative to planar surface geometries, especially when the fundamental and nonlinear light is used in the transmission mode.

In an alternative embodiment (FIG. 6), the excitation light is transformed from a point-like shape into some other shape using various optics. For instance, the point-like beam shape of the fundamental beam can be transformed into a line shape, useful for scanning the sample surface. However, because the intensity of the nonlinear beam depends on, among other factors, the intensity of the fundamental (typically a quadratic dependence on the fundamental intensity), this transformation will result in less nonlinear light intensity generated at a given location. To generate a line-shape in the fundamental (which can typically be a round point of ~2 mm diameter), one can direct the fundamental beam into a microscope objective which has a magnification power of about 10 followed by a 150 mm achromat to collimate the beam as well known in the prior art and as disclosed in detail in U.S. Pat. No. 5,834,758. As shown in FIG. 6, the fundamental light 180 is a beam of typically 2-3 mm diameter. This beam is directed through a microscope objective 185. The objective, which has a magnification power of 10, expands the beam to about 30 mm. The beam then passes through a lens 190. The lens, which can be a 150 mm achromat, collimates the beam. Typically, the radial intensity of the expanded collimated beam has a Gaussian profile. To minimize intensity variations in the beam, a mask 195 can be inserted after lens 190 to mask the top and bottom of the beam, thereby passing only the central portion of the beam. In one embodiment, the mask passes a horizontal band that is about 7.5 mm. Thereafter, the beam passes through a cylindrical lens 200 having a horizontal cylinder axis, which can be a 100 mm f.l. made by Melles Griot. The cylindrical lens expands the beam spot vertically. Alternatively, a hyperbolic lens can be used to expand the beam vertically while resulting in a flattened radial intensity distribution. From the cylindrical lens, the light passes through a lens 205. Optionally, a planar mirror can be inserted after the cylindrical lens to reflect the excitation light toward lens 205. To achieve a beam height of about 15 mm, the ratio of the focal lengths of the cylindrical lens 200 and lens 205 is approximately 1:2, thus magnifying the beam to about 15 mm. Lens 205, which in some embodiments is a 80 mm achromat, focuses the light to a line of about 15 mm.times.50 microns at the sample surface 210.

In an alternative embodiment shown in FIGS. 7A-B, probes are patterned in a two-dimensional array (A, top view of array on surface) where each region on the surface—{1, 35} in this example—can be a different oligonucleotide or protein sequence (or a combination of the same and different sequences). Part B shows a side-view of the sample surface (220) in a well (215) containing the targets (225) shown here as protein objects with second-harmonic-active labels (X) attached. The well can hold liquid or buffer and serves to physically separate the contents of the well from other parts of the substrate or other elements in a substrate array. The fundamental light can be multiplexed and each resultant beam can be guided by individual mirrors to simultaneously scan different lines or regions within the array, thus increasing even further the potential of the technique for high-throughput studies.

Figure 8:
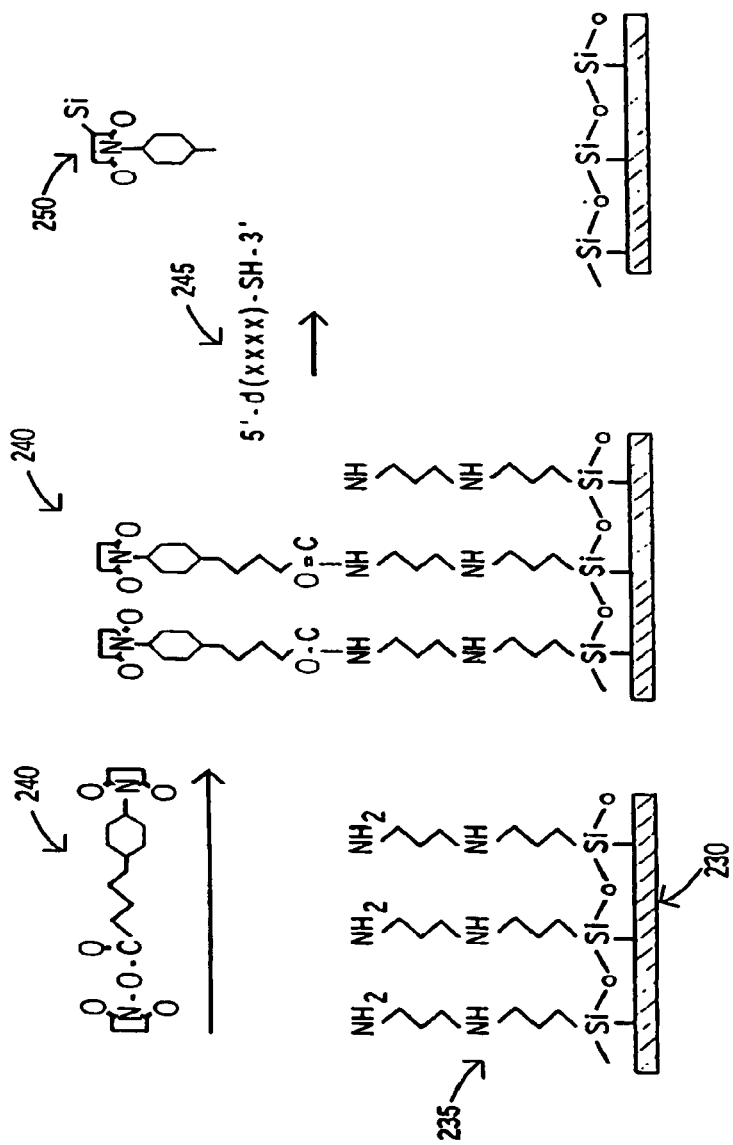
FIG. 8 depicts one embodiment of a surface chemistry used to attach oligonucleotide or polynucleotide samples to the substrate surface.

In an alternative embodiment, the method of Levicky et al. "Using Self-Assembly to Control the Structure of DNA Monolayers on Gold: A Neutron Reflectivity Study," Journal of the American Chemical Society 120: 9787-9792 (1998), or the method of Chrisey et al., "Covalent Attachment of Synthetic DNA to Self-Assembled Monolayer Films", Nucleic Acids Research 24, 3031, (1996), is used to attach the probe DNA to the substrate. In the method of Chrisey et al., as illustrated in FIG. 8, a fused silica or oxidized silicon substrate is used (230) and derivatized with N-(2-aminoethyl)-3-aminopropyltrimethoxysilane (EDA) (235). In one embodiment, the EDA-modified surface is then treated with the heterobifunctional crosslinker (SMPB), whose succinimide ester moiety reacts with the primary amino group of EDA (240). A thiol DNA oligomer subsequently (245) of base-pair sequence (xzzy) (where 'xzzy' represents the entire sequence) reacts with the maleimide portion of the SMPB crosslinker, to yield the covalently bound species shown (250).

Figure 9A:
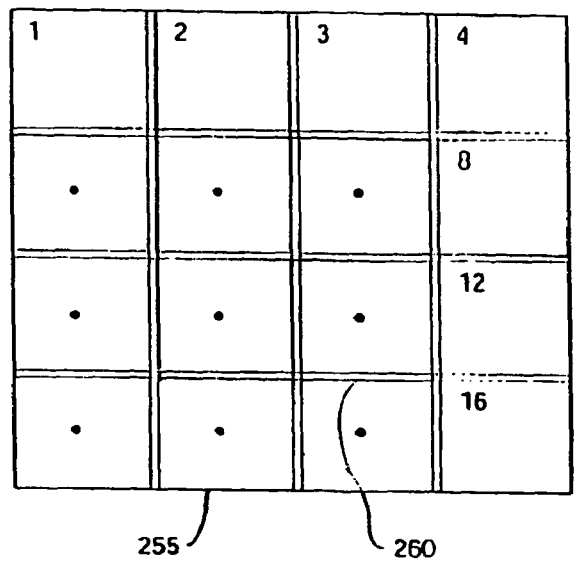
FIGS. 9A-B depict an embodiment of a substrate containing multiple wells.
Figure 9B:
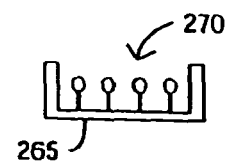

In an alternative embodiment, elements in the surface array are physically separated as illustrated in FIG. 9, allowing for different targets, target solutions, etc. to be added selectively to any or all of the elements. Part (A) is a top-view of the substrate (255) with partitions or walls (260) separating the different well regions—in this example, 16 wells. Part (B) shows a side-view of a well (265) with attached probes (270). Such arrays are commonly found in the art, such as the 96-well plates, etc. and are commercially available (Fisher Scientific, Inc. etc.)

Figure 10:
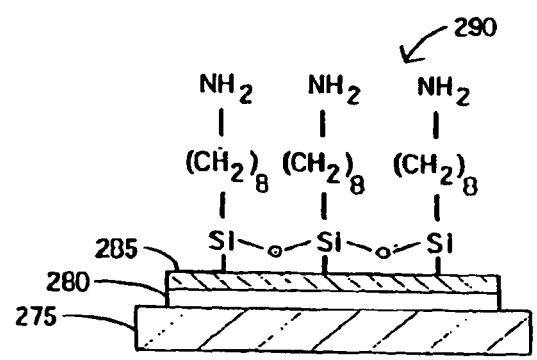
FIG. 10 depicts an embodiment of the apparatus substrate with the use of an aminosilane surface-attached layer on top of a reflective coating. The reflective coating underneath the aminosilane layer improves collection of the nonlinear optical light. The aminosilane layer is suitable for coupling biomolecules or other probe components to the substrate.

In an alternative embodiment, a glass substrate surface can be coated with a layer of a reflective metal such as silver. The metallic layer will increase nonlinear optical generation and collection. Biomolecules or other particles can be attached to derivatized layers built on top of the metal. For instance, the metal can be coated with a layer of silicon dioxide ($SiO_2$), then with a layer of aminosilane such as 3-amino-octyl-trimethoxysilane. Oligonucleotides or polynucleotides can then be attached to the aminosilane layer using linkers which connect the 3' or 5' end of the oligo to the amine group. Alternatively, the oligos or polynucleotides can be adsorbed to the aminosilane layer. FIG. 10 illustrates an embodiment of this type where a glass substrate (275) is derivatized with a Ag layer (280). A thin coat of $SiO_2$ is then deposited on top of the silver layer (285) and derivatized with the aminosilane (290).

In a specific embodiment, nucleic acid or PNA microarrays can be obtained commercially or constructed according to public literature (e.g., http://cmgm.stanford.edu/pbrown/mguide/index.html). The surface chemistry to be used is that found in Chrisey et al., "Covalent Attachment of Synthetic DNA to Self-Assembled Monolayer Films", Nucleic Acids Research 24, 3031, (1996), in which oligonucleotides are attached to self-assembled monolayer silane films on fused silica slides. Silanization is accomplished via N-(2-aminoethyl)-3-aminopropyltrimethoxysilane.

In other embodiments, oligonucleotides or PNAs can be attached to the solid substrate via light-directed synthesis (S. A. Fodor, Science 277 (1997), 393) or via chemical synthesis (e.g., Chrisey et al., "Covalent Attachment of Synthetic DNA to Self-Assembled Monolayer Films", Nucleic Acids Research 24, 3031, (1996)).

In still other embodiments, surfaces or microarrays microarrays of oligonucleotides or PNAs can be obtained commercially or constructed according to public literature (e.g., http://cmgm.stanford.edu/pbrown/mguide/index.html).

DNA microarrays can be obtained commercially or constructed, for example, according to public literature (e.g., http://cmgm.stanford.edu/pbrown/mguide/index.html). The surface chemistry preferably to be used is that found in Chrisey et al., "Covalent Attachment of Synthetic DNA to Self-Assembled Monolayer Films", Nucleic Acids Research 24, 3031, (1996), in which oligonucleotides are attached to self-assembled monolayer silane films on fused silica slides.

Silanization is done via N-(2-aminoethyl)-3-aminopropyltrimethoxysilane and Hoheisel, J. D. "Improved solid supports and spacer/linker systems for the synthesis of spatially addressable PNA-libraries" Nucleosides Nucleotides 18 (1999) 1289-1291 on glass or silica. The buffer or solution in contact with the PNA oligonucleotides can be chosen from a range of those known in the art. Hybridization and wash solutions are found in the art. For example, the web site: cmgm.stanford.edu/pbrown/protocols gives detailed instructions for probe-target hybridization.

Microarrays can be mounted on an x-y translation stage and driven by personal computer (PC control) using a motorized translator (acquired from Oriel, Inc.) or using one of the many procedures in the art (e.g., V. G. Cheung et al., "Making and reading microarrays", Nature Genetics (Suppl.), 1999, 21: 15-19).

Figure 11A:
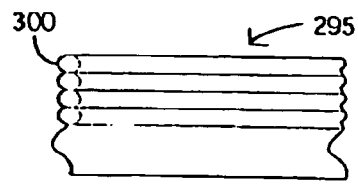
FIG. 11A depicts the use of a bundle of fiber optic lines and FIG. 11B depicts the use of beads coupled to the end of a fiber for attaching probes.
Figure 11B:
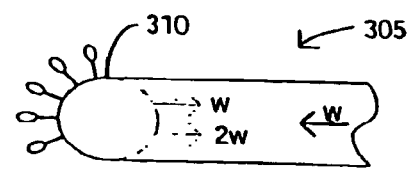

In an alternative embodiment, bead-based fiber-optic arrays can be used (ref 34) in which light beams (e.g., fundamental and second harmonic) travel via total internal reflection along the path of the fiber. The fundamental light is coupled into the bundle or individual optical fibers and second harmonic light is generated at the tip surface and collected back through the fiber. FIGS. 11A-B illustrate a fiber-optic bundle array. Part (A) shows a bundle of fiber optic cables (295) with wells at the distals ends for placement of beads (300). Part (B) shows a close-up view of a single optical fiber. Fundamental light travels (.omega.) toward the distal end with the bead (305). Some fundamental light is scattered back from the bead along with second harmonic light (2.omega.) and travels back through the fiber to the proximal end where an optical train and detection system (not shown) separates the fundamental radiation from the second harmonic radiation. Bead (310) is covered with probes.

In an alternative embodiment, green fluorescent protein (GFP) or nonlinear-active mutants thereof are used to label proteins in-vivo via mutagenesis according to procedures well known in the art. The GFP or mutants thereof are second-harmonic active and can serve as a built-in label of proteins. For example: a cell membrane receptor can be labeled with GFP via mutagenesis. Cells containing this GFP-tagged receptor produce some background second harmonic light when illuminated with a fundamental beam in a surface-selective nonlinear optical technique. When ligands or other compounds which bind to the receptor and induce activation—and a concomitant conformational change—the intensity and/or spectrum and/or time-course of the second harmonic light will change (due, for example, to a change in overall net orientation of the GFP protein) as the GFP label moves slightly due to the conformational change on the receptor. The change in measured nonlinear optical properties are thus correlated with conformational change and ligand binding.

In an alternative embodiment, the detector (65) of the nonlinear radiation in FIG. 1 is a photomultiplier tube operated in single-photon counting mode. Photocurrent pulses can be voltage converted, amplified, subjected to discrimination using a Model SR445Fast Preamplifier and Model SR 400 Discriminator (supplied by Stanford Research Systems, Inc.) and then sent to a counter (Model 3615 Hex Scaler supplied by Kinetic Systems). Photon counter gating and galvo control through a DAC output (Model 3112, 12-Bit DAC supplied by Kinetic Systems) can be synchronized using a digital delay/pulse generator (Model DG535 supplied by Stanford Research Systems, Inc.). Communication with a PC computer 29 can be accomplished using a parallel register (Model PR-604 supplied by DSP Technologies, Inc.), a CAMAC controller card (Model 6002, supplied by DSP Technologies, Inc.) and a PC adapter card (Model PC-004 supplied by DSP Technologies, Inc.).

In an alternative embodiment, a bandpass, notch, or color filter is placed in either or all of the beam paths (e.g., fundamental, second harmonic, etc.) allowing, for example, for a wider spectral bandwidth or more light throughput.

In an alternative embodiment, an interference, notch-pass, bandpass, reflecting, or absorbant filter can be used in place of the filters in the figures in order to either pass or block the fundamental or nonlinear optical beams.

According to another embodiment, detection of the nonlinear optical light is achieved using a charge coupled detector (CCD) in place of a photomultiplier tube or other photodetector. The CCD subsystem communicates with and is controlled by a data acquisition board installed in a computer. Data acquisition board may be of the type that is well known in the art such as a CIO-DAS 16/Jr manufactured by Computer Boards Inc. The data acquisition board and CCD subsystem, for example, may operate in the following manner. The data acquisition board controls the CCD integration period by sending a clock signal to the CCD subsystem. In one embodiment, the CCD subsystem sets the CCD integration period at 4096 clock periods. by changing the clock rate, the actual time in which the CCD integrates data can be manipulated. During an integration period, each photodiode accumulates a charge proportional to the amount of light that reaches it. Upon termination of the integration period, the charges are transferred to the CCD's shift registers and a new integration period commences. The shift registers store the charges as voltages which represent the light pattern incident on the CCD array. The voltages are then transmitted at the clock rate to the data acquisition board, where they are digitized and stored in the computer's memory. In this manner, a strip of the sample is imaged during each integration period. Thereafter, a subsequent row is integrated until the sample is completely scanned.

In a specific embodiment, the nonlinear spectrum of a sample is measured by measuring the nonlinear radiation (e.g., second harmonic radiation) at two or more spectral points or bands, using a monochromator, filter or other wavelength-selecting device to accomplish this.

In a specific embodiment, a monochromator (60) can be placed before the detecting element in the device, in order to spectrally resolve the nonlinear optical radiation (FIG. 1).

In a specific embodiment, imaging techniques described in the art (Peleg et al., "Nonlinear optical measurement of membrane potential around single molecules at selected cellular sites," Proc. Natl. Acad. Sci. V. 96, 1999, 6700-6704, or Campagnola et al., "High-resolution nonlinear optical imaging of live cells by second harmonic generation," Biophysical Journal 77 (6), 3341-3349 (1999), can be performed using SHG-labeled components (such as labeled ligands or receptors) instead of the membrane intercalating dyes used in the art. These imaging techniques can be used to image solid surfaces, cell surfaces or other interface using SHG-labeled components.

In a specific embodiment, channels (or microfluid) channels can be used to introduce the components into the sample cell via positive displacement, pumping, electrophoretic means or other means known in the art for manipulating the flow of components into and out of a reaction chamber.

In a specific embodiment, the apparatus can be assembled into a user-closed product with a user-controlled interface (an LED panel, for example, or PC-based software) with the option of inserting and removing disposable substrates (e.g., biochips) with the attached probes.

In a specific embodiment, a photodiode, avalanche photodiode or other photoelectric detector (65) in FIG. 1 is used as the light detection means.

In a specific embodiment, a surface array can be used that is in a fixed position and the incident light beam scanned across the surface using methods well known in the art, such as a galvanometer mirror or a polygonal mirror.

An alternative embodiment comprises a scanning or imaging method where a physical property of the nonlinear radiation is measured as function of position (x,y,z) in a sample. The scanning method can comprise a combination of both stage translation (x-y) and beam scanning, wherein, for example, the latter controls the incident position of the fundamental beam on the array surface.

In a specific embodiment, a stop-flow mixing chamber is used to rapidly mix the components in the sample cell.

In a specific embodiment, the proportionality constant (calibration curve of intensity of second harmonic light vs. concentration of targets bound to attached probes) is determined by measuring the concentration of targets using another method such as radiolabeling or fluorescence labels of the targets. Once the calibration curve is known, for a given probe and target type (e.g., cDNA, RNA, size of oligos, etc.), the concentration of bound target is determined using this relation and the measured second harmonic intensity. This embodiment can be generalized to any other nonlinear light beam emanating from the sample, including third harmonic, sum or difference frequency light.

In a specific embodiment, the nonlinear optical, surface-selective apparatus can comprise a unit without the light excitation source (e.g., with sample compartment, filters, detectors, monochromator, computer interface, software, or other parts) so that the user can supply his own excitation source and adapt its use to the methods described herein.

In an alternative embodiment, measurable information can be recorded in real time.

Various Configurations of an Apparatus Using the Surface-Selective Nonlinear Optical Technique in the Present Invention The apparatus for detection of the probe-target reactions or their effects can assume a variety of configurations. In its most simple form, the apparatus will comprise the following:
  i) a source of the fundamental light
  ii) a detector for measuring the intensity of the second harmonic or other nonlinear optical beams.

More elaborate versions of the apparatus will employ, for example: a monochromator (for wavelength selection), a pass-filter, color filter, interference or other spectral filter (for wavelength selection or to separate the fundamental(s) from the higher harmonics), one or more polarizing optics, a means of applying an electric field, one or more mirrors or lenses for directing and focusing the beams, computer control, software, etc.

The mode of delivering or generating the nonlinear optical light (e.g., SHG) can be based on one or more of the following means: TIR (Total internal reflection), Fiber optics (with or without attached beads), Transmission (fundamental passes through the sample), Reflection (fundamental is reflected from the sample), scanning imaging (allows one to scan a sample), confocal imaging or scanning, resonance cavity for power build-up, multiple-pass set-up.

Measured information can take the form of a vector which can include one or more of the following parameters: {intensity of light (typically converted to a photovoltage by a PMT or photodiode), wavelength of light (determined with a monochromator and/or filters), time, substrate position (for array samples, for instance, where different sub-samples are encoded as function of substrate location and the fundamental is directed to various (x,y) locations}. Two general configurations of the apparatus are: image scanning (imaging of a substrate—intensity, wavelength, etc. as a function of x,y coordinate) and spectroscopic (measurement of the intensity, wavelength, etc. for some planar surface or for a suspension of cells, liposomes or other particles).

The fundamental beam can be delivered to the sample in a variety of ways. FIGS. 12-16 are schematics of various modes of delivering the fundamental and generating second harmonic beams. It is understood that in sum- or difference-frequency configurations, the fundamental beams will be comprised of two or more beams, and will generate, at the interfaces, the difference or sum frequency beams. For the purposes of illustration, only the second harmonic generation case is described in detail herein. Furthermore, it shall be understood that the sample cell 3 in all cases can be mounted on a translation stage (1-, 2-, or 3-dimensional degrees of freedom) for selecting precise locations of the interfacial interaction volume. The sample cell in all cases can be fitted with flow ports and tubes which can serve to introduce (or flush out) components such as molecules, particles, cells, etc.

Transmission

Figure 12A:
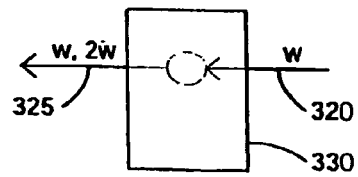
FIGS. 12A-C depict three embodiments of an apparatus in which the mode of generation and collection of the second harmonic light is by transmission through a sample.

FIG. 12A is a schematic of a configuration relying on transmission of the fundamental and second harmonic beams. The fundamental 320 ($\omega$) passes through the sample cell 330 and interacts within a volume element (denoted by the circle) in which are contained one or more interfaces capable of generating the second harmonic beam 325 ($2\omega$). The fundamental and second harmonic beams are substantially co-linear as denoted by beam 325. The sample cell can contain suspended beads, particles, liposomes, biological cells, etc. in some medium, providing interfacial area capable of generating second harmonics in response to the fundamental beam. As shown, the second harmonic is detected co-linearly with the fundamental direction, but could alternatively be detected off-angle from the fundamental, for instance at 90° to the fundamental beam.

Figure 12B:
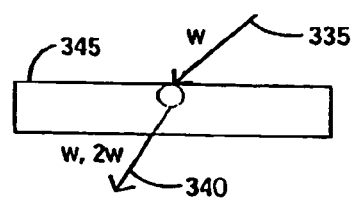

FIG. 12B is a schematic of another configuration relying on transmission of the fundamental and second harmonic beams. The fundamental 335 is directed onto a sample cell 345 and the second harmonic waves are generated at the top surface—this surface can be derivatized with immobilized probes or with adsorbed particles, liposomes, cells, etc. The second harmonic waves 340 are generated within a volume element denoted by the circle at the interface between the top surface and the medium contained within cell.

Figure 12C:
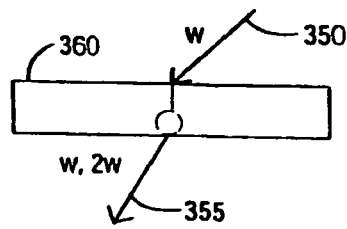

FIG. 12C is a schematic of a configuration substantially similar to the one depicted in FIG. 2A except that the bottom surface of the sample cell 3, rather than the top, is used to generate the second harmonic waves.

Total Internal Reflection

FIG. 13A is a schematic of a waveguide 4 capable of acting as a total internal reflection waveguide which refracts the fundamental 365 and directs it to a location at the interface between the waveguide 380 and a sample cell 375. At this location, denoted by the circle, the fundamental will generate the second harmonic waves and undergo total internal reflection; the second harmonic beam will propagate substantially colinearly with the fundamental and exit the prism 380. Waveguide 380 will typically be in contact with air. In this illustration, the waveguide 380 is a Dove prism.

FIG. 13B is a schematic of a configuration similar to the one depicted in FIG. 13A except that the waveguide 400 allows for multiple points of total internal reflection between the waveguide 4 and the sample cell 395, increasing the amount of second harmonic light generated from the fundamental beam.

Fiber Optic

FIG. 14 depicts various configurations of a fiber optic means of delivering or collecting the fundamental or second harmonic beams. In FIG. 14A, the coupling element 410 between a source of the fundamental wave and the fiber optic is depicted. The fundamental, thus coupled into the fiber optic waveguide 405, proceeds to a sample cell 415. In FIG. 14A, the tip of the fiber can serve as the interface of interest capable of generating second harmonic waves, or the tip can serve merely to introduce the fundamental beam to the sample cell containing suspended cells, particles, etc. In FIG. 14A, the second harmonic light is collected back through the fiber optic.

FIG. 14B is identical to FIG. 14A except that a bead is attached to the tip of the fiber optic (according to means well known in the art). The bead can serve to both improve collection efficiency of the second harmonic light or be derivatized with probes or adsorbed species and presenting an interface with the medium of sample cell 425 capable of generating the second harmonic light.

FIG. 14C is identical to both FIGS. 14A and 14B except that collection of the second harmonic light is effected using a solid-angle detector 450.

Optical Resonance Cavity

An optical resonance cavity is defined between at least two reflective elements and has an intracavity light beam along an intracavity beam path. The optical cavity or resonator consists of two or more mirrored surfaces arranged so that the incident light can be trapped bouncing back and forth between the mirrors. In this way, the light inside the cavity can be many orders of magnitude more intense than the incident light. This phenomenon is well known and has been exploited in various ways (see, for example, Yariv A. "Introduction to Optical Electronics", $2^{nd}$ Ed., Holt, Reinhart and Winston, N.Y. 1976, Chapter 8). The sample cell can be present in the optical cavity or it can be outside the optical resonance cavity.

Figure 15A:
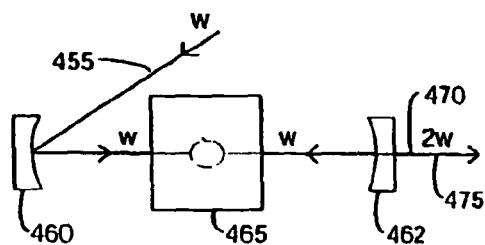
FIGS. 15A-B depict two embodiments of an apparatus using an optical cavity for power build-up of the fundamental.

FIG. 15 is a schematic of an optical resonance power build-up cavity configuration. FIG. 15A is a schematic of an optical resonance cavity in which the sample cell 465 is positioned intracavity and the fundamental and second harmonic beams are transmitted through it—a useful configuration for sample cells containing suspended particles, cells, beads, etc. The fundamental beam 455 enters the optical resonance cavity at reflective optic 460 and builds up in power between reflective elements 460 and 462 (intracavity beam). Mirror 460 is preferably tilted (not perpendicular to the direction of the incident fundamental 455) to prevent direct reflection of the intracavity beam back into the light source. The natural reflectivity and transmissivity of 460 and 462 can be adjusted so that the fundamental builds up to a convenient level of power within the cavity. The fundamental generates second harmonic light in a volume element within the sample cell denoted by the circle. Reflective optic 460 can reflect the fundamental and the second harmonic, while reflective optic 462 will substantially reflect the fundamental but allow the pass-through of the second harmonic beam 475 which is subsequently detected. U.S. Pat. No. 5,432,610 (King et al.) describes a diode-pumped power build-up cavity for chemical sensing and it and the references it makes are hereby incorporated by reference herein.

Figure 15B:
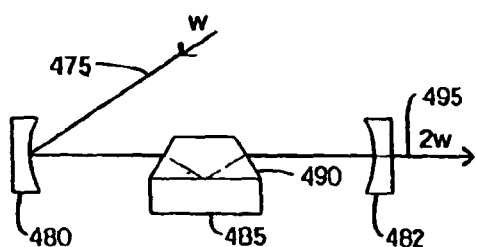

FIG. 15B is a schematic of an optical resonance power build-up cavity configuration in which the fundamental beam 475 enters the optical cavity by reflection from optic 480. A second reflective optic element 482 defines the optical resonance cavity. Element 490 is a waveguide (such as a prism) in contact with the sample cell 485 and allows total internal reflection of the fundamental beam at the interface between the waveguide and sample cell surfaces, generating the second harmonic light. Element 482 substantially reflects the fundamental beam but passes through the second harmonic beam 495 which is subsequently detected.

Reflection

Figure 16A:
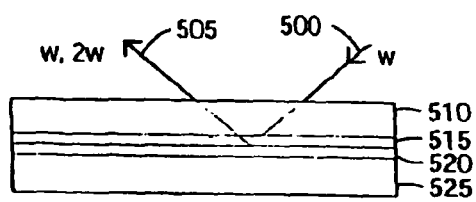
FIGS. 16A-C depict three embodiments of an apparatus in which the mode of generation and collection of the second harmonic light uses reflection of the light from an interface.

FIG. 16A is a schematic of a configuration involving reflection of the fundamental and second harmonic beams. A substrate 525 is coated with a thin layer of a reflective material 520, such as a metal, and on top of this is deposited at layer 515 suitable for attachment of the probes or adsorption of particles, cells, etc. (e.g., $SiO_2$). This layer is in contact with the sample cell 510. The fundamental 500 passes through the sample cell 510 and generates a second harmonic wave at the interface between layers 515 and 520. The fundamental and second harmonic waves 505 are reflected back from the surface of layer 520.

Figure 16B:
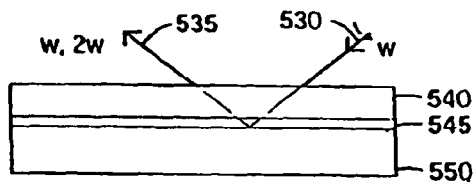

FIG. 16B is substantially similar to FIG. 15A except that the second harmonic and fundamental beams are reflected 535 from the interface between the medium contained in sample cell 540 and layer 545. Layer 545 is reflective or partly reflective layer deposited on substrate 550 and is suitable for adsorption of particles, cells, etc. or attachment of probes.

Figure 16C:
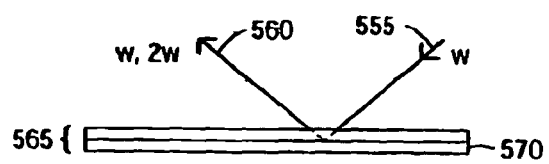

FIG. 16C is a schematic illustrating that only the sample cell 565 need be used for a reflective geometry. The sample cell 565 is partly filled with some medium 570 and the fundamental and second harmonic beams are reflected 560 from the gas-liquid or vapor-liquid interface at the surface of 570.

Modes of Detection

Charge-coupled detectors (CCD) array detectors can be particularly useful when information is desired as a function of substrate location (x,y). CCDs comprise an array of pixels (i.e., photodiodes), each pixel of which can independently measuring light impinging on it. For a given apparatus geometry, nonlinear light arising from a particular substrate location (x,y) can be determined by measuring the intensity of nonlinear light impinging on a CCD array location (Q,R) some distance from the substrate—this can be determined because of the coherent, collimated (and generally co-propagating with the fundamental) nonlinear optical beam) compared with the spontaneous, stochastic and multidirectional nature of fluorescence emission. With a CCD array, one or more array elements {Q,R} in the detector will map to specific regions of a substrate surface, allowing for easy determination of information as a function of substrate location (x,y). Photodiode detector and photomultiplier tubes (PMTs), avalanche photodiodes, phototransistors, vacuum photodiodes or other detectors known in the art for converting incident light to an electrical signal (i.e., current, voltage, etc.) can also be used to detect light intensities. For CCD detector, the CCD communicates with and is controlled by a data acquisition board installed in the apparatus computer. The data acquisition board can be of the type that is well known in the art such as a CIO-DAS 16/Jr manufactured by Computer Boards Inc. The data acquisition board and CCD subsystem, for example, can operate in the following manner. The data acquisition board controls the CCD integration period by sending a clock signal to the CCD subsystem. In one embodiment, the CCD subsystem sets the CCD integration period at 4096 clock periods. By changing the clock rate, the actual time in which the CCD integrates data can be manipulated. During an integration period, each photodiode accumulates a charge proportional to the amount of light that reaches it. Upon termination of the integration period, the charge is transferred to the CCD's shift registers and a new integration period commences. The shift registers store the charges as voltages which represent the light pattern incident on the CCD array. The voltages are then transmitted at the clock rate to the data acquisition board, where they are digitized and stored in the computer's memory. In this manner, a strip of the sample is imaged during each integration period. Thereafter, a subsequent row is integrated until the sample is completely scanned.

Sample Substrates and Sample Cells

Sample substrates and cells can take a variety of forms drawing from, but not limited to, one or more of the following characteristics: fully sealed, sealed or unsealed and connected to flow cells and pumps, integrated substrates with a total internal reflection prism allowing for evanescent generation of the nonlinear beam, integrated substrates with a resonant cavity for fundamental power build-up, an optical set-up allowing for multiple passes of the fundamental for increased nonlinear response, sample cells containing suspended biological cells, particles, beads, etc.

Data Analysis

Data analysis operates on the vectors of information measured by the detector. The information can be time-dependent and kinetic. It can be dependent on the concentration of one or more biological components, inhibitors, antagonists, agonists, drugs, small molecules, etc. which can be changed during a measurement or between measurements. It can also be dependent on wavelength, etc. In general, the intensity of nonlinear light will be transformed into a concentration or amount of a particular state (for example, the surface-associated concentration of a component or the amount of opened or closed ion-channels in cell membranes) via the detected change in nonlinear optical properties that are correlated to conformational changes induced in the sample.

Details of the data analysis can vary from experiment to experiment. There is a large literature available for making correlations between conformation and fluorescence intensity (see the references by Glauner et al., Nature 402, 813 (1999), Ghanouni et al., Proc. Natl. Acad. Sci., v. 98, 5997 (2001), and Ghanouni et al., Journal of Biological Chemistry, v. 276, 24433 (2001), and references therein). Analogous procedures are constructed for the nonlinear optical techniques. For instance, the square root of the intensity of second harmonic light (proportional to electric field amplitude of the light) is proportional to the number of nonlinear-active species in a sample times the orientational average of the hyperpolarizability of the species. This is a well known relationship that can be used to quantify conformational change (and in turn binding affinity to a probe) with intensity of a nonlinear beam. Kinetics and equilibrium properties of the reactions of interest can be determined via the measurements and appropriate data analysis.

Screening for Candidate Binding Partners

Candidate binding partners for binding a test molecule can be screened through the detection of conformational changes on probe-target binding. The method of screening one or more candidate binding partners for binding to a test molecule involves measuring the one or more physical properties of the one or nonlinear optical light beams emanating from said sample comprising the test molecule and the one or more candidate binding partners, where a change in the one or more physical properties of the nonlinear light beams relative to a value measured in the absence of exposure to the one or more candidate binding partners is an indication of a binding event having occurred. In a preferred embodiment the candidate binding partner is not attached to the surface.

The probes or targets of the present invention that can be used include but are not limited to naturally occurring, artificially altered, or genetically engineered, biological species or non-biological species. The candidates for probes or targets also include but are not limited to one or more of the following components: a nucleic acid, protein, small molecule, organic molecule, biological cell, virus, molecular beacon, liposome, receptor, antibody, agonist, antagonist, inhibitor, hapten, ligand, antigen, oocyte, hormone, protein, peptide, receptor, drug, lipid, ganglioside, enzyme, nucleotide, carbohydrate, cDNA, oligonucleotide, nucleoside, polynucleoside, polynucleotide, lipid, ganglioside, oligosaccharide, peptide nucleic acid (PNA), toxin, nucleic acid analog, ion channel receptor, G coupled-protein receptor. In a specific embodiment, the probes can be patterned in an array format on a substrate or solid surface, with the properties or chemical identity of the probes remaining constant or varying among regions of the array.

In one embodiment of the selection of candidate binding partners, an external electric field can be applied to the samples to create the non-centrosymmetric condition required for the nonlinear optical techniques. For example, proteins (e.g., solubilized GPCRs) that are labeled with a nonlinear-active label can be partially oriented in the electric field. A background nonlinear light signal is measured. When a ligand that binds to the protein is added to the medium, it triggers a conformational change in the protein (well known to those skilled in the art) that results in a change in the properties of the nonlinear light signal (e.g., a change in intensity). This scheme can be very useful in screening libraries of ligands (small molecules, drugs, etc.) for binding to proteins—i.e., high-throughput drug screening. In a preferred embodiment, the proteins are GPCRs, a well known as a class of proteins that are implicated in disease, and for which drugs can be developed. Drugs can be agonists, antagonists, inhibitors, etc. that interact (e.g., bind) with the receptors in some way. The following references (and references therein) describe different exemplary GPCRs that can be used:

P. Ghanouni et al., "Agonist-induced conformational changes in the G-protein-coupling domain of the $\beta_2$ adrenergic receptor", Proc. Natl. Acad. Sci., v. 98, 5997 (2001).

P. Ghanouni et al., "Functionally Different Agonists Induce Distinct Conformations in the G Protein Coupling Domain of the $\beta_2$ Adrenergic Receptor", Journal of Biological Chemistry, v. 276, 24433 (2001).

C. Bieri et al., "Micropatterned immobilization of a G protein-coupled receptor and direct detection of G protein activation", Nature Biotechnology, 17, 1105 (1999).

Helmreich, E. J. M. and Hofmann, K P, "Structure and Function of Proteins in G-protein-coupled signal transfer", Biochimica et Biophysica Acta 1286, 285 (1996).

Gether et al. (1995) J Biol Chem 270, 28628-28275, Fluorescent labeling of purified $\beta_2$ Adrenergic receptor.

Turcatti et al. (1996) J Biol Chem 271, 19991-19998, Probing the Structure and Function of the Tachykinin Neurokinin-Receptor through Biosynthetic incorporation of fluorescent amino acids at specific sites.

Liu et al. (1996) Biochemistry 35, 11865-11873, Site-Directed fluorescent labeling of P-glycoprotein on cysteine residues in the nucleotide binding domains.

Lodish, Harvey, et al., Molecular Cell Biology ($4^{th}$ ed., 2000).

Screening for Modulators

The invention provides a method of screening one or more candidate modulator molecules for the ability to modulate the interaction between a test molecule and its binding partner. The action of modulator and inhibitor molecules have been previously described. Any change in the one or more physical properties of the nonlinear light beam emanating from a sample comprising the test molecule, its binding partner and the modulator, relative to what was measured in the absence of exposure of the test molecule to the binding partners, serves as an indicator of the ability of the candidate modulator molecules to modulate the interaction between the test molecule and its binding partner (i.e. to increase or decrease their binding).

The invention can be used, for example, to monitor gene expression or for studies involving drug screening or high-throughput screening where a candidate drug is tested for binding, or its effect on probe-target binding, i.e., to reduce or enhance probe-target binding. In other cases, for example, a drug can be tested for efficacy by its ability to bind to a receptor or other molecule on the surface of a biological cell. In another specific embodiment, compounds that are potential inhibitors of an agonist to a receptor are screened by testing for blocking of the agonist binding to the receptor, i.e., removal of a conformational change induced by the agonist when the receptor and agonist are also in the presence of an inhibitor candidate.

In a specific embodiment, the invention is used for drug screening or high-throughput screening where a candidate drug is tested for its ability to activate or inhibit a probe (e.g., a receptor, ion channel protein, etc.). A drug candidate is tested for its ability to activate a conformational change in a probe—in this case, one seeks agonists of the probe.

In an alternative embodiment, target-probe interactions can be measured in the presence of some modulator of the interactions—the modulator being, for example, a small molecule, drug, or other moiety, molecule or particle which changes in some way the target-probe interactions (e.g., has some affinity for the probe and blocks or inhibits target binding). The effect of a modulator on probe-target binding, where the target is known to bind to the probes, is investigated using the nonlinear optical method. The modulator can be added before, during or after the time in which the probe-target interactions occur.

In a specific embodiment, a biological probe-target binding reaction can be measured in the presence of agonists, antagonists, drugs, or small molecules which can block, initiate or otherwise modulate the binding strength (e.g., equilibrium constant) of the said probe-target binding reaction. This embodiment can be useful in many cases, for example when one would like to know the efficacy of a drug's ability to block or modulate a certain probe-target reaction for medical uses or basic research.

Detection of Conformational Changes

Conformational changes can be studied by the present invention at an interface or in the bulk, where the conformational change leads to a change in one or more physical properties of one or more nonlinear light beams emanating from the sample. The conformational change can be initiated by a biological or chemical binding event, or by a biological component, drug, small molecule, agonist or antagonist binding to a molecule or a particle, and can be assayed as described herein for binding interactions.

In a specific embodiment, a change in orientation or dipole moment occurs in the interfacial region possessing a nonlinear susceptibility as a result of some probe-target interaction. A nonlinear-active label can be attached to the probe of interest and binding of the probe to some target (such as a drug candidate tested for its ability to activate the probe and thereby induce a conformational change) in solution results in a change in orientation or dipole moment and this changes the nonlinear susceptibility of the interfacial region, and thus the properties of the nonlinear beams (e.g., intensity, polarization, wavelength).

In another embodiment, a non-centrosymmetric region is created by application of an external field (EFISH technique). The region can be interfacial, bulk or some combination thereof. Probes or targets (the probes, targets or both are nonlinear-active, either intrinsically or labeled using a nonlinear-active label) are poled by the electric field and this results in a background. When a binding reaction occurs between the probes and targets, this can activate a conformational change in one or both species or result in a change in dipole moment of species, resulting in a change in the measured nonlinear optical signals.

For use with nucleic acid hybridization (oligonucleotide, polynucleotide, RNA, etc.), target oligonucleotides can be exposed to a surface of an array on which are situated probe oligonucleotides. At the probe oligonucleotide sequences in the array (corresponding to known locations) where sequence-complementary hybridization and an accompanying conformational change occurs, the fundamental light would give rise to a change in nonlinear optical signal, or a change in the background of such a signal. This can be detected and correlated with the spatial location of the array element and hence the oligonucleotide sequence. For example, two major applications of nucleic acid microarrays are: 1) identification of sequence (gene or gene mutation)—monitoring of DNA variations, for example; and 2) determination of expression level (abundance) of genes. There are many formats that can be used for preparing the arrays. For example, in one case probe cDNA (500~5000 base pairs long) can be immobilized to a solid surface such as glass using robot spotting and exposed to a set of targets either separately or in a mixture (R. Ekins, F. W. Chu, Trends in Biotechnology, 1999, 17, 217). Another format involves synthesizing oligonucleotides (20~25 mer oligos) or peptide nucleic acids probes in-situ (on the solid substrate, Fodor et al., "Light-directed, Spatially Addressable Parallel Chemical Synthesis," Science 251 (4995): 767-773 Feb. 15, 1999) or by conventional synthesis followed by on-chip immobilization. The array is then exposed to target DNA, hybridized, and the identity or abundance of complementary sequences are determined.

Protein arrays can be prepared (see for example, G. MacBeath and S. L. Schreiber, "Printing Proteins as Microarrays for High-Throughput Function Determination", Science 2000, 289, 1760-1763) to determine whether a given target protein binds to the immobilized probe protein on the surface. These arrays can be used to study small molecule binding to the probe proteins.

Many reviews of microarray technology and applications are available in the art. For instance, those of: Ramsay, "DNA chips—states-of-the-art," Nature Biotechnology 1998, 16(1), 40-44 (relevant portions of which are incorporated by reference herein); Marshall et al., "DNA chips—an array of possibilities," Nature Biotechnology 1998, 16(1), 27-31 (relevant portions of which are incorporated by reference herein); S. A. Fodor, Science 277 (1997), 393 (relevant portions of which are incorporated by reference herein); D. H. Duggan et al., Nature Genet. 21 (Suppl.) (1999), 10 (relevant portions of which are incorporated by reference herein); M. Schena et al., Science 270 (1995), 467 (relevant portions of which are incorporated by reference herein); L. McAllister et al., Am. J. Hum. Genet. 61 (Suppl.) (1997), 1387 (relevant portions of which are incorporated by reference herein); and A. P. Blanchard et al., Biosens. And Bioelectron. 11 (1996) 687 (relevant portions of which are incorporated by reference herein).

The conformational changes also allow enable studying the degree or extent of binding between a probe and a target, utilizing the surface selective nonlinear optical techniques, through measuring the conformational effect the binding induces. In a specific embodiment, probes that are labeled with a nonlinear-active label are attached to a solid surface or substrate. When the probes bind to a target, the conformation of the probe changes, and the orientation of the label with respect to the surface, and fundamental beam changes also. In a preferred embodiment the candidate binding partners (probes) are not attached to the surface. In another embodiment the nonlinear active label or moiety is attached to the target or probe molecules in vitro. The degree of probe-target binding can be correlated via the amount of change of a measured property of the nonlinear optical radiation (e.g., intensity). For example, labeled oligonucleotides are attached to a solid substrate according to means well known in the art and exposed to targets to test for hybridization. When hybridization to a target occurs, the orientation of the label on the oligonucleotide changes. Microarrays known in the art (varying sequence of oligos in different surface locations) or substrates with uniform oligonucleotide sequences can be used. Binding between surface-attached proteins and targets—other proteins, ligands, etc. wherein the binding reaction triggers a conformational change are another exemplary embodiment with the present invention. In general, any surface-attached species that undergoes a conformational change when binding or interacting with any other species or stimulus can be studied with the present invention. Furthermore, the surface-attached probes need not be labeled when using indicators which are sensitive to minute changes in electric charge density or changes thereof. If the conformational change in a probe results in a change in the arrangement of electric charges on a surface—even if this change is transient—indicators near the interface can be used to detect these changes and report on the conformational change.

In a specific embodiment, a MB analogue probe, described above, is used to detect the degree or extent of binding. For instance, by labeling the molecular beacon probe with a nonlinear-active label and measuring whether the label's orientation changes (via changes in nonlinear optical intensity) at some interface, or in the bulk, one can study whether target strands are complementary, and the extent to which they are complementary since the amount of change that is measured in nonlinear optical intensity can be correlated with the degree of hybridization. In a specific embodiment, an Au nanoparticle is used to enhance the intensity of nonlinear optical radiation, such as second harmonic generation scattered by an oxazole dye by several orders of magnitude when the nanoparticle and oxazole dye are in proximity to each other. Upon hybridization of the probe to a complementary target, the intensity of the nonlinear optical radiation decreases and this decrease can be quantitatively related to the amount of probe-target hybridization. The sensitivity of the technique is determined by, among other factors, the background nonlinear optical signal before hybridization occurs.

Variations on Uses of the Invention

Although the present invention can be used in many scientific areas of analysis and in particular, in the chemical and biological arts, the present invention can be especially useful in drug discovery or in fundamental studies where compounds (targets) are tested for binding and ability to activate probes, wherein the probes are ion channel proteins, GPCR proteins, or other receptors, or other molecules.

A wide flexibility is provided for the apparatus. Scanning, imaging, detection techniques at a fixed position, etc. can all be readily used with the present invention. Scanning of microarrays in the art includes confocal-based schemes and non-confocal based schemes. U.S. Pat. No. 5,834,758 (Trulson et al. —relevant portions of which are incorporated by reference herein) describes a non-confocal based scheme for imaging a microarray using fluorescence detection. However, the sample should lie very flat in order to image only within a single focal plane for good out-of-plane discrimination. Therefore, a very finely adjustable translation stage requiring specialized components is preferably be used for this purpose adding to the cost of the instrument and possibly the lifetime as well. The image quality of this type of apparatus can be sensitive to mechanical vibrations. Furthermore, discrimination of the out-of-plane (non-surface bound) fluorophores places a limit on the sensitivity of the technique. U.S. Pat. No. 6,134,002 (Stimson et al. —relevant portions of which are incorporated by reference herein) is an example of a confocal scanning microscope device for imaging a sample plane, i.e. a microarray. Although the confocal-based techniques have good depth discrimination, the scan rate may be low due to descanning requirements and the light throughput can be low, reducing the overall signal to noise ratio and the sensitivity of the technique.

The invention can be used for studying binding processes between other biological components: cells with viruses; protein-protein interactions; protein-ligand; cell-ligand; protein-drugs, nucleic acid-drugs, cell-small molecule; cell-nucleic acid; peptide-cell, oligo or polynucleotides, virus-cell, protein-small molecule, etc., and in general, any binding reaction which results in a conformational change. Biomimetic membranes such as phospholipid supported bilayers (e.g., egg phosphatidylcholine) can also be used and are particularly useful when studies involve membrane protein probes.

Probes, targets, receptors, etc. can be rendered nonlinear-active (made to possess a hyperpolarizability) by direct labeling or by using a decorator molecule or other candidate that has a binding affinity for the probes or targets, and is itself intrinsically or rendered nonlinear-active, and which will respond to a conformational change on the probes or targets by shifting its position, by virtue of the molecular bond that binds the decorator to the probe or target. An antibody to a receptor is an example of such a decorator molecule. The decorator molecule should not itself block the active region of the receptor so that potential agonists, inhibitors, activators, etc. can bind to and produce action on the receptor.

Another example of the invention's use is to label receptors or other components that have an affinity for some virus. When the virus binds or interacts with the receptor or other component, this interaction will affect the orientation of the label with respect to the direction of the fundamental beam, and thus change the properties of the measured nonlinear optical light (e.g., the intensity of the nonlinear light).

Other examples of the technique's use with arrays include cellular arrays, supported lipid bilayer arrays with or without membrane or attached proteins, etc. Many methods exist in the art for coupling biomolecules (e.g., nucleic acid, protein and cells) to solid supports in array format. A wide degree of flexibility may be used in providing the means by which the arrays are created. They can involve, for example, covalent or non-covalent coupling to the substrate directly, to a chemically derivatized substrate, to an intermediate layer of some kind (e.g., self-assembled monolayer, a hydrogel or other bio-compatible layer known in the art). The identity of the probes (e.g., protein structure or oligonucleotide sequence) can vary from site to site across the solid surface, or the same probe can uniformly cover the surface. Targets can be of a single identity or a combination of targets with different identities. The arrays can be prepared in a variety of ways including, but not limited to, ink-jet printing, photolithography, micro-contact printing, or any other manner known to one skilled in the art of fabricating them.

Because the binding process can be measured in real time and in the presence of bulk biological components due to the surface-selectivity of the nonlinear optical technique, equilibrium binding curves and kinetics can be measured, the bulk concentration of the components can be varied, and a "wash-away" step to remove unbound components, as is used with fluorescence-based detection, may be unnecessary.

A wide degree of flexibility is expected in the design of the apparatus including, but not limited to, the source of the fundamental light, the optical train necessary to control, focus or direct the fundamental and nonlinear light beams, the design of the array, the detection system, and the use of a grating or filters and collection optics. The mode of generation (irradiation) or collection can be varied including, for example, the use of evanescent wave (total internal reflection), planar wave guide, reflection, or transmission geometries, fiber-optic, near-field illumination, confocal techniques or the use of a microcavity for power build-up, or integrating detection system such as an integrating sphere. A number of methods for scanning a microarray on a solid surface can be adapted for use. Examples include U.S. Pat. No. 5,834,758 to Trulson et al. (1998), U.S. Pat. No. 6,025,601 to Trulson et al. (2000), U.S. Pat. No. 5,631,734 Stem et al. (1997), and U.S. Pat. No. 6,084,991 to Sampas (2000)—relevant portions of which are incorporated by reference herein.

Because the second harmonic light beam makes a definite angle to the surface plane, one can read-out the properties of the nonlinear optical radiation, for instance, as a function of fundamental incidence position in a two-dimensional array format, without needing to mechanically translate the detector or sample and without extensive collection optics. In the 'beam scanning' embodiment, a mechanical translation of sample surface or detector is not required—only a change in a direction and/or angle of the fundamental incidence on the sample (for a fixed sample and detector)—the apparatus offers much faster scanning capability, improved ease of manufacturing and a longer lifetime.

When using the present invention to study an interface, the interface can comprise a silica, glass, silicon, silicon nitride, polystyrene, nylon, plastic, a metal, semiconductor or insulator surface, or any mixtures thereof, or any surface to which probes, such as biological components, can adsorb or be attached. The interface can also include biological cell and liposome surfaces. The attachment or immobilization can occur through a variety of techniques well known in the art. For example, oligonucleotides can be prepared via techniques described in "Microarray Biochip Technology", M. Schena (Ed.), Eaton Publishing, 1998—relevant portions of which are incorporated by reference herein. And, for example with proteins, the surface can be derivatized with aldehyde silanes for coupling to amines on surfaces of biomolecules (G. MacBeath and S. L. Schreiber, "Printing Proteins as Microarrays for High-Throughput Function Determination", Science 2000, 289, 1760-1763—relevant portions of which are incorporated by reference herein). BSA-NHS (BSA-N-hydroxysuccinimide) surfaces can also be used by first attaching a molecular layer of BSA to the surface and then activating it with N,N'-disuccinimidyl carbonate. The activated lysine, aspartate or glutamate residues on the BSA react with surface amines on the proteins.

The present invention can be applied to an ensemble of molecules or to a single molecule—i.e., ensemble reaction measurements or a single-molecule reaction measurement.

Supported phospholipid bilayers can also be used, with or without membrane proteins or other membrane-associated components as, for example, in Salafsky et al., Architecture and function of membrane proteins in planar supported bilayers: A study with photosynthetic reaction centers" Biochemistry 35 (47): 14773-14781 (1996) relevant portions of which are incorporated by reference herein, "Biomembranes", Gennis, Springer-Verlag, Kalb et al., 1992 and Brian et al., "Allogeneic Stimulation of Cyto-toxic T-cells by Supported Planar Membranes," PNAS—Biological Sciences 81 (19): 6159-6163 (1984)—relevant portions of which are incorporated herein. Supported phospholipid bilayers are well known in the art and there are numerous techniques available for their fabrication, with or without associated membrane proteins. These supported bilayers typically should be submerged in aqueous solution to prevent their destruction when they become exposed to air.

Probes can be part of a biological cell, liposome, bead, etc. that naturally form an interface capable of generating nonlinear optical radiation due to their size (although they are nominally centrosymmetric, their diameter is of the order of the wavelength of light in the visible spectrum and this allows for generation of the nonlinear optical light according to well known art). Alternatively, probes can be molecules or particles (e.g., detergent-solubilized receptors) that are induced to orient by the application of an electric field. The use of electric fields to create a non-centrosymmetric region capable of generating nonlinear radiation—e.g., second harmonic, sum frequency or difference frequency generation, is well known in the prior art. One aspect of this prior art is often called 'EFISH'—electric field-induced second harmonic generation. In a specific embodiment, an applied electric field is used to pole molecules within a region to create an ordered (non-centrosymmetric) region within a phase or material; the resulting region is then capable of generating nonlinear optical radiation.

In a specific embodiment, the probe-target hybridization can be measured by detecting the intensity of nonlinear optical light (e.g., second harmonic light) at some position on a substrate with surface-attached probes; the intensity of the second harmonic light changes as labeled targets bind to the probes at the surface and become partially oriented because of the binding, thus satisfying the non-centrosymmetric condition for generation of second harmonic light at the interface. Modeling of the intensity of light with concentration of probe-target binding complexes at the interface can be accomplished using a variety of methods, for instance by calibrating the technique for a given probe-target interaction using radiolabels or fluorescence tags. Controls for non-specific binding of targets to the surface can be performed according to procedures well known to one skilled in the art, for example: i) addition of deliberately non-complementary targets and measuring for surface-selective nonlinear optical signal, or ii) adding blockers which are known to prevent probe-target binding, adding complementary targets and measuring the resulting surface-selective nonlinear optical signal. In case i) the surface-selective nonlinear optical signal change upon addition of non-complementary targets will be substantially lower than upon addition of complementary targets. In case ii) the signal change will be significantly lower in the presence of blocker than in the absence of blocker.

EXAMPLES

Example 1

A Molecular Beacon analogue (MB analogue) oligonucleotide, coupled to a nonlinear-active dye, and purified, is purchased from a commercial source such as Midland Certified Reagent Company (Midland, Tex.). The nonlinear-active oxazole dye used is oxazole (SE) 1-(3-(succinimidyloxycarbonyl)benzyl)-4-(5-(4-methoxyphenyl)oxazol-2-yl)pyridinium bromide (PyMPO, SE: Molecular Probes Corp.) attached via an amine group at the 3' end.

The oligonucleotide is placed into the sample well of an EFISH cell. There are a variety of EFISH cells available in the art. The sample cell described in the publication by C. G. Bethea ('Experimental technique of dc induced SHG in liquids: measurements of the nonlinearity of $CH_2I_2$", Applied Optics 1975, 14, 1447) is used. The direction of the applied electric field is parallel to the electric field of the laser beam. A commercial femtosecond mode-locked system (Mira 900 and Verdi 5W) is used as the fundamental source. The fundamental is directed into the region of the cell between the electrodes. The back-reflected second harmonic is blocked from entering the oscillator using a color filter; fundamental light beyond the sample is blocked using a color filter. The second harmonic light is collected and focused onto a monochromator (CM 110 CVI Laser) using plano-convex lenses (Melles Griot Inc.). The light is detected using a Hamamatsu photomultiplier tube with a Bertan power supply. The signals from the photomultiplier are sent to a Stanford Research Systems SR400 photon counting unit and processed using a PC. An electric field is applied using a Bertan power supply and home-built electronics to pulse and synchronize the field with the laser pulses.

The dye-labeled MB analogue probes are poled by application of the electric field when it is on. By comparing the average second harmonic intensity of the poled MB analogues in the absence and presence of target, the binding affinity (or sequence if it is unknown) of the target to the MB analogue can be measured. The SHG signal in the absence of target represents a background measurement that is used as a 'baseline' to compare with the signal in the presence of the target.

Upon addition of a perfect complementary target, the MB analogue probe is activated and this leads to a conformational change and therefore to a change in the average orientation of the nonlinear-active dye. Because the intensity of the measured SHG light is proportional to the average orientation of the nonlinear-active dye, a change in dye orientation results in a change in the intensity of the second harmonic beam. Targets with less than perfect complementarity to the MB analogue probe sequence will bind with a lower affinity to the MB analogue probe and will therefore activate a lower proportion of the MB analogue probe molecules and cause a smaller amount of the conformational change. A relationship between binding affinity and the intensity of the second harmonic beam can be readily developed according to procedures known in the art that relate a change in nonlinear intensity to concentration of the nonlinear-active species.

Example 2

Figure 17:
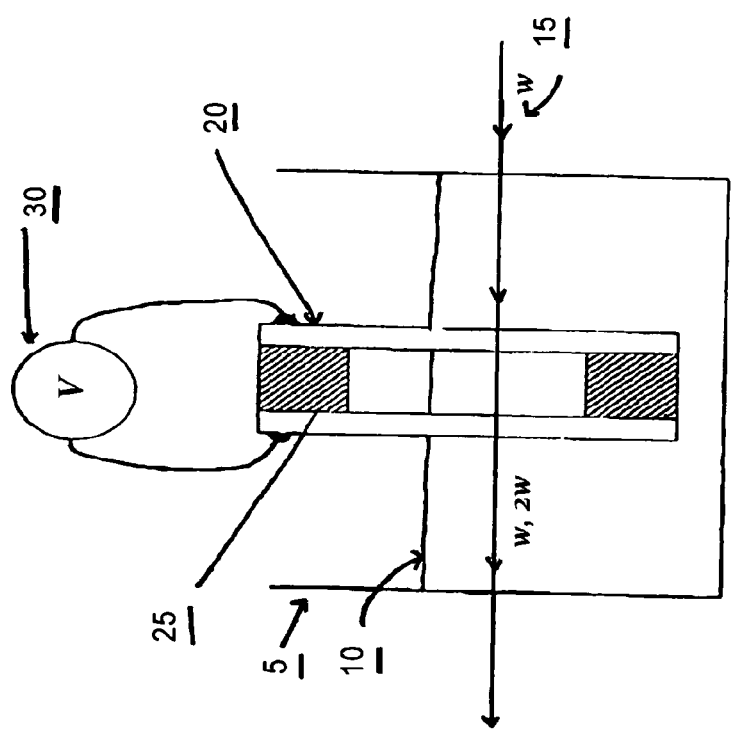
FIG. 17 depicts one embodiment of the sample cell with an applied electric field. The sample cell (5) is open and is depicted side-on and filled with solution (10) containing probes and targets. The fundamental beam enters the sample cell to the right (15) and passes through transparent electrodes (20) separated by a spacer of 1-3 mm (25). The electrodes are connected to a source of voltage (30). When voltage is applied, the targets and probes become partially oriented, thus producing the nonlinear optical light (e.g., second harmonic light).
Figure 18:
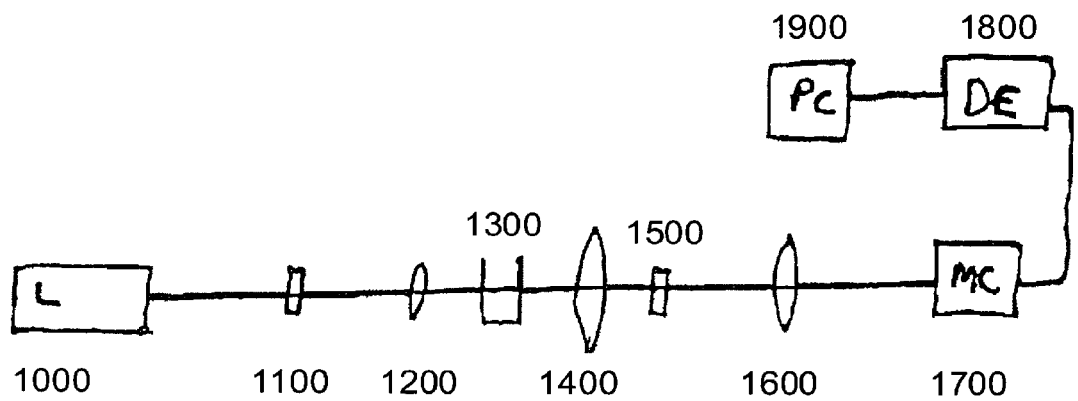
FIG. 18 depicts an apparatus for measuring probe-target interactions in suspended cells. A source of fundamental light from a Ti:Sapphire femtosecond laser (1000) operating at 800 nm is directed through a filter (RG-645, CVI Laser) that blocks 400 nm light (second harmonic). The fundamental is then focused using plano-convex lens 1200 (100 mm focal length, Melles Griot) into sample holder 1300 containing a suspension of biological cells. The second harmonic light is collected parallel to the fundamental direction using a 80 mm diameter plano-convex collimating lens (1400) (120 mm focal length, Melles Griot) that is positioned to have its focus at the focus of lens 1200. The light is sent through a color filter (BG-39, CVI Laser) to block the fundamental light and pass second harmonic light on to a second plano-convex lens 1600 (120 mm focal length) Melles Griot which focuses the light through a monochromator slit and onto its grating (1700). A photomultiplier is attached to the monochromator and detects the second harmonic light. The signal from the photomultiplier is sent on to photon counting electronics (SR400, Stanford Research Systems) and then passed to a computer 1900 for storage and analysis of the data.
Figure 19A:
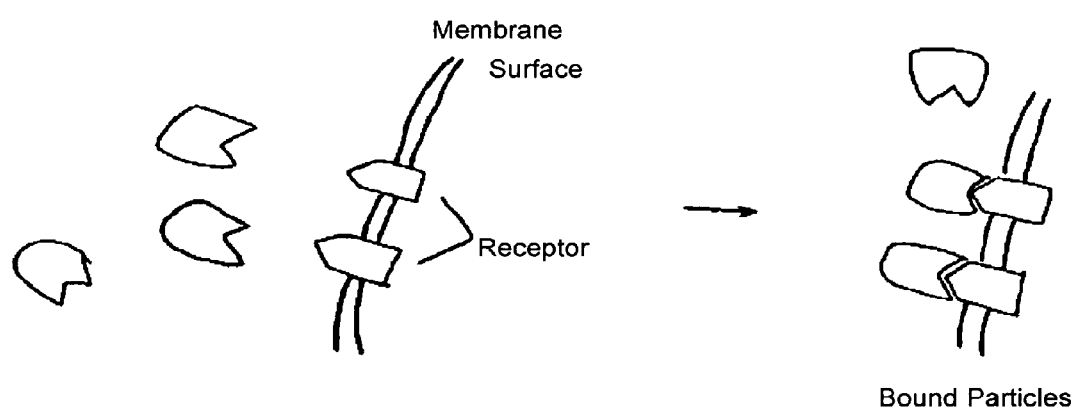
FIGS. 19A-C depict various embodiments of the present invention. In 19A, receptors embedded in a membrane surface are exposed to ligands or particles for which they have an affinity. After the binding interaction occurs, the ligands or particles are bound to the membrane-associated receptors. In 19B, cells are attached (or 'plated') to a surface or substrate to form approximately a monolayer of cells (e.g., ~100% confluent cells); cells can also be stacked to form multilayers at a substrate or surface. In both cases in 19B, incident fundamental light can be transmitted through the substrate or surface, run parallel to the surface and through the multilayer or monolayer of cells, coupled to the cell layer evanescently, or some combination thereof.
Figures 19B, 19C:
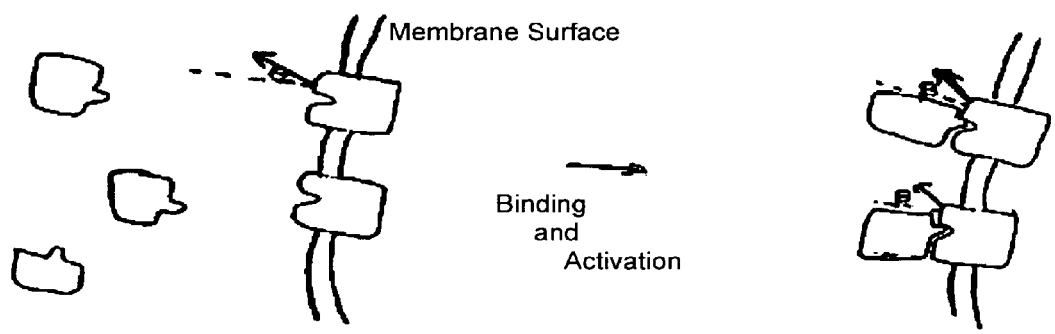

The β2 adrenergic receptor, a GPCR protein, is purified and detergent-solubilized according to well known procedures (e.g., Ghanouni et al., 98(11): 5997 PNAS). The protein is labeled at an endogenous cysteine (Cys-265) with 1-(2,3-epoxypropyl)-4-(5-(4-methoxyphenyl)oxazol-2-yl)pyridinium trifluoromethanesulfonate (PyMPO epoxide, Molecular Probes), a nonlinear-active dye, at 1:1 stoichiometry following standard procedures and using the work of Ghanouni et al., 98(11): 5997 PNAS, as a guide. The nonlinear-active dye is attached to a part of the protein that undergoes a conformational change when the protein is activated. After separation of the non-covalently bound dye, the receptor is placed in a medium situated between two electrodes and through which passes a fundamental beam (e.g., output of ~1 W avg. Power, ~150 fs pulses from a Ti:Sapphire system such as the Verdi-Mira commercial system from Coherent Inc.). The apparatus and sample preparation (e.g., application of electric field, electric field induced second harmonic generation—EFISH) are well known to one of ordinary skill in the art—standard optics are used to focus the fundamental on the sample and to collect the second harmonic radiation. FIG. 18 depicts the apparatus set-up and FIG. 17 depicts the sample holder with applied electric field. An electric field is applied across the medium according to FIG. 17, partially aligning the receptor and its bound dye and creating a non-centrosymmetric condition necessary for observation of SHG. A background signal intensity is measured at 400 nm using a color filter (BG-39, CVI Laser) to block the fundamental, a monochromator to select wavelength (CM110, CVI Laser), a PMT (Hamamatsu) and single-photon counting electronics (SR-400, Stanford Research Systems). The wavelength 400 nm is selected to create a resonance enhancement effect via an electronic transition of the dye. Ligand is added to the medium—a drug candidate that is tested for binding, for example; if the ligand (drug) binds to the receptor, a conformational change in the probe (the receptor) is induced which changes the nonlinear optical signal intensity. Known ligands (isoproterenol) and partial agonists (epinephrine, salbutamol and dobutamine) are used to calibrate the nonlinear optical response with amount of conformational change, i.e., binding affinity.

In an alternate embodiment, the labeling reaction can be carried out using various coupling chemistries and/or stoichiometries (label:probe) to determine which coupling chemistry gives the optimal signal in the nonlinear optical measurement. For instance, it may not be known a priori which subparts of the probes actually undergo a conformational change (positional shift) due to target activation and by undertaking a variety of labeling reactions (known in the art to be necessary to find optimal labeling conditions in fluorescence labeling, etc.), it can be determined which chemistries lead to a label that undergoes conformational change when the probe is activated.

In an alternative embodiment, ion channels or receptors such as GPCR receptors are labeled directly in biological cells with nonlinear-active labels and/or enhancers. For instance, the publication by Glauner et al. (Nature, v. 402 813 (1999)) demonstrates fluorescent labeling of a Shaker potassium ion channel in whole cells. A background signal is measured. When agonist binds to the receptors, it induces a conformational change in the receptors, changing the orientation of the labels and thus the nonlinear optical signal (e.g., the signal intensity). A surface-selective nonlinear optical apparatus is used thus to measure ligand-gated conformational changes in the receptors via the labels and/or enhancers in whole cells. Fundamental light is focused onto a cell layer that has been cultured on Becton-Dickinson Falcon plates, for instance—and the second or higher harmonic is collected according to procedures well known in the art. In an alternative embodiment, the labeled cells are suspended in a medium and fundamental light is focused into a region of the sample containing these cells. FIG. 18 depicts an embodiment of this apparatus. Second harmonic light is collected according to procedures known in the art, for instance at 0 or 90 degrees with respect to the fundamental beam.

In an alternative embodiment, enhancers are suspended or dissolved in the medium with labeled cells or molecules to enhance the nonlinear response of the cells or molecules.

In an alternative embodiment, probes are placed in artificial membranes or liposomes. If probes are expressed in cells, then can be purified and reconstituted into these membranes according to procedures well known in the art.

In an alternative embodiment, the probes are in contact with, cultured on or patterned on surface that is itself in contact with a prism (or is the underside of the prism).

The prism allows total internal reflection of the fundamental at the interface containing the probes and thus high Fresnel factors (electric field amplitudes) leading to higher nonlinear optical signals. In this mode of the set-up, the fundamental beam undergoes total internal reflection at the interface containing the probes and its evanescent wave is used to generate the nonlinear light. FIG. 2 illustrates an embodiment of this type. In FIG. 2, an index matching material or liquid (75) is used to couple the prism (70) to a substrate containing the microarray (80) in contact with solution containing targets (85), whereby total internal reflection occurs at the interface between material (80) and solution (85). The prism material can be, for example, BK7 type glass (Melles Griot) and the index matching material obtained commercially from Corning Corp. or Nye Corp.

In an alternative embodiment, the experimental set-up is as described in Salafsky and Eisenthal, "Protein adsorption at interfaces detected by second harmonic generation," J. Phys. Chem. B, 104 (32): 7752-7755 (2000), Salafsky and Eisenthal, "Second harmonic spectroscopy: detection and orientation of molecules at a biomembrane interface," Chem. Phys. Lett. 319 (5-6): 435-439 (2000), and references set forth therein. A femtosecond pulsed laser (Mail-Tai, Spectra-Physics) is used as the source of fundamental light at 800 nm operating at 80 MHz with <200 fs pulses at 1 W average power. The laser beam directed onto the entrance aperture of a Dove prism (Melles Griot, BK-7) and focused with a concave lens (Oriel) (spot size ~50 micron diameter). The Dove prism is mounted in a Teflon holder and in contact with buffer or distilled water. The beam undergoes total internal reflection (evanescent wave generation) within the prism and the fundamental and second harmonic beams emerge roughly collinearly from the exit aperture. A color filter is used to block the fundamental light while passing the second harmonic to a monochromator (2 nm bandwidth slit). The monochromator is scanned from 380-500 nm to detect the second harmonic spectrum. If necessary, the fundamental light wavelength can be tuned as well. A single photon counting detector and photomultiplier tube are used to detect the output of the monochromator and a PC with software are used to record the data and control the monochromator wavelength. A background second harmonic signal is measured before addition of ligand or other stimulus to produce or test for conformational change in the probes.

Example 3

Oligodeoxyribonucleotides with suitable structures for molecular beacons are selected and synthesized according to procedures known to one of ordinary skill in the art with a primary amine at the 3' end and a disulfide group at the 5' end and a biotin group that replaces a dT. The following MB analogue can be used, for example: 5'-CCT AGC TCT AAA TCG CTA TGG TCG CGC(Biotin dT)AG G-3' (SEQ ID NO: 6). The amine-reactive nonlinear-active oxazole dye: oxazole (SE) 1-(3-(succinimidyloxycarbonyl)benzyl)-4-(5-(4-methoxyphenyl)oxazol-2-yl)pyridinium bromide (PyMPO, SE: Molecular Probes Corp.) is conjugated to the primary amine. In this coupling reaction, a 100 µl solution containing 100 µM oligonucleotide dissolved in 0.1 M sodium bicarbonate is reacted with 0.1 mg of the succinimidyl ester of the dye dissolved in 100 µl of dimethyl sulfoxide. The reaction mixture is stirred at room temperature for 2 hours. The reaction product is purified with a Sephadex column (NAP-5; Amersham Pharmacia Biotech) equilibrated with 10 ml of 0.1 M triethylammonium acetate (pH 6.5). After purification, the 5'-end disulfide is cleaved and the free sulfhydryl is covalently attached to a 1.4 nm diameter gold cluster that serves to enhance the nonlinear response of the oxazole dye (Nanogold; Nanoprobes), and which comes with one N-propylmaleimide and has been passivated with water-soluble phosphine ligands. The coupling of the Au particle is achieved according to procedures well known to one of ordinary skill in the art. For example: the disulfide bond is cleaved with dithiothreitol (DTT), and the oligonucleotide is purified of excess DTT before coupling to the gold. An amount of 10 µl of 1 M DTT is added to 25 µl of oligonucleotide mixed with 75 µl of sodium bicarbonate, pH 8.3. After a one hour incubation, the oligonucleotide solution is purified using reverse-phase chromatography, as described. The fractions containing the activated oligonucleotide are purified using a Sephadex column (NAP-5) equilibrated with water. Part of the elution product (37 pmol to 370 pmol of DNA, suspended in 180 µl of water) is immediately reacted with 6 nmol of the monomaleimido-gold particles (Nanoprobes) in aqueous 20 mM NaH2PO4, 150 mM NaCl, 1 mM ethylenediamine tetraethyl acetate (EDTA) buffer, pH 6.5, containing 10% isopropanol at 4° C. for 24 h. Reaction products are analyzed by gel electrophoresis on a 10% nondenaturing acrylamide gel performed in Tris-borate EDTA (TBE) at 10 V/cm.

The biotinylated MB analogue with attached nonlinear-active dye and gold nanoparticles are coupled to streptavidin-derivatized glass according to well known procedures. For example, the biotinylated MB analogues are immobilized on the etched portion of a glass fiber. A batch of optical fibers is used in a single immobilization cycle. About 2 cm of cladding is stripped away from the core by chemical etching at one end of the fiber probe. The fiber probe is perpendicularly dipped into a 49% hydrofluoric acid solution for 12 min. The HF solution is covered by heptane solvent. The etched fiber probe is washed with ultrapure water before being used for the subsequent immobilization experiment.

Biotinylated MB analogues are immobilized on the etched portion of the fiber for DNA sensing. The etched fiber probes are first cleaned by immersion in a 1:1 v/v concentrated HCl/MeOH mixture for 30 min., rinsed in water, and submerged in concentrated sulfuric acid for 30 min. Further rinsing and then boiling in water for 8-10 min follows. Silanization of the fibers is performed by immersing them in a freshly prepared 1% (v/v) solution of DETA (Trimethoxysilylpropyldiethylenetriamine purchased from United Chemical Technologies, Bristol Pa.) in 1 mM acetic acid for 20 min at room temperature. The DETA-modified fiber probes are thoroughly rinsed with water to remove excess DETA. The silanized fiber probes are dried under nitrogen and fixed by heating in a 120° C. oven for 5 min. Then the silanized fibers are immersed in 0.5 mg/ml NHS-LC-biotin (sulfosuccinimidyl-6-(biotinamido) hexanoate purchased from Pierce, Rockford Ill.) in 0.1 M bicarbonate buffer (pH 8.5) for 3 hours at room temperature. Streptavidin (Sigma, St. Louis Mo.) is bound to the fiber surface by incubating the biotinylated fibers overnight at 4° C. in a solution containing 1.0 mg/ml of the streptavidin. The streptavidin-immobilized optical fibers are then immersed with a biotinylated MB analogue solution ($10^{-6}$ M in 10 mM phosphate buffer at pH 7.0) for as long as 20 min or overnight at 4° C. to allow the biotinylated MB analogue to be immobilized on the surface.

The optical fibers are interrogated optically using second harmonic generation by propagating a fundamental beam down the fiber and measuring the intensity of the second harmonic beam back-reflected after it interacts evanescently with the MB analogue at the distal end of the fiber. In the absence of complementary targets, the oligonucleotide produces a large amount of second harmonic light due to the proximity of the oxazole dye and the Au particle in the hairpin-loop structure of the MB analogue; the intensity of the second harmonic light in this case can serve as a background. In the presence of complementary targets, the hybridization reaction causes the dye and the Au particle to spatially separate, greatly reducing the intensity of the second harmonic light detected. A linear relationship can be constructed between the amount of hybridization that occurs and the intensity of the second harmonic light and thus the derivatized optical fibers with detection system serves as an optical device for detection of complementary targets to the selected probe.

Example 4

Glass microspheres which are optically encoded with fluorescent dyes are derivatized with the MB analogues and an array of microspheres with distinct oligonucleotide probes is prepared at the distal end of an optical fiber as found in the art (e.g., U.S. Pat. No. 5,250,264, Walt et al.; U.S. Pat. No. 5,298,741 Walt et al.; U.S. Pat. No. 5,252,494 Walt et al; U.S. Pat. No. 6,023,540 Walt et al.; U.S. Pat. No. 5,814,524 Walt et al.; U.S. Pat. No. 5,244,813 Walt et al.; U.S. Pat. No. 5,512,490 Walt et al. and commercially (Illumina Corporation, for example). These arrays can be used to detect multiple target sequences. Alternatively, the optical encoding can be accomplished using nonlinear-active dyes with different spectral characteristics from the beacon-associated nonlinear-active dye so that the both the encoding and the hybridization detection can be made using a nonlinear optical technique such as second harmonic generation.

If the nonlinear MB analogues are used in homogeneous solution, an applied electric field can be applied to the MB analogues in an EFISH method to create the required non-centrosymmetric condition.

In an alternative embodiment, one is interested in finding drugs, antagonists, agonists or other species which block or reduce the binding of the MB analogues with targets—these compounds may be referred to as 'inhibitors' or 'blockers.' In this application, labeled targets are bound to probes at the interface. The inhibitors are added to the sample, and if the particular species being tested is successful in blocking or reducing the probe-target binding, the nonlinear optical light measured will change—the background radiation in this embodiment is due to target-probe binding; the displacement of the targets from the probes at the interface by the inhibitors leads to a change in the nonlinear optical light measured, for instance as a decrease in intensity of the nonlinear radiation generated by the interface or a wavelength shift in the nonlinear radiation spectrum.

In an optional embodiment, controls to determine degree of non-specific nonlinear optical signals (e.g., not due to specific probe-target binding) can be performed according to standard procedures well known to one skilled in the art. In nucleic acid microarrays, for example, the intensity of the nonlinear optical signal at regions between the probe-containing regions will produce a background signal that can increase somewhat (but is substantially smaller than the signal due to specific probe-target binding reactions) upon addition of targets that are either complementary or non-complementary to the probes. This background signal can be accounted for by, for example, adding only non-complementary probes and measuring the nonlinear optical signal in regions containing probes and not containing probes. Measuring the nonlinear optical signals in the presence of blockers known to prevent probe-target binding is another control technique well known to one skilled in the art for determining the amount of background or artifactual signal present in a larger signal of interest, in this case the specific probe-target binding reaction.

In another embodiment of the invention, the amine-reactive oxazole dye (SE) 1-(3-(succinimidyloxycarbonyl)benzyl)-4-(5-(4-methoxyphenyl)oxazol-2-yl)pyridinium bromide (PyMPO, SE: Molecular Probes Corp.) is reacted with a 1:1 molar ratio of ethylenediamine under the conditions specified by the Molecular Probes direction and is allowed to react to completion. The oxazole-based dye now contains a single amine group. This can be coupled to the primary amine on an oligonucleotide using a homobifunctional crosslinking agent (Pierce, Rockford Ill.).

In an alternative embodiment, a nonlinear-active dye with attached biotin can be synthesized according to procedures known to one of ordinary skill in the art to create dye-biotin molecules that are the nonlinear-active analogues of the biotin-fluorescent dye molecules useful for immobilization of oligonucleotides.

Example 5

A peptide-nucleic analogue (PNA) molecular beacon (hairpin-loop structure) of 18-25 base-pairs sequence is labeled with PyMPO, SE (Molecular Probes Corp.) at the 3' or 5' end (or, alternatively, at cytosine base-pair locations) according to procedures well established in the art. The PNA is placed in purified water solution and oriented with an applied electric field to generate a non-centrosymmetric region. Addition of PNA molecules with complementary sequence to the labeled PNA will cause a conformational change and thus a change in measured properties of the nonlinear optical beams.

PNAs (linear, non-hairpin loop) can also be attached to glass or silica surfaces according to procedures well known to those skilled in the art. Addition of sequence-complementary DNA to purified water in contact with the glass surface containing the PNAs results in a conformational change in the PNAs on the surface, and thus a change in the measured physical properties of the nonlinear optical light beam.

MISCELLANEOUS

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

I claim:

1. A method for screening one or more candidate binding partners for modulating the conformation of a test molecule, the method comprising:
   (a) illuminating a sample with one or more light beams at one or more fundamental frequencies, said sample comprising said test molecule exposed to said one or more candidate binding partners, wherein a nonlinear-active label is attached to a part of said test molecule that undergoes a conformational change upon interaction with said one or more binding partners, wherein there is no more than one test molecule directly bound to said nonlinear-active label, and wherein said test molecule is nonlinear-active in the absence of an exogenous nonlinear-active label bound to the test molecules;
   (b) measuring one or more physical properties of a second-harmonic or sum-frequency light beam emanating from said sample; and
   (c) comparing a value of said one or more physical properties measured in step (b) to a value for said one or more physical properties measured in the absence of exposure of said test molecule to said one or more candidate binding partners, wherein a change in the value of said one or more physical properties measured in step (b) relative to the value for said one or more physical properties measured in the absence of exposure of said test molecule to said one or more candidate binding partners indicates that said one or more candidate binding partners modulate the conformation of said test molecule.

2. A method for screening one or more candidate binding partners for modulating the conformation of a test molecule, the method comprising:
   (a) illuminating a sample with one or more light beams at one or more fundamental frequencies, said sample comprising said test molecule exposed to said one or more candidate binding partners, wherein a nonlinear-active label is attached to a part of said test molecule that undergoes a conformational change upon interaction with said one or more binding partners, and wherein there is no more than one test molecule directly bound to said nonlinear-active label;
   (b) measuring one or more physical properties of a second-harmonic or sum-frequency light beam emanating from said sample; and
   (c) comparing a value of said one or more physical properties measured in step (b) to a value for said one or more physical properties measured in the absence of exposure of said test molecule to said one or more candidate binding partners, wherein a change in the value of said one or more physical properties measured in step (b) relative to the value for said one or more physical properties measured in the absence of exposure of said test molecule to said one or more candidate binding partners indicates that said one or more candidate binding partners modulate the conformation of said test molecule;
wherein the sample in step (b) further comprises at least one decorator with nonlinear activity that specifically binds to a candidate binding partner.

3. A method for screening one or more candidate binding partners for modulating the conformation of a test molecule, the method comprising:
   (a) illuminating a sample with one or more light beams at one or more fundamental frequencies, said sample comprising said test molecule exposed to said one or more candidate binding partners, wherein a nonlinear-active label is attached to a part of said test molecule that undergoes a conformational change upon interaction with said one or more binding partners, and wherein there is no more than one test molecule directly bound to said nonlinear-active label;
   (b) measuring one or more physical properties of a second-harmonic or sum-frequency light beam emanating from said sample; and
   (c) comparing a value of said one or more physical properties measured in step (b) to a value for said one or more physical properties measured in the absence of exposure of said test molecule to said one or more candidate binding partners, wherein a change in the value of said one or more physical properties measured in step (b) relative to the value for said one or more physical properties measured in the absence of exposure of said test molecule to said one or more candidate binding partners indicates that said one or more candidate binding partners modulate the conformation of said test molecule
wherein the sample in step (b) further comprises at least one decorator with nonlinear activity that specifically binds to a test molecule.

4. A method for screening one or more candidate binding partners for modulating the conformation of a test molecule, the method comprising:
   (a) illuminating a sample with one or more light beams at one or more fundamental frequencies, said sample comprising said test molecule exposed to said one or more candidate binding partners, wherein a nonlinear-active label is attached to a part of said test molecule that undergoes a conformational change upon interaction with said one or more binding partners, and wherein there is no more than one test molecule directly bound to said nonlinear-active label;
   (b) measuring one or more physical properties of a second-harmonic or sum-frequency light beam emanating from said sample; and
   (c) comparing a value of said one or more physical properties measured in step (b) to a value for said one or more physical properties measured in the absence of exposure of said test molecule to said one or more candidate binding partners, wherein a change in the value of said one or more physical properties measured in step (b) relative to the value for said one or more physical properties measured in the absence of exposure of said test molecule to said one or more candidate binding partners indicates that said one or more candidate binding partners modulate the conformation of said test molecule
wherein the sample in step (b) further comprises at least one decorator with nonlinear activity that specifically binds to a complex comprising one or more candidate binding partners bound to a test molecule.

5. A method for screening one or more candidate binding partners for modulating the conformation of a test molecule comprising:
   (a) illuminating a sample with one or more light beams at one or more fundamental frequencies, said sample comprising said test molecule exposed to said one or more candidate binding partners, wherein a nonlinear-active label is attached to a part of said test molecule that undergoes a conformational change upon interaction with said one or more binding partners, wherein there is no more than one test molecule directly bound to said nonlinear-active label, and wherein said test molecule is nonlinear-active in the absence of an exogenous nonlinear-active label bound to the test molecules;
   (b) measuring one or more physical properties of a second-harmonic or sum-frequency light beam emanating from a sample in step (a);
   (c) illuminating a sample in step (a) with one or more light beams at one or more fundamental frequencies, said sample further comprising a known modulator of said test molecule;
   (d) measuring one or more physical properties of a second-harmonic or sum-frequency light beam emanating from said a sample in step (c); and
   (e) comparing a value of said one or more physical properties measured in step (b) to a value for said one or more physical properties measured in step (d), wherein a change in the value of said one or more physical properties measured in step (b) relative to the value for said one or more physical properties measured in step (d) indicates that said one or more candidate binding partners modulate the conformation of said test molecule.

6. A method for screening one or more candidate binding partners for modulating the conformation of a test molecule comprising:
   (a) illuminating a sample with one or more light beams at one or more fundamental frequencies, said sample comprising said test molecule exposed to said one or more candidate binding partners, wherein a nonlinear-active label is attached to a part of said test molecule that undergoes a conformational change upon interaction with said one or more binding partners, and wherein there is no more than one test molecule directly bound to said nonlinear-active label;

(b) measuring one or more physical properties of a second-harmonic or sum-frequency light beam emanating from a sample in step (a);
(c) illuminating a sample in step (a) with one or more light beams at one or more fundamental frequencies, said sample further comprising a known modulator of said test molecule;
(d) measuring one or more physical properties of a second-harmonic or sum-frequency light beam emanating from said a sample in step (c); and
(e) comparing a value of said one or more physical properties measured in step (b) to a value for said one or more physical properties measured in step (d), wherein a change in the value of said one or more physical properties measured in step (b) relative to the value for said one or more physical properties measured in step (d) indicates that said one or more candidate binding partners modulate the conformation of said test molecule wherein the sample in step (b) and/or step (d) further comprises at least one decorator with nonlinear activity that specifically binds to a candidate binding partner.

7. A method for screening one or more candidate binding partners for modulating the conformation of a test molecule comprising:

(a) illuminating a sample with one or more light beams at one or more fundamental frequencies, said sample comprising said test molecule exposed to said one or more candidate binding partners, wherein a nonlinear-active label is attached to a part of said test molecule that undergoes a conformational change upon interaction with said one or more binding partners, and wherein there is no more than one test molecule directly bound to said nonlinear-active label;
(b) measuring one or more physical properties of a second-harmonic or sum-frequency light beam emanating from a sample in step (a);
(c) illuminating a sample in step (a) with one or more light beams at one or more fundamental frequencies, said sample further comprising a known modulator of said test molecule;
(d) measuring one or more physical properties of a second-harmonic or sum-frequency light beam emanating from said a sample in step (c); and
(e) comparing a value of said one or more physical properties measured in step (b) to a value for said one or more physical properties measured in step (d), wherein a change in the value of said one or more physical properties measured in step (b) relative to the value for said one or more physical properties measured in step (d) indicates that said one or more candidate binding partners modulate the conformation of said test molecule wherein the sample in step (b) and/or step (d) further comprises at least one decorator with nonlinear activity that specifically binds to a test molecule.

8. A method for screening one or more candidate binding partners for modulating the conformation of a test molecule comprising:

(a) illuminating a sample with one or more light beams at one or more fundamental frequencies, said sample comprising said test molecule exposed to said one or more candidate binding partners, wherein a nonlinear-active label is attached to a part of said test molecule that undergoes a conformational change upon interaction with said one or more binding partners, and wherein there is no more than one test molecule directly bound to said nonlinear-active label;
(b) measuring one or more physical properties of a second-harmonic or sum-frequency light beam emanating from a sample in step (a);
(c) illuminating a sample in step (a) with one or more light beams at one or more fundamental frequencies, said sample further comprising a known modulator of said test molecule;
(d) measuring one or more physical properties of a second-harmonic or sum-frequency light beam emanating from said a sample in step (c); and
(e) comparing a value of said one or more physical properties measured in step (b) to a value for said one or more physical properties measured in step (d), wherein a change in the value of said one or more physical properties measured in step (b) relative to the value for said one or more physical properties measured in step (d) indicates that said one or more candidate binding partners modulate the conformation of said test molecule wherein the sample in step (b) and/or step (d) further comprises at least one decorator with nonlinear activity that specifically binds to a complex comprising one or more candidate binding partners bound to a test molecule.

* * * * *

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      oligonucleotide molecular beacon analogue hybridization target 1

<400> SEQUENCE: 1
aaaaaaaaaa aaaaactcgc                                              20

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence:
      oligonucleotide molecular beacon analogue hybridization target 2

<400> SEQUENCE: 2
gaaaaaaaaa aaaaaa                                                  16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence:
      oligonucleotide molecular beacon analogue hybridization target 3

<400> SEQUENCE: 3
gaaaaaaaca aaaaaa                                                  16

<210> SEQ ID NO 4
<211> LENGTH: 69
<212> TYPE: DNA
<213> ORGANISM: Artificial Sequence
<220> FEATURE:
<223> OTHER INFORMATION: Description of Artificial Sequence:
      oligonucleotide molecular beacon analogue hybridization target 4
<220> FEATURE:
<221> NAME/KEY: modified_base
<222> LOCATION: (20)..(49)
<223> OTHER INFORMATION: n = g, a, c or t
<220> FEATURE:
<221> NAME/KEY: misc_feature
<222> LOCATION: (20)..(49)
<223> OTHER INFORMATION: n is a, c, g, or t

<400> SEQUENCE: 4
ctacctacag taccagcttn nnnnnnnnnn nnnnnnnnnn nnnnnnnnnt tactcgaggg   60
atcctagtc                                                          69

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      oligonucleotide molecular beacon analogue with attached dye and
      enhancer (Au particle)
<220> FEATURE:
<221> NAME/KEY: modified_base
<222> LOCATION: (1)..(1)
<223> OTHER INFORMATION: n = g bound to Au particle substituted by
      multiple -Ar-3P phosphine ligands, where Ar =

-continued

```
      methylcarbonylphenyl, through a
      phosphohexylthiosuccinimidyl-methylcarbonylphenyl linker to a
      phosphine group
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (25)..(25)
<223> OTHER INFORMATION: n = c linked to a dye via an amidohexyloxy
      group
<220> FEATURE:
<221> NAME/KEY: misc_feature
<222> LOCATION: (25)..(25)
<223> OTHER INFORMATION: n is a, c, g, or t

<400> SEQUENCE: 5
ncgagttttt tttttttttt ctcgn                                           25

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence:biotinylated
      oligodeoxyribonucleotide molecular beacon analogue
<220> FEATURE:
<221> NAME/KEY: modified_base
<222> LOCATION: (1)..(1)
<223> OTHER INFORMATION: n = c substituted with a disulfide group
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (28)..(28)
<223> OTHER INFORMATION: n = t modified by biotin (Biotin dT)
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: modified_base
<222> LOCATION: (31)..(31)
<223> OTHER INFORMATION: n = g modified by primary amine conjugated to
      1-(3-succinimidyloxycarbonyl)benzyl)-4-(5-(4-methoxyphenyl)oxazol
      -2-yl)pyridinium bromide (oxazole (SE), PyMPO)
<220> FEATURE:
<221> NAME/KEY: misc_feature
<222> LOCATION: (31)..(31)
<223> OTHER INFORMATION: n is a, c, g, or t

<400> SEQUENCE: 6
nctagctcta aatcgctatg gtcgcgcnag n                                    31
```